(12) United States Patent
Ogasawara

(10) Patent No.: US 11,325,961 B2
(45) Date of Patent: May 10, 2022

(54) NATURAL KILLER CELL FUNCTION ENHANCER

(71) Applicant: TOHOKU UNIVERSITY, Sendai (JP)

(72) Inventor: Koetsu Ogasawara, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 475 days.

(21) Appl. No.: 16/323,365

(22) PCT Filed: Aug. 4, 2017

(86) PCT No.: PCT/JP2017/028490
§ 371 (c)(1),
(2) Date: Feb. 5, 2019

(87) PCT Pub. No.: WO2018/026018
PCT Pub. Date: Feb. 8, 2018

(65) Prior Publication Data
US 2019/0185539 A1    Jun. 20, 2019

(30) Foreign Application Priority Data

Aug. 5, 2016  (JP) .............................. JP2016-154742

(51) Int. Cl.
| | | |
|---|---|---|
| *C07K 14/725* | (2006.01) | |
| *A61P 35/00* | (2006.01) | |
| *C07K 19/00* | (2006.01) | |
| *A61P 43/00* | (2006.01) | |
| *A61K 38/17* | (2006.01) | |
| *A61P 31/00* | (2006.01) | |
| *C12P 21/00* | (2006.01) | |
| *A61P 35/04* | (2006.01) | |
| *C07K 14/705* | (2006.01) | |
| *C12Q 1/02* | (2006.01) | |
| *G01N 33/574* | (2006.01) | |

(52) U.S. Cl.
CPC .......... *C07K 14/7051* (2013.01); *A61K 38/17* (2013.01); *A61P 31/00* (2018.01); *A61P 35/00* (2018.01); *A61P 35/04* (2018.01); *A61P 43/00* (2018.01); *C07K 14/7056* (2013.01); *C07K 19/00* (2013.01); *C12P 21/00* (2013.01); *C12Q 1/02* (2013.01); *G01N 33/57492* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | |
|---|---|---|
| 2003/0012782 A1 | 1/2003 | Gold |
| 2003/0144474 A1* | 7/2003 | Weidanz ................. A61P 35/00 530/350 |
| 2005/0214284 A1 | 9/2005 | Price-Schiavi |
| 2013/0115191 A1 | 5/2013 | Weidanz et al. |
| 2016/0199523 A1 | 7/2016 | Price-Schiavi et al. |
| 2016/0289760 A1 | 10/2016 | Suzuki et al. |

FOREIGN PATENT DOCUMENTS

| | | |
|---|---|---|
| JP | 2003-534821 A | 11/2003 |
| JP | 2004-506021 A | 2/2004 |
| JP | 2007-513326 A | 5/2007 |
| JP | 2008-263950 A | 11/2008 |
| WO | 2015/075939 A1 | 5/2015 |

OTHER PUBLICATIONS

Ogasawara K. et al., Clin J Immunol; 25(6):534-540, Nov. 2005.
Mosquera et al., "In Vitro and In Vivo Characterization of a Novel Antibody-Like Single-Chain TCR Human IgG1 Fusion Protein", The Journal of Immunology, 2005, vol. 174, No. 7, pp. 4381-4388.
Lunde et al., "Stabilizing mutations increase secretion of functional soluble TCR-Ig fusion proteins", BMC Biotechnology, 2010, vol. 10, No. 1, p. 61.
Ozawa et al., "The binding affinity of a soluble TCR-Fc fusion protein is significantly improved by crosslinkage with an anti-C[beta] antibody", Biochemical and Biophysical Research Communications, 2012, vol. 422, No. 2, pp. 245-249.
Supplementary Partial European Search Report for Corresponding European Application No. 17837119.1 (12 Pages) (dated Mar. 2, 2020).

* cited by examiner

*Primary Examiner* — Elly-Gerald Stoica
(74) *Attorney, Agent, or Firm* — Lucas & Mercanti, LLP

(57) ABSTRACT

To provide a therapy and a diagnosis of cancer or an infection using recognition mechanism of a T-cell receptor. An NK cell function enhancer comprises, an active ingredient, a T-cell receptor chimeric protein being a fusion protein of: a T-cell receptor variable region capable of recognizing a cancer-specific antigen or a T-cell receptor variable region capable of recognizing an antigen specific to a pathogen causative of an infection, and an immunoglobulin Fc region, wherein the T-cell receptor chimeric protein binds to an MHC molecular complex of a cancer cell to down-modulate an MHC class I molecule complex, and the cancer cell is killed or damaged by recognition of an NK cell; and an NK cell function enhancer for imparting to an NK cell a function of recognizing a cancer cell or an infected cell infected with a pathogen causative of an infection, which expresses an MHC class I molecule, and killing or damaging the cancer cell or the infected cell by TDCC (T-cell receptor chimeric protein-dependent cellular cytotoxicity) activity.

8 Claims, 38 Drawing Sheets

Specification includes a Sequence Listing.

TCR-IgFc dependent
cellular cytotoxicity
(TDCC)

Fig. 13

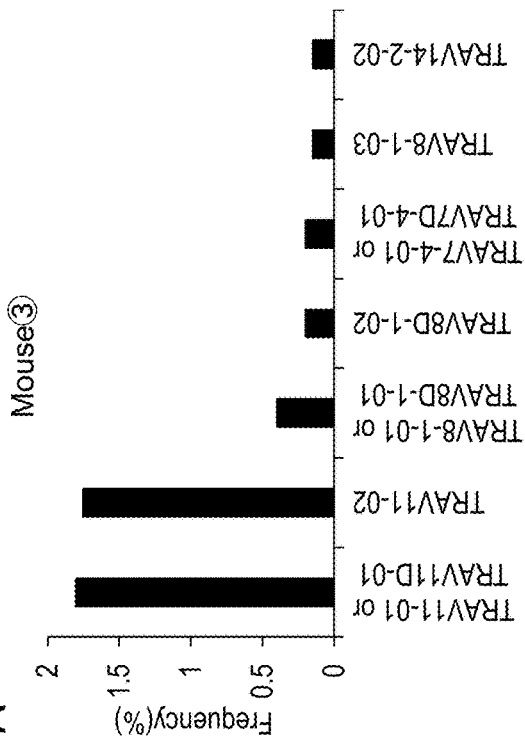

A. 10 days after administration of E.G7 Mouse③

| | V-Gene and allele | J-Gene and allele | CDR-3 |
|---|---|---|---|
| ① | TRAV11-01 / TRAV11D-01 | TRAJ18-01 | VVGDRGSALGRLH (SEQ ID NO:2) |
| ② | TRAV11-02 | TRAJ18-01 | VVGDRGSALGRLH (SEQ ID NO:2) |
| ③ | TRAV8-1-01 / TRAV8D-1-01 | TRAJ42-01 | ATLYSGGSNAKLT (SEQ ID NO:1) |
| ④ | TRAV8D-1-02 | TRAJ42-01 | ATLYSGGSNAKLT (SEQ ID NO:1) |
| ⑤ | TRAV7-4-01 / TRAV7D-4-01 | TRAJ31-01 | AASRNSNNRIF (SEQ ID NO:7) |

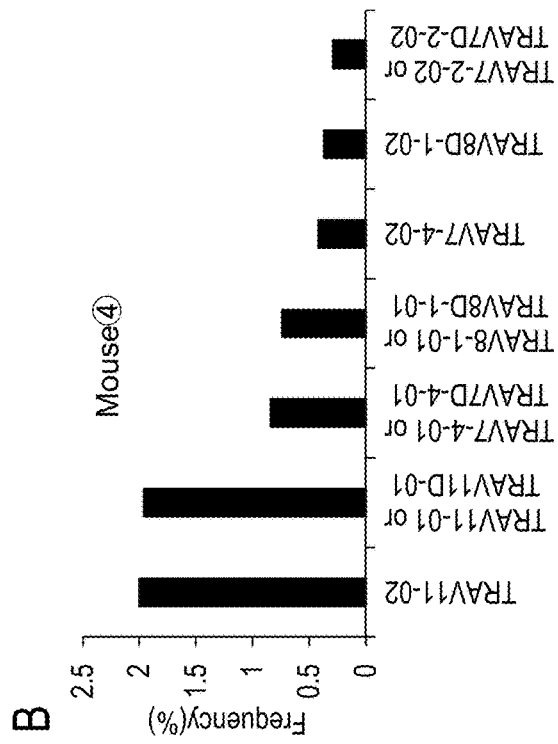

B. Mouse④

| | V-Gene and allele | J-Gene and allele | CDR-3 |
|---|---|---|---|
| ① | TRAV11-02 | TRAJ18-01 | VVGDRGSALGRLH (SEQ ID NO:2) |
| ② | TRAV11-01 / TRAV11D-01 | TRAJ18-01 | VVGDRGSALGRLH (SEQ ID NO:2) |
| ③ | TRAV7-4-01 / TRAV7D-4-01 | TRAJ26-01 | AASENNYAQGLT (SEQ ID NO:8) |
| ④ | TRAV8-1-01 / TRAV8D-1-01 | TRAJ42-01 | ATLYSGGSNAKLT (SEQ ID NO:1) |
| ⑤ | TRAV7-4-02 | TRAJ26-01 | AASENNYAQGLT (SEQ ID NO:8) |

Fig. 14

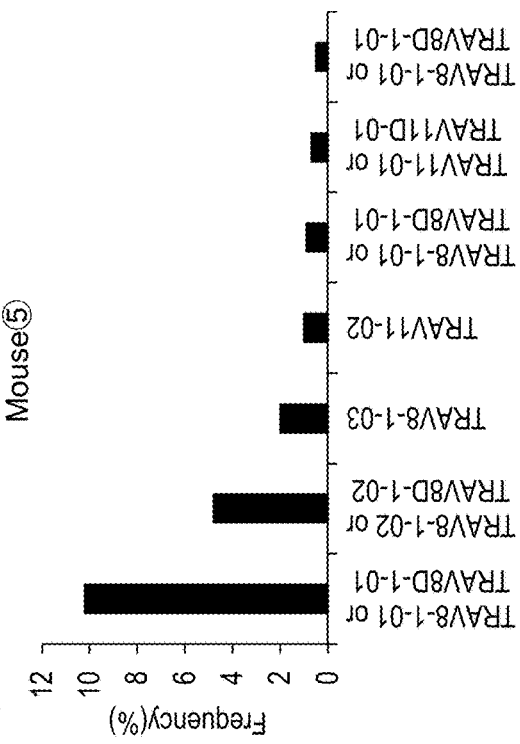

A 15 days after administration of E.G7 — Mouse ⑤

| | V-Gene and allele | J-Gene and allele | CDR-3 |
|---|---|---|---|
| ① | TRAV8-1-01 / TRAV8D-1-01 | TRAJ42-01 | ATLYSGGSNAKLT (SEQ ID NO:1) |
| ② | TRAV8-1-02 / TRAV8D-1-02 | TRAJ42-01 | ATLYSGGSNAKLT (SEQ ID NO:1) |
| ③ | TRAV8-1-03 | TRAJ42-01 | ATLYSGGSNAKLT (SEQ ID NO:1) |
| ④ | TRAV11-02 | TRAJ18-01 | VVGDRGSALGRLH (SEQ ID NO:2) |
| ⑤ | TRAV8-1-01 / TRAV8D-1-01 | TRAJ42-01 | CYPIFWRKQCKAN (SEQ ID NO:9) |

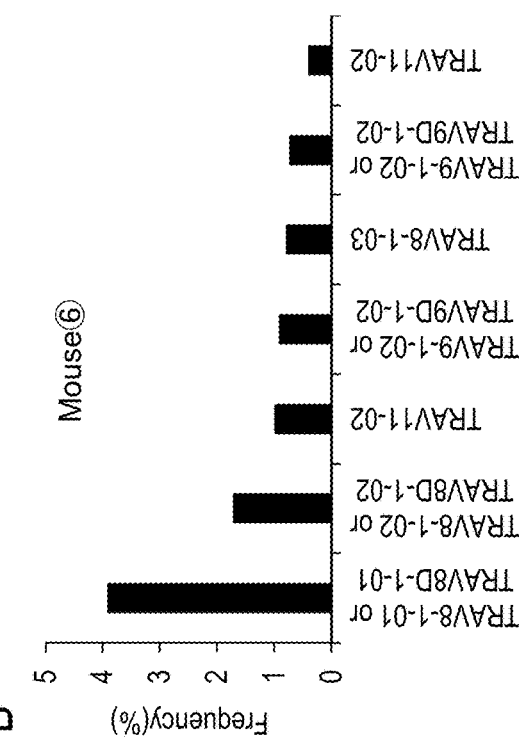

B Mouse ⑥

| | V-Gene and allele | J-Gene and allele | CDR-3 |
|---|---|---|---|
| ① | TRAV8-1-01 / TRAV8D-1-01 | TRAJ42-01 | ATLYSGGSNAKLT (SEQ ID NO:1) |
| ② | TRAV8-1-02 / TRAV8D-1-02 | TRAJ42-01 | ATLYSGGSNAKLT (SEQ ID NO:1) |
| ③ | TRAV11-02 | TRAJ18-01 | VVGDRGSALGRLH (SEQ ID NO:2) |
| ④ | TRAV9-1-02 / TRAV9D-1-02 | TRAJ7-01 | AVSARYSNNRLT (SEQ ID NO:10) |
| ⑤ | TRAV8-1-03 | TRAJ42-01 | ATLYSGGSNAKLT (SEQ ID NO:1) |

Fig. 15
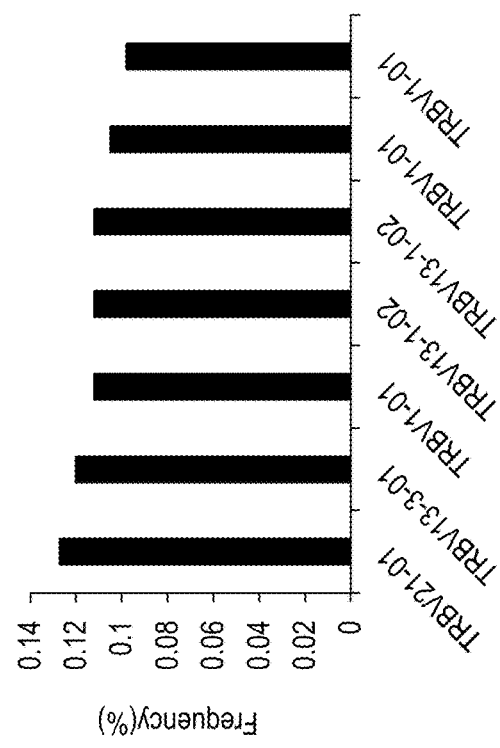
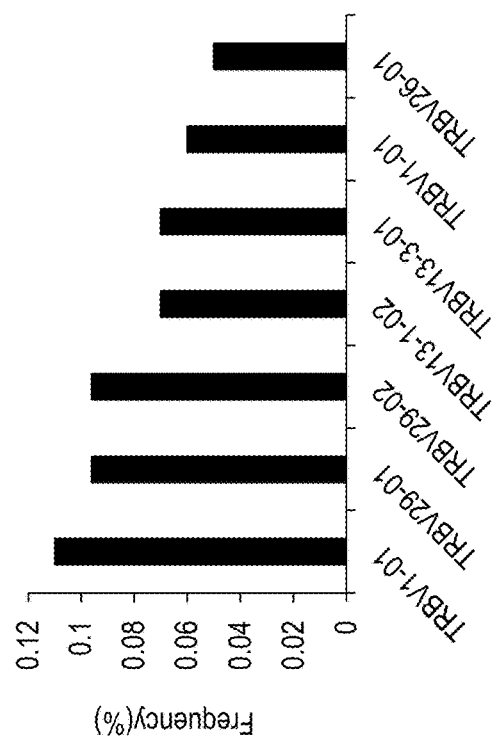

Fig. 16
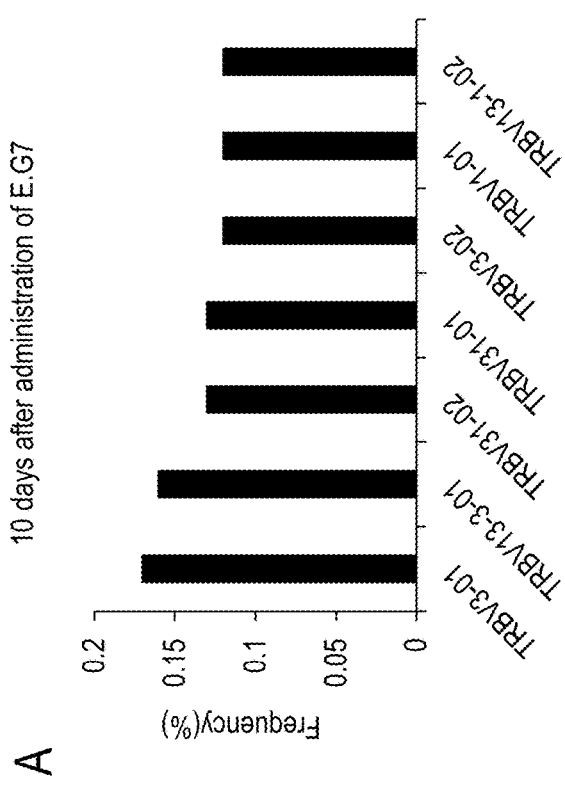
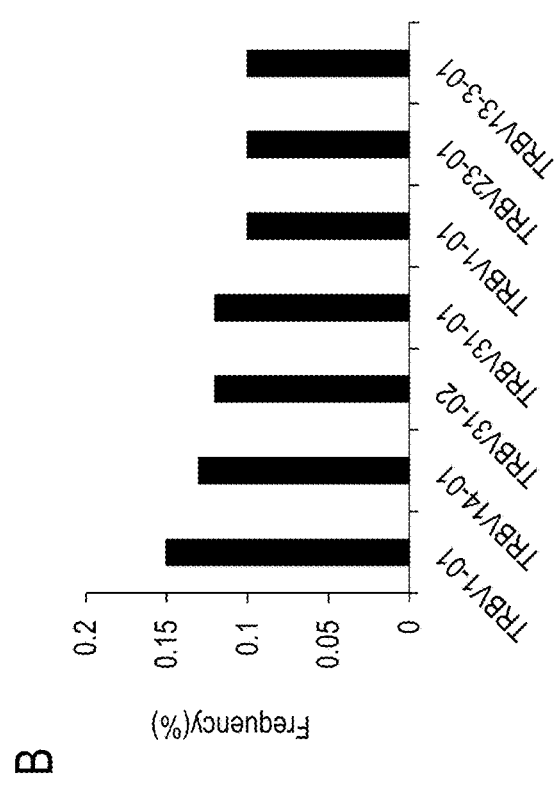

Fig. 21
A
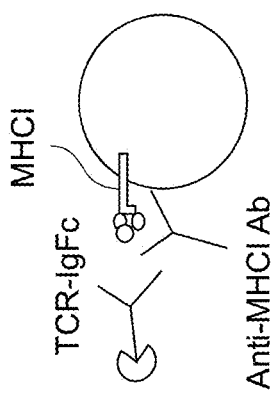
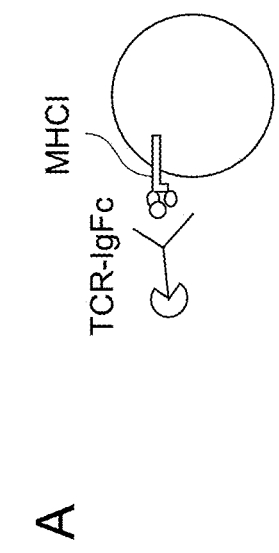
B
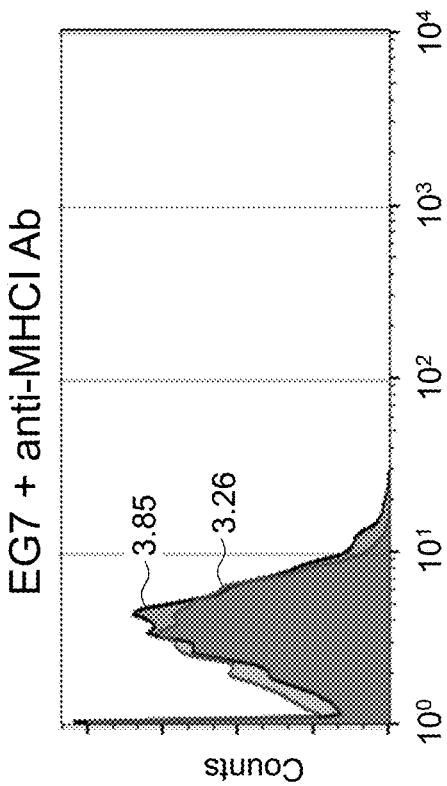
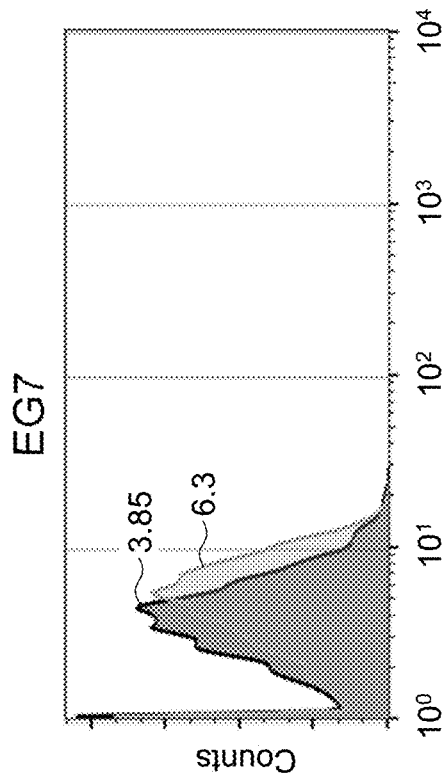

Fig. 24
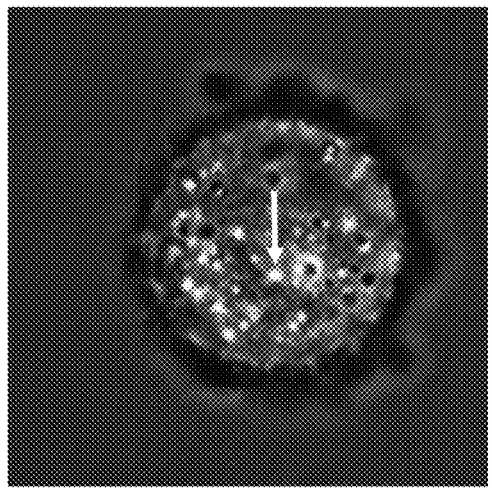
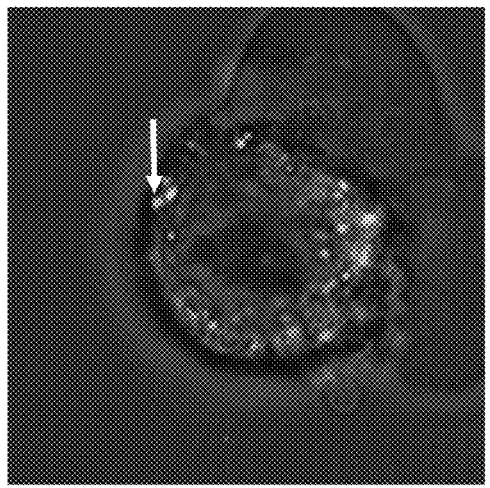
A  hTRAV21-CDR3-IgFc
   +MHC I
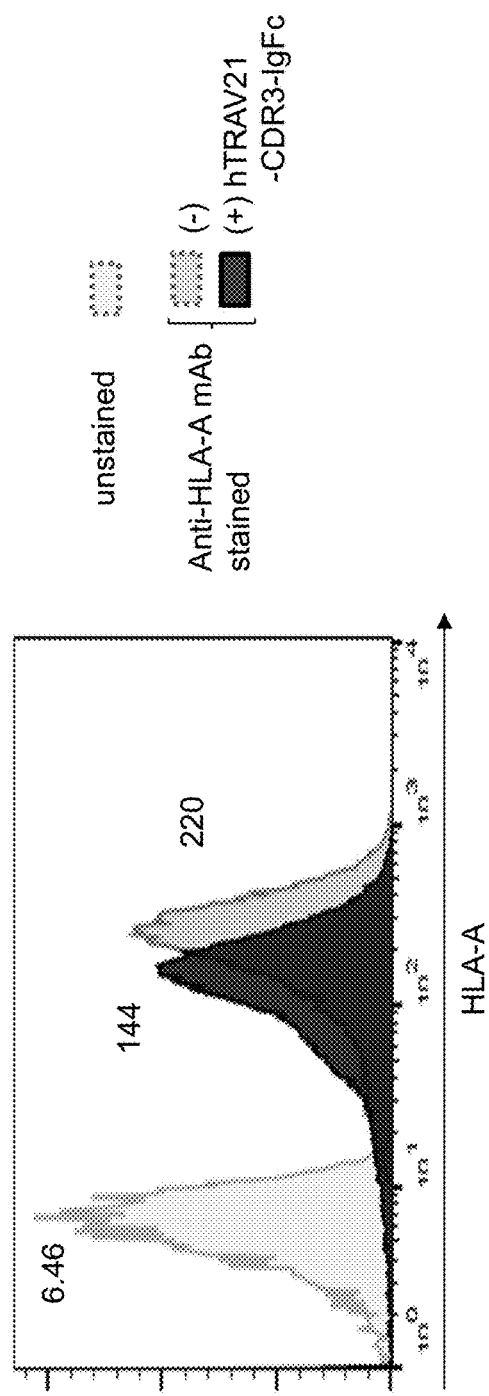
B

Fig. 30

|    | TCR-Ig treated | None |
|----|----------------|------|
| 1. | 1125           | 1769 |
| 2. | 927            | 1738 |
| 3. | 429            | 888  |

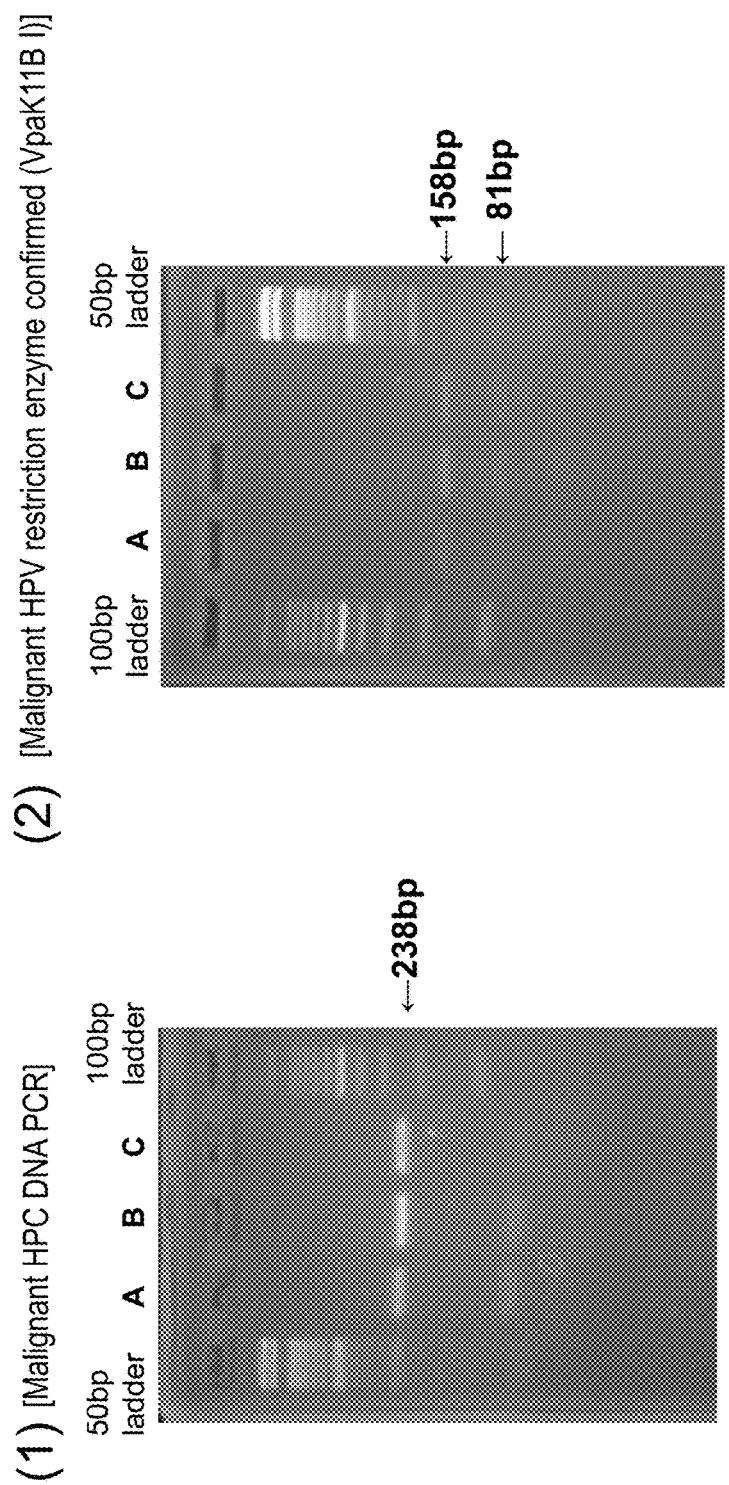
Fig. 34 Cervical cancer sample: A, B    Unknown sample: C

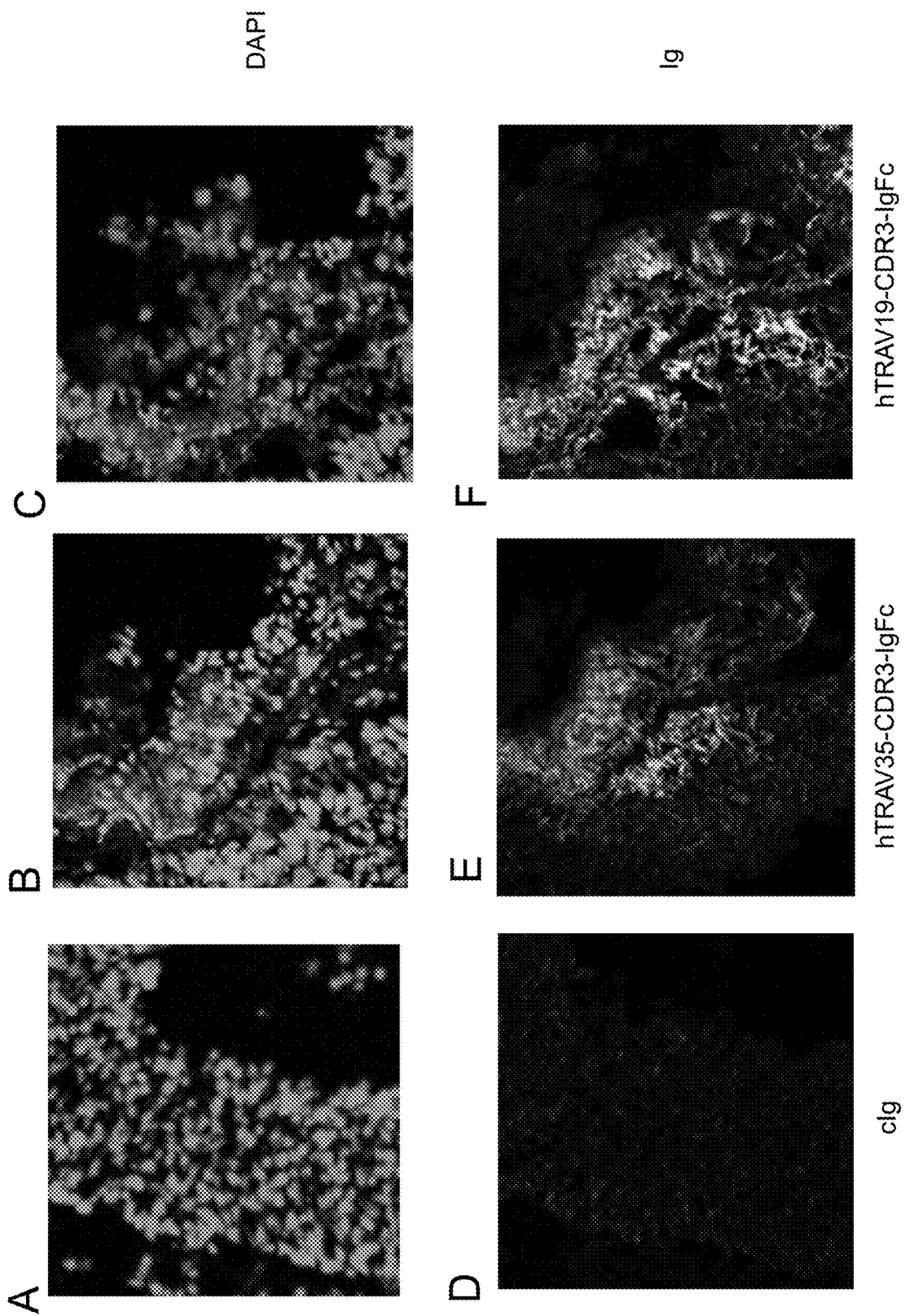

SEQUENCE LISTING

```
<160> NUMBER OF SEQ ID NOS: 33

<210> SEQ ID NO 1
<211> LENGTH: 13
<212> TYPE: PRT
<213> ORGANISM: Artificial
<220> FEATURE:
<223> OTHER INFORMATION: Synthetic

<400> SEQUENCE: 1

Ala Thr Leu Tyr Ser Gly Gly Ser Asn Ala Lys Leu Thr
1               5                   10

<210> SEQ ID NO 2
<211> LENGTH: 13
<212> TYPE: PRT
<213> ORGANISM: Artificial
<220> FEATURE:
```

```
<223> OTHER INFORMATION: Synthetic

<400> SEQUENCE: 2

Val Val Gly Asp Arg Gly Ser Ala Leu Gly Arg Leu His
1               5                   10

<210> SEQ ID NO 3
<211> LENGTH: 10
<212> TYPE: PRT
<213> ORGANISM: Artificial
<220> FEATURE:
<223> OTHER INFORMATION: Synthetic

<400> SEQUENCE: 3

Ala Ala Glu Thr Gly Gly Tyr Lys Val Val
1               5                   10

<210> SEQ ID NO 4
<211> LENGTH: 11
<212> TYPE: PRT
<213> ORGANISM: Artificial
<220> FEATURE:
<223> OTHER INFORMATION: Synthetic

<400> SEQUENCE: 4

Ile Val Thr Val Gln Gly Gly Arg Ala Leu Ile
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic

<400> SEQUENCE: 5

Val Trp Trp Gly Ile Glu Val Gln Pro Gly Gly Cys
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic

<400> SEQUENCE: 6

Ala Ala Ser Ile Gly Ser Ser Gly Gln Lys Leu Val
1               5                   10

<210> SEQ ID NO 7
<211> LENGTH: 11
<212> TYPE: PRT
<213> ORGANISM: Artificial
<220> FEATURE:
<223> OTHER INFORMATION: Synthetic

<400> SEQUENCE: 7

Ala Ala Ser Arg Asn Ser Asn Asn Arg Ile Phe
1               5                   10

<210> SEQ ID NO 8
<211> LENGTH: 12
<212> TYPE: PRT
<213> ORGANISM: Artificial
<220> FEATURE:
<223> OTHER INFORMATION: Synthetic
```

<400> SEQUENCE: 8

Ala Ala Ser Glu Asn Asn Tyr Ala Gln Gly Leu Thr
1               5                   10

<210> SEQ ID NO 9
<211> LENGTH: 13
<212> TYPE: PRT
<213> ORGANISM: Artificial
<220> FEATURE:
<223> OTHER INFORMATION: Synthetic

<400> SEQUENCE: 9

Cys Tyr Pro Ile Phe Trp Arg Lys Gln Cys Lys Ala Asn
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic

<400> SEQUENCE: 10

Ala Val Ser Ala Arg Tyr Ser Asn Asn Arg Leu Thr
1               5                   10

<210> SEQ ID NO 11
<211> LENGTH: 13
<212> TYPE: PRT
<213> ORGANISM: Artificial
<220> FEATURE:
<223> OTHER INFORMATION: Synthetic

<400> SEQUENCE: 11

Ala Ser Ser Gln Ser Gly Ser Tyr Asn Ser Pro Leu Tyr
1               5                   10

<210> SEQ ID NO 12
<211> LENGTH: 12
<212> TYPE: PRT
<213> ORGANISM: Artificial
<220> FEATURE:
<223> OTHER INFORMATION: Synthetic

<400> SEQUENCE: 12

Ala Ser Ser Trp Asp Arg Gly Arg Asn Thr Leu Tyr
1               5                   10

<210> SEQ ID NO 13
<211> LENGTH: 12
<212> TYPE: PRT
<213> ORGANISM: Artificial
<220> FEATURE:
<223> OTHER INFORMATION: Synthetic

<400> SEQUENCE: 13

Thr Cys Ser Val Gly Thr Thr Asn Thr Glu Val Phe
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic

```
<400> SEQUENCE: 14

Ala Ser Ser Ala Pro Gly Ala Pro Arg His Pro Val
1               5                   10

<210> SEQ ID NO 15
<211> LENGTH: 12
<212> TYPE: PRT
<213> ORGANISM: Artificial
<220> FEATURE:
<223> OTHER INFORMATION: Synthetic

<400> SEQUENCE: 15

Thr Cys Ser Ala Asp Arg Gly Ala Glu Thr Leu Tyr
1               5                   10

<210> SEQ ID NO 16
<211> LENGTH: 12
<212> TYPE: PRT
<213> ORGANISM: Artificial
<220> FEATURE:
<223> OTHER INFORMATION: Synthetic

<400> SEQUENCE: 16

Ala Ser Ser Leu Arg Glu Gly Gln Asn Thr Leu Tyr
1               5                   10

<210> SEQ ID NO 17
<211> LENGTH: 13
<212> TYPE: PRT
<213> ORGANISM: Artificial
<220> FEATURE:
<223> OTHER INFORMATION: Synthetic

<400> SEQUENCE: 17

Ala Ser Ser Arg Asp Trp Gly Tyr Ser Tyr Glu Gln Tyr
1               5                   10

<210> SEQ ID NO 18
<211> LENGTH: 12
<212> TYPE: PRT
<213> ORGANISM: Artificial
<220> FEATURE:
<223> OTHER INFORMATION: Synthetic

<400> SEQUENCE: 18

Ala Ser Ser Pro Leu Gly Gly Ser Tyr Glu Gln Tyr
1               5                   10

<210> SEQ ID NO 19
<211> LENGTH: 13
<212> TYPE: PRT
<213> ORGANISM: Artificial
<220> FEATURE:
<223> OTHER INFORMATION: Synthetic

<400> SEQUENCE: 19

Ala Ser Ser Trp Asp Trp Gly Asn Tyr Ala Glu Gln Phe
1               5                   10

<210> SEQ ID NO 20
<211> LENGTH: 9
<212> TYPE: PRT
<213> ORGANISM: Artificial
<220> FEATURE:
<223> OTHER INFORMATION: Synthetic

<400> SEQUENCE: 20
```

```
Ala Trp Asp Phe Ala Glu Thr Leu Tyr
1               5
```

```
<210> SEQ ID NO 21
<211> LENGTH: 9
<212> TYPE: PRT
<213> ORGANISM: Artificial
<220> FEATURE:
<223> OTHER INFORMATION: Synthetic

<400> SEQUENCE: 21

Thr Cys Ser Ala Gly Tyr Glu Gln Tyr
1               5
```

```
<210> SEQ ID NO 22
<211> LENGTH: 13
<212> TYPE: PRT
<213> ORGANISM: Artificial
<220> FEATURE:
<223> OTHER INFORMATION: Synthetic

<400> SEQUENCE: 22

Ala Ser Ser Phe Arg Asp Leu Asn Tyr Ala Glu Gln Phe
1               5                   10
```

```
<210> SEQ ID NO 23
<211> LENGTH: 10
<212> TYPE: PRT
<213> ORGANISM: Artificial
<220> FEATURE:
<223> OTHER INFORMATION: Synthetic

<400> SEQUENCE: 23

Ala Trp Ser Leu Val Gly Val Glu Gln Tyr
1               5                   10
```

```
<210> SEQ ID NO 24
<211> LENGTH: 10
<212> TYPE: PRT
<213> ORGANISM: Artificial
<220> FEATURE:
<223> OTHER INFORMATION: Synthetic

<400> SEQUENCE: 24

Ala Ser Ser Pro Gln Gly Tyr Glu Gln Tyr
1               5                   10
```

```
<210> SEQ ID NO 25
<211> LENGTH: 10
<212> TYPE: PRT
<213> ORGANISM: Artificial
<220> FEATURE:
<223> OTHER INFORMATION: Synthetic

<400> SEQUENCE: 25

Ala Trp Arg Gly Gly Ala Gly Gln Leu Tyr
1               5                   10
```

```
<210> SEQ ID NO 26
<211> LENGTH: 11
<212> TYPE: PRT
<213> ORGANISM: Artificial
<220> FEATURE:
<223> OTHER INFORMATION: Synthetic

<400> SEQUENCE: 26
```

Ala Ser Ser Asp Asp Gly Gln Asn Thr Leu Tyr
1               5                   10

<210> SEQ ID NO 27
<211> LENGTH: 13
<212> TYPE: PRT
<213> ORGANISM: Artificial
<220> FEATURE:
<223> OTHER INFORMATION: Synthetic

<400> SEQUENCE: 27

Thr Cys Ser Ala Ala Gly Ala Phe Tyr Ala Glu Gln Phe
1               5                   10

<210> SEQ ID NO 28
<211> LENGTH: 11
<212> TYPE: PRT
<213> ORGANISM: Artificial
<220> FEATURE:
<223> OTHER INFORMATION: Synthetic

<400> SEQUENCE: 28

Ala Ser Ser Leu Gly Asp Gln Asn Thr Leu Tyr
1               5                   10

<210> SEQ ID NO 29
<211> LENGTH: 12
<212> TYPE: PRT
<213> ORGANISM: Artificial
<220> FEATURE:
<223> OTHER INFORMATION: Synthetic

<400> SEQUENCE: 29

Ala Ser Ser Gly Thr Ala Ser Ala Glu Thr Leu Tyr
1               5                   10

<210> SEQ ID NO 30
<211> LENGTH: 11
<212> TYPE: PRT
<213> ORGANISM: Artificial
<220> FEATURE:
<223> OTHER INFORMATION: Synthetic

<400> SEQUENCE: 30

Cys Ser Ala Asp Arg Asn Thr Gly Gln Leu Tyr
1               5                   10

<210> SEQ ID NO 31
<211> LENGTH: 11
<212> TYPE: PRT
<213> ORGANISM: Artificial
<220> FEATURE:
<223> OTHER INFORMATION: Synthetic

<400> SEQUENCE: 31

Ala Ser Ser Leu Gly Gly Ser Lys His Leu Val
1               5                   10

<210> SEQ ID NO 32
<211> LENGTH: 29
<212> TYPE: DNA
<213> ORGANISM: Artificial
<220> FEATURE:
<223> OTHER INFORMATION: Primer

<400> SEQUENCE: 32
cggaattcat gcacagcctc ctggggttg                                    29

```
<210> SEQ ID NO 33
<211> LENGTH: 31
<212> TYPE: DNA
<213> ORGANISM: Artificial
<220> FEATURE:
<223> OTHER INFORMATION: Primer

<400> SEQUENCE: 33
gaagatctag gttctgggtt ctggatgttt g                              31
```

NATURAL KILLER CELL FUNCTION ENHANCER

CROSS-REFERENCE TO RELATED APPLICATIONS

This application is a 371 of PCT/JP2017/028490, filed Aug. 4, 2017, which claims benefit of Japanese Patent Application No. 2016-154742 filed on Aug. 5, 2016.

TECHNICAL FIELD

The present invention relates to treatment or diagnosis of cancer or infectious disease.

BACKGROUND ART

As cancer treatments, surgical treatments, radiation treatments and chemotherapies are basically known and these are called as major three therapies.

In recent years, in addition to these three major therapies, immunotherapies have been getting attention as a fourth therapy. Examples of immunotherapies include: a method for activating antitumor immunity, which attacks cancer by use of immunocompetence (immune cells) originally possessed by a living body; and a method for blocking immunosuppressive reaction of cancer cells. The former treatments include immunological enhancement by cytokine, enhancement of killer T-cells or NK cells, dendritic cell vaccine therapy and peptide vaccine therapy; and the latter treatments include immune checkpoint inhibition therapy.

As described above, killer T-cells or NK cells are used as a method for activating antitumor immunity. Since NK cells can directly attack cancer, it is known that NK cells are useful in cancer treatment such as antimetastatic (see Non-Patent Literature 1).

T-cells recognize MHCs (major histocompatibility complex) and peptides. T-cells cannot recognize them if MHCs are not expressed in target cells. Meanwhile, NK cells recognize the non-existence of MHCs, and then work. NK cells cannot recognize that MHCs are expressed in target cells. Normal cell usually express MHC molecules, so they cannot become targets of NK cells.

Only NK cells, which do not target cells having an MHC expressed therein, cannot provide a sufficient immunotherapic effect on cancer; and in recent years, researches have been made on use of T-cells capable of specifically recognizing cancer and intensive researches have been made on methods for inducing killer T-cells.

In addition, researches for specifying cancer-specific antigens have been also advanced, and cancer peptide therapy or dendritic cell therapy has been developed.

T-cell receptors (TCR) perform an important role on the action of T-cells; and recent years have witnessed the development of a method for analyzing a T-cell receptor repertoire of a T-cell receptor of a patient with a certain disease and identifying a disease-specific T-cell receptor. Further, a method that uses a protein having a fragment of a T-cell receptor has been also reported (see Patent Literature 1).

As is the case with cancer, for infectious diseases, in particular, emerging/reemerging infectious diseases, for which treatments have not been established, there are expectations on immunotherapies using abilities of NK cells or T-cells for eliminating infected cells.

CITATION LIST

Patent Literature

Patent Literature 1: JP Patent Publication (Kohyo) No. 2007-513326A

Non Patent Literature

Non Patent Literature 1: Ogasawara K. et al., Clin J Immunol; 25(6): 534-40

SUMMARY OF INVENTION

Technical Problem

The present invention has an object of providing a treatment and a diagnosis of cancer or infectious diseases using a recognition mechanism of T-cell receptors. Specifically, a T-cell receptor chimeric protein is allows to bind to an MHC complex of a target cell and is incorporated into the target cell, thereby enabling cells to be efficiently destroyed. That is, imparting a magnetic substance or a drug to a T-cell receptor chimeric protein or a protein capable of recognizing a T-cell receptor chimeric protein promotes target cell-selective incorporation of the drug into cytoplasm, and use of this enables cells to be destroyed. Further, the present invention provides a method for enhancing the function of NK cells in two ways. One is to provide a method for allowing NK cells to easily recognize target cells by inducing down-modulation of MHC complexes on the target cells by T-cell receptor chimeric proteins. The other is to provide a method for enhancing the function of NK cells, which imparts an MHC class I molecule recognition mechanism to NK cells thereby to the NK cells to kill or damage target cells (such as cancer cells of infected cells infected with a pathogen such as bacteria or viruses causative of an infectious disease) having an MHC class I molecule expressed therein.

Solution to Problem

It has been reported that NK cells can be used for cancer metastasis suppression, and for elimination of infected cells infected with a pathogen such as bacteria or viruses causative of an infection. Meanwhile, NK cells are unable to recognize cancer cells or infected cells having MHC class I molecules expressed therein, and thus, they have been thought to have a limitation in using for treatments of cancer cells or elimination of infected cells.

The present inventors have made intensive studies on methods for treating cancer or infectious diseases using NK cells, and they have found that use of a recognition mechanism of a T-cell receptor enhances the function of NK cells and imparts an ability to kill or damage cancer cells or infected cells having MHC class I molecules expressed therein.

That is, co-existence of target cells with a T-cell receptor chimeric protein being a fusion protein of a T-cell receptor variable region and an immunoglobulin Fc region enables the T-cell receptor variable region of the T-cell receptor chimeric protein to bind to an MHC class I molecule of cancer cells or infected cells, then inducing two types of reactions. One is to induce down-modulation of MHC class I molecules indicative of an antigen and reduce the expression. Down-modulation of MHC class I enables NK cells to recognize target cells and to kill or damage them. The other is to allow the immunoglobulin Fc region of the T-cell receptor chimeric protein to bind to Fc receptors expressed in NK cells, whereby the NK cells bind to cancer cells or infected cells having MHC class I molecules expressed therein thereby to enable the NK cells to recognize the cancer cells or infected cells and to kill or damage them.

The present inventors have named an activity of an NK cell for killing or wounding a cancer cell or infected cell having an MHC class I molecule expressed therein, which is given by a T-cell receptor chimeric protein as T-cell receptor chimeric protein-dependent cellular cytotoxicity (TDCC).

Specifically, the present invention is described below.

[1] An NK cell function enhancer comprising, as an active ingredient, a T-cell receptor chimeric protein being a fusion protein of a T-cell receptor variable region capable of recognizing a cancer-specific antigen and an immunoglobulin Fc region, wherein the T-cell receptor chimeric protein binds to an MHC molecular complex of a cancer cell to reduce the expression of an MHC class I molecular complex and the cancer cell is killed or damaged by recognition of an NK cell.

[2] An NK cell function enhancer comprising, as an active ingredient, a T-cell receptor chimeric protein being a fusion protein of a T-cell receptor variable region capable of recognizing a cancer-specific antigen and an immunoglobulin Fc region, wherein the enhancer is for imparting a recognition function of a cancer cell expressing an MHC class I molecule to an NK cell to kill or damage the cancer cell by TDCC (T-cell receptor chimeric protein-dependent cellular cytotoxicity) activity.

[3] The NK cell function enhancer according to [1] or [2], wherein the T-cell receptor chimeric protein comprises all of the T-cell receptor variable region and CDR3, and a J region.

[4] The NK cell function enhancer according to any of [1] to [3], wherein the T-cell receptor variable region is an α chain and/or β chain of the T-cell receptor.

[5] The NK cell function enhancer according to [4], wherein the T-cell receptor variable region is an α chain of the T-cell receptor.

[6] The NK cell function enhancer according to any of [1] to [5], wherein the immunoglobulin Fc region is an Fc region of IgG.

[7] The NK cell function enhancer according to any of [1] to [6], wherein the enhancer is a dimer consisting of two fusion proteins of the T-cell receptor variable region and the immunoglobulin Fc region and the two proteins are bonded to each other by disulfide bond.

[8] The NK cell function enhancer according to any of [1] to [7], wherein the T-cell receptor binds to an MHC class I molecule.

[9] A method for detecting a cancer cell comprising the steps of:
bringing a labelled T-cell receptor chimeric protein, which is a T-cell receptor chimeric protein being a fusion protein of: a T-cell receptor variable region capable of recognizing a cancer-specific antigen; and an immunoglobulin Fc region, into contact with a cell collected from a biological sample of a subject; and
determining that a target cell is present in the subject when the T-cell receptor chimeric protein binds to the cell collected from the biological sample of the subject.

[10] A reagent for cancer detection comprising a labelled T-cell receptor chimeric protein, which is a T-cell receptor chimeric protein being a fusion protein of a T-cell receptor chimeric protein capable of recognizing a cancer-specific antigen and an immunoglobulin Fc region.

[11] A method for producing a T-cell receptor chimeric protein being a fusion protein of a T-cell receptor variable region and an immunoglobulin Fc region, the method comprising the steps of:
cloning a DNA molecule encoding a cancer antigen-specific T-cell receptor capable of recognizing a cancer-specific antigen from a T-cell collected from a cancer patient;
ligating the DNA molecule with a DNA molecule encoding the immunoglobulin Fc region and introducing the ligated product into an expression vector; and
introducing and expressing the expression vector into a host cell.

[12] The method for producing a T-cell receptor chimeric protein being a fusion protein of a T-cell receptor variable region and an immunoglobulin Fc region according to [11], the method comprising the steps of:
analyzing a repertoire of the T-cell receptor possessed by a cancer patient by use of a T-cell collected from the cancer patient;
cloning a DNA molecule encoding a T-cell receptor with a high frequency in the cancer patient as a specific T-cell receptor highly specific to the cancer;
ligating the DNA molecule with a DNA molecule encoding the immunoglobulin Fc region and introducing the ligated product into an expression vector; and introducing and expressing the expression vector into a host cell.

[13] A complex comprising a T-cell receptor chimeric protein capable of recognizing a cancer-specific antigen, and an NK cell receptor.

[14] A method for producing a complex of a T-cell receptor chimeric protein and an NK cell, comprising the step of bringing a T-cell receptor chimeric protein capable of recognizing in vitro a cancer-specific antigen into contact with an NK cell.

[15] An NK cell function enhancer comprising, as an active ingredient, a T-cell receptor chimeric protein being a fusion protein of a T-cell receptor variable region capable of recognizing an antigen specific to a pathogen causative of an infectious disease, and an immunoglobulin Fc region, wherein the T-cell receptor chimeric protein binds to an MHC class I molecular complex of an infected cell infected with the pathogen causative of the infectious disease to reduce the expression of an MHC molecular complex and the infected cell is killed or damaged by recognition of an NK cell.

[16] An NK cell function enhancer comprising, as an active ingredient, a T-cell receptor chimeric protein being a fusion protein of a T-cell receptor variable region capable of recognizing an antigen specific to a pathogen causative of an infectious disease, and an immunoglobulin Fc region, wherein the enhancer is for imparting a recognition function of an infected cell infected with the pathogen causative of the infectious disease, which expresses an MHC class I molecule, to an NK cell, and killing or damaging the infected cell by TDCC (T-cell receptor chimeric protein-dependent cellular cytotoxicity) activity.

[17] The NK cell function enhancer according to [15] or [16], wherein the T-cell receptor chimeric protein comprises all of the T-cell receptor variable region and CDR3, and a J region.

[18] The NK cell function enhancer according to any of [15] to [17], wherein the T-cell receptor variable region is an α chain and/or β chain of the T-cell receptor.

[19] The NK cell function enhancer according to [18], wherein the T-cell receptor variable region is an α chain of the T-cell receptor.
[20] The NK cell function enhancer according to any of [15] to [19], wherein the immunoglobulin Fc region is an Fc region of IgG.
[21] The NK cell function enhancer according to any of [15] to [20], wherein the enhancer is a dimer consisting of two fusion proteins of the T-cell receptor variable region and the immunoglobulin Fc region and the two proteins are bonded to each other by disulfide bond.
[22] The NK cell function enhancer according to any of [15] to [21], wherein the T-cell receptor binds to an MHC class I molecule.
[23] A method for detecting an infected cell infected with a pathogen causative of an infection comprising the steps of:
bringing a labelled T-cell receptor chimeric protein, which is a T-cell receptor chimeric protein being a fusion protein of: a T-cell receptor variable region capable of recognizing an antigen specific to a pathogen causative of an infection; and an immunoglobulin Fc region, into contact with a cell collected from a biological sample of a subject; and
determining that a target cell is present in the subject when the T-cell receptor chimeric protein binds to the cell collected from the biological sample of the subject.
[24] A reagent for detecting an infected cell comprising a labelled T-cell receptor chimeric protein, which is a T-cell receptor chimeric protein being a fusion protein of a T-cell receptor chimeric protein capable of recognizing an antigen specific to a pathogen causative of an infection, and an immunoglobulin Fc region.
[25] A method for producing a T-cell receptor chimeric protein being a fusion protein of a T-cell receptor variable region and an immunoglobulin Fc region, the method comprising the steps of:
cloning a DNA molecule encoding a pathogen antigen-specific T-cell receptor capable of recognizing an antigen specific to a pathogen causative of an infection from a T-cell collected from a patient with the infection;
ligating the DNA molecule with a DNA molecule encoding the immunoglobulin Fc region and introducing the ligated product into an expression vector; and
introducing and expressing the expression vector into a host cell.
[26] The method for producing a T-cell receptor chimeric protein being a fusion protein of a T-cell receptor variable region and an immunoglobulin Fc region according to [25], the method comprising the steps of:
analyzing a repertoire of the T-cell receptor possessed by the patient with the infection by use of a T-cell collected from the patient with the infection;
cloning a DNA molecule encoding a T-cell receptor with a high frequency in the patient with the infection as a specific T-cell receptor highly specific to the infection;
ligating the DNA molecule with a DNA molecule encoding the immunoglobulin Fc region and introducing the ligated product into an expression vector; and
introducing and expressing the expression vector into a host cell.
[27] A complex comprising a T-cell receptor chimeric protein capable of recognizing an antigen specific to a pathogen causative of an infection, and an NK cell receptor.
[28] A method for producing a complex of a T-cell receptor chimeric protein and an NK cell, comprising the step of bringing a T-cell receptor chimeric protein capable of recognizing in vitro an antigen specific to a pathogen causative of an infection and an NK cell into contact with each other.

[29] An MHC molecular complex down-modulating agent comprising, as an active ingredient, a T-cell receptor chimeric protein being a fusion protein of a T-cell receptor variable region and an immunoglobulin Fc region, wherein the agent binds to an MHC molecular complex of a target cell to reduce the expression of an MHC class I molecular complex.
[30] The MHC molecular complex down-modulating agent according to [29], wherein the T-cell receptor chimeric protein comprises all of the T-cell receptor variable region and CDR3, and a J region.
[31] The MHC molecular complex down-modulating agent according to [29] or [30], wherein the T-cell receptor variable region is an α chain and/or β chain of the T-cell receptor.
[32] The MHC molecular complex down-modulating agent according to [31], wherein the T-cell receptor variable region is an α chain of the T-cell receptor.
[33] The MHC molecular complex down-modulating agent according to any one of [29] to
[32], wherein the immunoglobulin Fc region is an Fc region of IgG.
[34] The MHC molecular complex down-modulating agent according to any of [29] to [33], wherein the agent is a dimer of two fusion proteins of the T-cell receptor variable region and the immunoglobulin Fc region and the two proteins are bonded to each other by disulfide bond.
[35] The MHC molecular complex down-modulating agent according to any of [29] to [34], wherein the T-cell receptor binds to an MHC class I molecule.
[36] The MHC molecular complex down-modulating agent according to any of [29] to [35], wherein the target cell is a cancer cell or an infected cell infected with a pathogen causative of an infection.
[37] A method for specifying a cancer-specific T-cell receptor α chain variable region, the method comprising the steps of:
identifying a repertoire of a T-cell receptor α chain variable region of a lymphocyte in a cancer tissue of a cancer patient and a repertoire of a T-cell receptor α chain of a lymphocyte in peripheral blood of the cancer patient; and
determining, as a cancer-specific T-cell receptor α chain variable region, a T-cell receptor α chain variable region that is present in the lymphocyte in the cancer tissue two-fold or more in abundance than in the lymphocyte in the peripheral blood.
[38] The method for specifying a cancer-specific T-cell receptor α chain variable region according to [37], the method comprising the steps of:
specifying a cancer-specific T-cell receptor α chain variable region in a plurality of cancer patients; and
determining, as a cancer-specific human common T-cell receptor α chain variable region, a T-cell receptor α chain variable region that is present in a lymphocyte in a cancer tissue two-fold or more in abundance than in a lymphocyte in peripheral blood.
[39] A method for specifying a cancer-specific T-cell receptor α chain variable region, the method comprising the steps of:
identifying a repertoire of a T-cell receptor α chain variable region of a lymphocyte in a cancer tissue of a cancer patient and a repertoire of a T-cell receptor α chain of a lymphocyte in peripheral blood of a healthy subject; and
determining, as a cancer-specific T-cell receptor α chain variable region, a T-cell receptor α chain variable region that is present in the lymphocyte in the cancer tissue two-fold or more in abundance than in the lymphocyte in peripheral blood of the healthy subject.

[40] The method for specifying a cancer-specific T-cell receptor α chain variable region according to [39], wherein the method uses a mixture of lymphocytes in cancer tissues of a plurality of cancer patients and a mixture of lymphocytes in peripheral blood of a plurality of healthy subjects to determine, as a cancer-specific human common T-cell receptor α chain variable region, a T-cell receptor α chain variable region that is present in the lymphocytes in the cancer tissues two-fold or more in abundance than in the lymphocytes in peripheral blood of the healthy subjects.

[41] A method for specifying a cancer-specific T-cell receptor α chain variable region, comprising determining, as a cancer-specific human common T-cell receptor α chain variable region, both of a cancer-specific T-cell receptor α chain variable region specified by the method of [38] and a cancer-specific T-cell receptor α chain variable region specified by the method of [40].

[42] The method for specifying a cancer-specific T-cell receptor α chain variable region according to any of [37] to [41], wherein the cancer is squamous cancer.

[43] The method for specifying a cancer-specific T-cell α chain variable region according to any of [37] to [41], wherein the cancer is cervical cancer or lung cancer.

[44] A cancer-specific human common T-cell receptor α chain variable region of cervical cancer comprising a T-cell receptor α chain variable region coded by any of T-cell receptor α chain variable region gene selected from the group consisting of TRAV1-1-01, TRAV1-1-02, TRAV21-02, TRAV22-01, TRAV1-2-01, TRAV12-2-03, TRAV39-01, TRAV2-01, TRAV21-01, TRAV12-1-01, TRAV1-2-01 and TRAV38-2/DV8-01.

[45] A cancer-specific human common T-cell receptor α chain variable region of cervical cancer comprising a T-cell receptor α chain variable region having a CDR3 region having a consensus frame represented by AVR—(x=1 to 6)—G—(x=1 to 3)—KL(I)/(T).

[46] A cancer-specific human common T-cell receptor α chain variable region of lung cancer comprising a T-cell receptor α chain variable region coded by any of T-cell receptor α chain variable region gene selected from the group consisting of TRAV12-1-01, TRAV16-01, TRAV19-01, TRAV22-01, TRAV35-02, TRAV17-01, TRAV9-2-02 and TRAV13-1-01.

[47] The NK cell function enhancer according to any of [1] to [8] and [15] to [22], wherein the T-cell receptor variable region is a T-cell receptor variable region specified by a method of any of [37] to [42].

[48] The NK cell function enhancer according to [47], wherein the T-cell receptor variable region is a cancer-specific human common T-cell receptor α chain variable region for cervical cancer coded by any of T-cell receptor α chain variable region gene selected from the group consisting of TRAV1-1-01, TRAV1-1-02, TRAV21-02, TRAV22-01, TRAV1-2-01, TRAV12-2-03, TRAV39-01, TRAV2-01, TRAV21-01, TRAV12-1-01, TRAV1-2-01 and TRAV38-2/DV8-01.

[49] The NK cell function enhancer according to [47] or [48], wherein the T-cell receptor variable region is a cancer-specific human common T-cell receptor α chain variable region for cervical cancer having a CDR3 region having a consensus frame represented by AVR—(x=1 to 6)—G—(x=1 to 3)—KL(I)/(T).

[50] The NK cell function enhancer according to [47], wherein the T-cell receptor variable region is a cancer-specific human common T-cell receptor α chain variable region for lung cancer coded by any of T-cell receptor α chain variable region gene selected from the group consisting of TRAV12-1-01, TRAV16-01, TRAV19-01, TRAV22-01, TRAV35-02, TRAV17-01, TRAV9-2-02 and TRAV13-1-01.

[51] The MHC molecular complex down-modulating agent according to any of [29] to [36], wherein the T-cell receptor variable region is a T-cell receptor variable region specified by the method according to any of [37] to [43].

[52] The MHC molecular complex down-modulating agent according to [51], wherein the T-cell receptor variable region is a cancer-specific human common T-cell receptor α chain variable region for cervical cancer coded by any of T-cell receptor α chain variable region gene selected from the group consisting of TRAV1-1-01, TRAV1-1-02, TRAV21-02, TRAV22-01, TRAV1-2-01, TRAV12-2-03, TRAV39-01, TRAV2-01, TRAV21-01, TRAV12-1-01, TRAV1-2-01 and TRAV38-2/DV8-01.

[53] The MHC molecular complex down-modulating agent according to [51] or [52], wherein the T-cell receptor variable region is a cancer-specific human common T-cell receptor α chain variable region for cervical cancer having a CDR3 region having a consensus frame represented by AVR—(x=1 to 6)—G—(x=1 to 3)—KL(I)/(T).

[54] The MHC molecular complex down-modulating agent according to [51], wherein the T-cell receptor variable region is a cancer-specific human common T-cell receptor α chain variable region for lung cancer coded by any of T-cell receptor α chain variable region gene selected from the group consisting of TRAV12-1-01, TRAV16-01, TRAV19-01, TRAV22-01, TRAV35-02, TRAV17-01, TRAV9-2-02 and TRAV13-1-01.

[55] A method for reducing the expression of an MHC complex, comprising the steps of:
including, as an active ingredient, a T-cell receptor chimeric protein being a fusion protein of a T-cell receptor variable region and an immunoglobulin Fc region;
binding to an MHC complex of a target cell; and
inducing the downmodulation of the MHC complex.

[56] A method for incorporating a T-cell receptor chimeric protein into a target cell, comprising the step of coupling the T-cell receptor chimeric protein with an MHC complex on the target cell.

[57] A method for breaking a cell comprising the steps of:
imparting a magnetic substance or a drug to a T-cell receptor chimeric protein or a protein capable of recognizing a T-cell receptor chimeric protein to promote target cell-selective incorporation of the drug into cytoplasm; and
breaking a cell thereby.

This specification includes part or all of the contents as disclosed in the specification and/or drawings of Japanese Patent Application No. 2016-154742, from which the priority for the present application is claimed.

Advantageous Effects of Invention

A T-cell receptor chimeric protein binds to an MHC class I molecule of a cancer cell or infected cell to induce down-modulation of the MHC class I molecule indicative of an antigen, thereby reducing the expression. Down-modulation of MHC class I enables NK cells to recognize target cells and to kill or damage them. In addition, an immunoglobulin Fc region of the T-cell receptor chimeric protein binds to an Fc receptor expressed in an NK cell, and this allows the NK cell to bind to a cancer cell or infected cell having an MHC class I molecule expressed therein; this imparts to the NK cell a function to recognize a cancer cell or an infected cell infected with a pathogen such as bacteria or viruses causative of an infection, wherein an MHC class I molecule is expressed, and a function to kill or damage the cancer cell or infected cell. That is, the T-cell receptor chimeric protein can enhance a function of NK cells to killing or damaging cancer cells or infected cells.

Further, the T-cell receptor chimeric protein can bind to cancer cells or infected cells having an MHC class I molecule expressed therein, and thus, it can be used to detect cancer cells or infected cells.

BRIEF DESCRIPTION OF DRAWINGS

FIG. 13 shows analytical results of TCR α chain of lymphocytes collected from mice 10 days after inoculation with E.G7 in TCR repertoire analysis.

FIG. 14 shows analytical results of TCR α chain of lymphocytes collected from mice 15 days after inoculation with E.G7 in TCR repertoire analysis.

FIG. 15 shows analytical results of TCR β chain of lymphocytes collected from naive mice in TCR repertoire analysis.

FIG. 16 shows analytical results of TCR β chain of lymphocytes collected from mice 10 days after inoculation with E.G7 in TCR repertoire analysis.

FIG. 21 shows results on detection of an MHC complex by a T-cell receptor chimeric protein.

FIG. 24 shows cell internalization of a T-cell receptor chimeric protein bound to an MHC molecule in a human cell; and down-modulation of an MHC complex by a T-cell receptor chimeric protein.

FIG. 30 shows a cancer metastasis suppressing effect by a T-cell receptor chimeric protein.

FIG. 33-1 shows consensus frames of CDR3 common to cervical cancer.

FIG. 33-2 shows frequencies of consensus frames of CDR3 common to cervical cancer.

FIG. 34 shows results in detecting HPV infection.

FIG. 37 show results in detecting lung cancer cells by a T-cell receptor chimeric protein.

DESCRIPTION OF EMBODIMENTS

Figure 1:
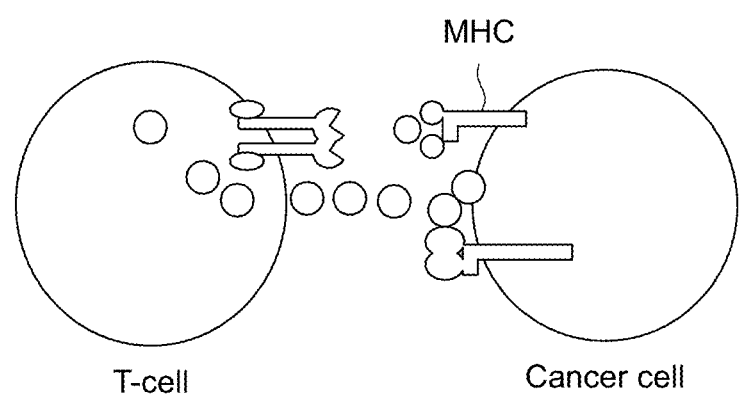
FIG. 1 shows a mechanism of T-cell for recognizing a cancer cell.

Hereinafter, the present invention is described in detail.
1. T-Cell Receptor Chimeric Protein
(1) Structure of T-Cell Receptor Chimeric Protein A method of the present invention uses a T-cell receptor chimeric protein prepared by fusing a variable region of a T-cell receptor (TCR: T-cell receptor) with an Fc region of an immunoglobulin. The T-cell receptor chimeric protein is also called as a T-cell receptor-immunoglobulin chimeric protein or a TCR-IgFc fusion protein.

The T-cell receptor chimeric protein of the present invention is a chimeric protein wherein all of a T-cell receptor variable region (TCR V region) and CDR3, and a J region are fused with an IgFc portion. In addition, it may be a chimeric protein wherein all of a T-cell receptor variable region (TCR V region) and CDR3, J region, and a part of C region are fused with an IgFc portion. The T-cell receptor chimeric protein of the present invention may be expressed as mTRAV8-CDR3-IgFc.

As the variable region of the T-cell receptor, used is a variable region of a T-cell receptor that recognizes an antigen specific to a cancer cell or infected cell. A T-cell receptor chimeric protein enables an NK cell to recognize a MHC positive ($MHC^+$) cancer cell or an MHC positive (MHC+) infected cell having an MHC class I molecule expressed therein, thereby allowing the NK cell to function like a killer T-cell.

A T-cell receptor is a dimer of an α chain and a β chain, or a γ chain and a δ chain, and each chain is formed of a variable region and a constant region. A variable region is coded by a plurality of gene fragments: V (variable) regions (V gene fragment), a D (diversity) region and a J (joining) region (β chain, δ chain); or a V region and a J region (α chain, γ chain), and it has many repertoires through gene rearrangement. Further, three hypervariable regions called CDR (complementarity determining region) are present in a variable region and somatic mutations thereof allow the variable region to have even more repertoires. In particular, a CDR3 region is involved in antigen specificity and sequence variations are likely to occur therein, so that it has a large sequence diversity.

The T-cell receptor variable region possessed by the T-cell receptor chimeric protein of the present invention is an α chain and β chain, and may be a single strand wherein both α chain and β chain are fused. Further, in a T-cell receptor chimeric protein forming a dimer, one strand may be a fusion protein of an immunoglobulin Fc region and a T-cell receptor α chain and the other strand may be a fusion protein of an immunoglobulin Fc region and a T-cell receptor β chain. Alternatively, a T-cell receptor variable region possessed by the T-cell receptor chimeric protein is a γ chain and a δ chain and may be a single strand wherein both of the γ chain and δ chain are fused. Further, in the T-cell receptor chimeric protein forming a dimer, one strand may be a fusion protein of an immunoglobulin Fc region and a T-cell receptor γ chain and the other strand may be a fusion protein of an immunoglobulin Fc region and a T-cell receptor δ chain. In a T-cell receptor variable region, an α chain, a β chain, a γ chain or a δ chain is composed of about 200 to 400 amino acids. α chain, β chain, γ chain and δ chain of the T-cell receptor variable region used in the present invention include those of naturally occurring T-cell receptor variable regions, and T-cell receptor variable regions having amino acid sequences having 90% or more, 95% or more 97% or more or 99% or more identity when calculated by use of BLAST (Basic Local Alignment Search Tool at the National Center for Biological Information), etc. (for example, a default or a parameter for initial setting is used).

It is essential that the T-cell receptor chimeric protein of the present invention should include a CDR3 region and preferably should be a multimer, such as a dimer or a tetramer. Examples of a dimer variable region include a combination of α chain-α chain, a combination of α chain-β chain, and a combination of β chain-β chain. Examples of a tetramer variable region include a combination of α chain-α chain and β chain-β chain.

Since a CDR3 region is antigen specific, the T-cell chimeric protein of the present invention can selectively bind to a complex of a specific antigen and an MHC and reduce the expression thereof.

The T-cell receptor variable region may be derived from any T-cell as long as it binds to MHC class I; it may be derived from helper T-cells (CD4 positive T-cells) or killer T-cells (CD8 positive T-cells), may be derived from regulatory T-cells (T reg), and may be derived from effector T-cells. Since a T-cell receptor derived from any of these T-cells can recognize and bind to a MHC class I molecule, it can be used as a constituent molecule of the T-cell receptor chimeric protein of the present invention.

"Immunoglobulin Fc region" mentioned in the present invention refers to an immunoglobulin Fc fragment, that is CH2 and CH3 constant domains of a natural immunoglobulin. As the immunoglobulin Fc region, human-derived ones are preferably used, but immunoglobulin of non-human animals such as mouse immunoglobulin may be used therefor. The immunoglobulin is preferably IgG. Subclasses of human IgG include IgG1, IgG2, IgG3 and IgG4, and mouse immunoglobulin includes IgG1, IgG2a, IgG2b and IgG3. Regarding human IgG, Fc regions of IgG1 and IgG3 strongly bind to an Fc receptor, so IgG1 and IgG3 are preferred; among them, IgG1 is preferred. Regarding mouse IgG, an Fc region of IgG2a is likely to bind to an Fc receptor (FcR) of an NK cell, and thus, IgG2a is preferred. The immunoglobulin Fc region includes all of natural mutants, artificial mutants and truncated forms. Examples thereof include Fc regions having amino acid sequences having 90% or more, 95% or more, 97% or more or 99% or more of naturally-occurring immunoglobulin Fc regions when calculated by use of BLAST (Basic Local Alignment Search Tool at the National Center for Biological Information), etc. (for example, a default or a parameter for initial setting is used).

In the T-cell receptor chimeric protein, a linker may be incorporated between T-cell receptor variable regions, between Fc regions of immunoglobulin, or between α chain and β chain when α chain and β chain are present in the T-cell receptor variable region, and two proteins may be tandemly bound to each other through a linker. The linker is a peptide linker composed of an amino acid sequence having a specific length; and the number of amino acids is not limited, but it is 1 to 30, preferably 3 to 25, and further preferably 5 to 20. The kind of amino acid is not limited, and it is preferably an amino acid having a small side chain and being less reactive, or an amino acid having an α helix structure when being bound. Examples of these amino acids include glycine (G), serine (S), alanine (A), threonine (T), aspartic acid (D), lysine (K), glutamic acid (E), leucine (L) and methionine (M).

(2) Method for Specifying T-Cell Receptor (TCR)

In targeting a cancer cell specifying a TCR in the cancer cell, a T-cell receptor variable region capable of recognizing a cancer-specific antigen expressed in a specific cancer cell may be used as a T-cell receptor variable region. As such a T-cell receptor variable region, usable is, for example, a T-cell receptor variable region derived from a particular cancer patient. The type of cancer is not limited, and examples of cancer to be treated in the present invention include, by occurrence site, squamous cancer such as lung squamous cancer and cervical squamous cell, adenocarcinoma such as lung adenocarcinoma and cervical adenocarcinoma, and undifferentiated carcinoma; and they include, by tissue or organ, stomach cancer, lung cancer, liver cancer, colon cancer, pancreatic cancer, bladder cancer, prostate cancer, anal-rectal cancer, esophageal cancer, cervical cancer, endometrial cancer, breast cancer, skin cancer, kidney cancer, adrenal cancer, urethral cancer, penile cancer, testicular cancer, ureteropelvic cancer, brain and nerve tumors, lymphoma and leukemia, bone and bone sarcoma, leiomyoma, rhabdomyoma, and mesothelioma. For the above, use of a T-cell receptor variable region capable of recognizing a cancer-specific antigen such as: carcinoembryonic antigens (CEA) specific to large bowel cancer or gastrointestinal cancer; MAGE (melanoma antigen) specific to malignant melanoma; HER2/neu specific to breast cancer; human prostate cancer-specific antigen (PSA) specific to prostate cancer, and human prostatic acid phosphatase (PAP) and PSMA (prostate specific membrane antigen); WT1 peptide specific to leukemia or various cancers; and glypican 3 (GPC3) specific to hepatocellular cancer, can provide a T-cell receptor chimeric protein that can be widely used to treat many cancer patients. However, an appropriate cancer treatment for each cancer patient may be conducted by collecting lymphocytes from a cancer patient, identifying a repertoire of T-cell receptors of the lymphocytes, and using T-cell receptor variable regions found in the cancer patient at a high frequency. In this case, the T-cell receptors recognize a particular epitope of a cancer-specific antigen of the cancer patient. DNA encoding such a specific T-cell receptor specific to a particular epitope of a cancer cell can be obtained by comprehensively analyzing the T-cell receptor of the cancer patient. Some T-cell receptors have $10^{18}$ repertoires, but comprehensive analysis is currently available. For example, T-cells are collected from a lymph node of a cancer patient, and total mRNA is extracted and purified. Next, cDNA is synthesized from the total mRNA by a reverse transcriptase, and a cDNA library is produced. Sequences of the produced cDNA library are determined by a next-generation sequencer, and repertoires of the T-cell receptors can be analyzed. T-cell receptors with a high frequency in a patient with cancer can be determined as a specific T-cell receptor with high specificity to the cancer.

Next, the full length sequence of the T-cell receptor is cloned. For cloning, the full length sequence of the T-cell receptor is amplified by using a primer capable of binding to a 5'-terminal part of DNA encoding a T-cell receptor variable region and a primer capable of binding to a 3'-terminal part of a T-cell receptor constant region, and incorporated into a cloning vector, so that a library of full length genes encoding the T-cell receptor is produced. Genes of this full length gene library are sequenced again. A T-cell receptor exhibiting a high frequency in the T-cell receptor repertoire analysis is taken as a T-cell receptor specific to cancer, and a clone having a sequence of gene of this T-cell receptor is selected as a clone for a cancer-specific T-cell receptor.

In targeting an infected cell infected with a pathogen such as bacteria or viruses causative of an infectious disease, a T-cell receptor variable region capable of recognizing a specific antigen to a pathogen such as bacteria or viruses, which express an infected cell infected with a pathogen such as a particular bacterium or virus, may be used as a T-cell receptor variable region. As such a T-cell receptor variable region, usable is, for example, a T-cell receptor variable region derived from a patient with a particular infectious disease. A T-cell receptor variable region capable of recognizing a specific antigen to a pathogen may be referred to as a T-cell receptor variable region specific to a particular infectious disease. The infectious disease is not limited, and examples thereof include bacteria, viruses, fungi, rickettsiae and parasitic insects. Examples of pathogens causative of an infectious disease include: viruses such as influenza virus, adenovirus, RS virus, HCV (hepatitis C virus), HIV (human immunodeficiency virus), EBV (hepatitis B virus), HAV (A hepatitis virus), HPV (human papilloma virus), rabies virus, dengue virus, Ebola virus, Lassa virus and Zika virus; bacterial antigens such as hemolytic streptococcus, pathogenic coli such as O157, *Chlamydia trachomatis*, *Bordetella pertussis*, *Helicobacter pylori*, *Leptospira*, *Treponema pallidum*, *Toxoplasma gondii*, *Borrelia*, *Legionella*, anthrax, tuberculosis, *Staphylococcus aureus* and MRSA (methicillin-resistant *Staphylococcus aureus*); and protozoans such as malaria. An appropriate infectious disease treatment for each patient may be conducted by collecting lymphocytes from a patient with an infectious disease, identifying a repertoire of T-cell receptors of the lymphocytes, and using T-cell receptor variable regions found in the patient with the infectious disease at a high frequency. In this case, the T-cell receptors recognize a particular epitope of a pathogen-specific antigen of the patient with the infectious disease. DNA encoding such a specific T-cell receptor to a particular pathogen can be obtained by comprehensively analyzing the T-cell receptor of the patient with the infectious disease. Some T-cell receptors have $10^{18}$ repertoires, but comprehensive analysis is currently available. For example, T-cells are collected from a lymph node of a patient with an infectious disease, and total mRNA is extracted and purified. Next, cDNA is synthesized from the total mRNA by a reverse transcriptase, and a cDNA library is produced. Sequences of the produced cDNA library are determined by a next-generation sequencer, and repertoires of the T-cell receptors can be analyzed. T-cell receptors with a high frequency in a patient with an infectious disease can be determined as a specific T-cell receptor with high specificity to the pathogen causative of the infectious disease.

Next, the full length sequence of the T-cell receptor is cloned. For cloning, the full length sequence of the T-cell receptor is amplified by using a primer capable of binding to a 5'-terminal part of DNA encoding a T-cell receptor variable region and a primer capable of binding to a 3'-terminal part of a T-cell receptor constant region, and incorporated into a cloning vector, so that a library of full length genes encoding the T-cell receptor is produced. Genes of this full length gene library are sequenced again. A T-cell receptor exhibiting a high frequency in the T-cell receptor repertoire analysis is taken as a T-cell receptor specific to the infectious disease, and a clone having a sequence of gene of this T-cell receptor is selected as a clone for a T-cell receptor specific to an antigen of the pathogen.

Repertoire analysis of T-cell receptors can be carried out by use of, for example, IMGT/V-Quest tool (http://www.imgt.org/).

In the above method, after a sequence of a cancer-specific T-cell receptor or a T-cell receptor specific to an antigen of a pathogen is determined by repertoire analysis of T-cell receptors, the full length gene of the T-cell receptor is cloned again, a library is produced, and a clone having a sequence of the T-cell receptor involved in recognition of a cancer-specific antigen or a T-cell receptor specific to an antigen of a pathogen is selected from the library.

Comprehensive analysis on T-cell receptors of a cancer patient or a patient with an infectious disease can be carried out for 1 to 2 weeks after blood collection. Thereafter, a cloning of T-cell receptors and production of a chimeric protein may be carried out. About 3 to 5 weeks in the shortest period after blood collection can provide a T-cell receptor chimeric protein that enables an individualized (custom-made) therapy suitable for a particular cancer patient or a patient with a particular infectious disease. At that time, a T-cell receptor and an immunoglobulin Fc region from a patient may be used, and a T-cell receptor chimeric protein derived from the patient for both of them would be used, thereby reducing side effects caused by immunoreaction.

Further, a T-cell receptor can be specified by the following concrete method.

As a first method, listed is a method for comparing TCR frequencies between a tissue around a disease, for example, a tissue around cancer, and peripheral blood. First, TCR frequencies in a disease tissue and peripheral blood are calculated for each specimen. A comparison is made between a TCR frequency of the disease tissue and a TCR frequency of the peripheral blood (TCR frequency of disease tissue/TCR frequency of peripheral blood), and those exhibiting two-fold or more difference in the ration are listed using TCR V regions (individual pair analysis). Those having a very small TCR frequency in the tissue around the disease, for example, less than 1%, are excluded. In the individual pair analysis, from TCRs exhibiting a large ratio, for example two-fold or more, preferably three-fold or more, about top 5 to 10 TCRs are picked up. This method is called Analysis 1.

That is, this method is a method for specifying a cancer-specific T-cell receptor α chain variable region, which includes: identifying a repertoire of a T-cell receptor α chain variable region of a lymphocyte in a cancer tissue of a cancer patient and a repertoire of a T-cell receptor α chain of a lymphocyte in peripheral blood of the cancer patient; and determining, as the cancer-specific T-cell receptor α chain variable region, a T-cell receptor α chain variable region that is present in the lymphocyte in the cancer tissue two-fold or more in abundance than in the lymphocyte in the peripheral blood. It is also a method for specifying a cancer-specific T-cell receptor α chain variable region, which includes: specifying a cancer-specific T-cell receptor α chain variable region in a plurality of cancer patients; and determining, as a cancer-specific human common T-cell receptor α chain variable region, a T-cell receptor α chain variable region that is present two-fold or more in abundance in the lymphocyte in the cancer tissue than in the lymphocyte in the peripheral blood. This method can be used to specify not only α chain variable region of a T-cell receptor but also a β chain variable region thereof.

A second method is to add up and average frequencies of each specimen on TCR frequencies in the disease tissues, and then place them in frequency order and pick up about top 10 (total single analysis). TCR frequencies in the peripheral blood of healthy subjects are placed in frequency order and about top 10 frequencies are picked up. While focus is being placed on V region, from TCRs picked up from the disease tissue, those overlapping those picked up from the peripheral blood of the healthy subjects are excluded, and the remainder is taken as a specified TCR. This method is called Analysis 2. This method can be used to specify not only α chain variable region of a T-cell receptor but also a β chain variable region thereof.

That is, this method is a method for specifying a cancer-specific T-cell receptor α chain variable region, which includes: a repertoire of a T-cell receptor α chain variable region of a lymphocyte in a cancer tissue of a cancer patient and a repertoire of a T-cell receptor α chain of a lymphocyte in peripheral blood of a healthy subject; and determining, as a cancer-specific T-cell receptor α chain variable region, a T-cell receptor α chain variable region that is present two-fold or more in abundance in the lymphocyte in the cancer tissue than in the lymphocyte in peripheral blood of the healthy subject. It is also a method, which uses a mixture of lymphocytes in cancer tissues of a plurality of cancer patients and a mixture of lymphocytes in peripheral blood of a plurality of healthy subjects to determine, as a cancer-specific human common T-cell receptor α chain variable region, a T-cell receptor α chain variable region that is present two-fold or more in abundance in the lymphocytes in the cancer tissues than in the lymphocytes in peripheral blood of the healthy subjects.

TCR V regions selected through Analysis 1 and Analysis 2 are added up and they are regarded as common TCRs. Among them, common and overlapping TCRs between Analysis 1 and Analysis 2 are taken as a particularly important TCR.

Examples of the common and overlapping TCR between Analysis 1 and Analysis 2 include the following TCRs having a T-cell receptor α chain variable region.

As TCRs specific to cervical cancer, provided are 12 TCRs having a T-cell receptor α chain variable region including TRAV (T-cell receptor Alpha Variable) 1-1-01, 1-1-02, 21-02, 22-01, 1-2-01, 12-2-03, 39-01, TRAV2-01, 21-01, 12-1-01, 1-2-01, and 38-2/DV8-01.

A cancer-specific human common T-cell receptor α chain variable region specific to cervical cancer has a CDR3 region having a consensus frame represented by AVR—(x=1 to 6)—G—(x=1 to 3)—KL(I)/(T).

Further, as TCRs specific to lung cancer, provided are 8 TCRs having a T-cell receptor α chain variable region including TRAV12-1-01, 16-01, 19-01, 22-01, 35-02, 17-01, 9-2-02 and 13-1-01.

(3) Production of T-Cell Receptor Chimeric Protein

If comprehensive analysis of T-cell receptors is conducted at a time on a plurality of patients, many repertoires of T-cell receptors can be acquired, enabling a library of many DNAs encoding a T-cell receptor variable region to be produced and maintained. Thereafter, in the case that: T-cell receptor analysis is conducted on a cancer patient or a patient with an infectious disease requiring treatment; and the T-cell receptor possessed by the patient or a T-cell receptor having an approximate sequence is present in the library, DNA thereof may be used to produce a T-cell receptor chimeric protein.

Figure 4:
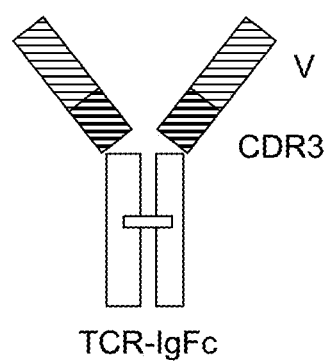
FIG. 4 shows a structure of a T-cell receptor chimeric protein.

The T-cell receptor chimeric protein of the present invention includes a monomer having one fusion protein wherein a T-cell receptor α chain variable region and/or β chain variable region and an immunoglobulin Fc region are fused and a linker peptide is contained, if necessary, or a dimer having two fusion proteins. Preferred is a dimer shown in FIG. 4. The T-cell receptor chimeric protein of the present invention can form a dimer by disulfide bond. One of two T-cell receptor variable regions of a dimer may be an β chain and the other may be a β chain.

Figure 5:
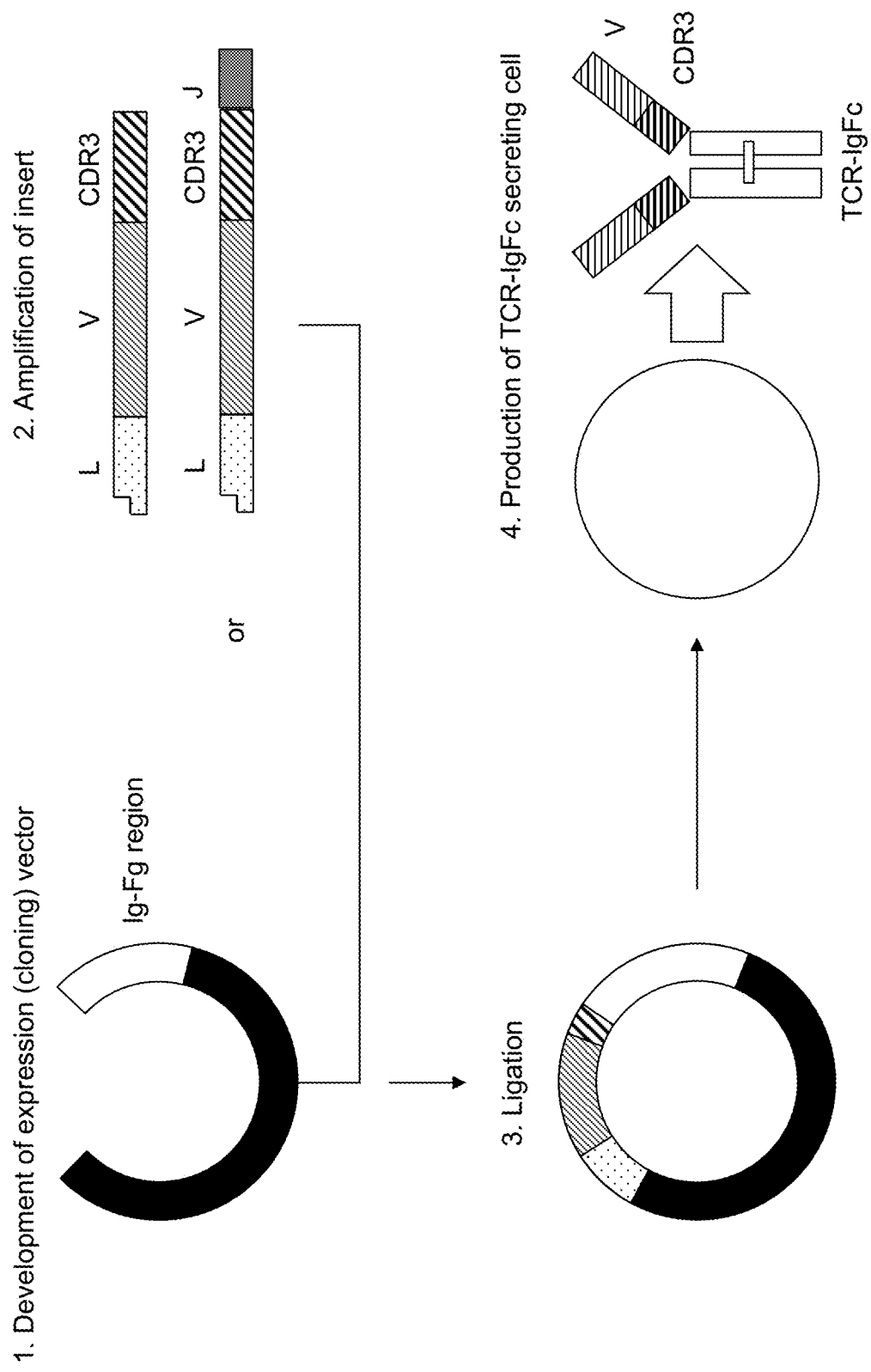
FIG. 5 shows an outline on a production method of a T-cell receptor chimeric protein by transgenic technology.

The T-cell receptor chimeric protein of the present invention can be produced by known fusion protein production methods, for example, a chemical synthesis method, a method utilizing a transgenic technology, and it is produced preferably by transgenic technology. An outline of a method utilizing a transgenic technology is shown in FIG. 5. When the T-cell receptor chimeric protein of the present invention is produced by a transgenic technology, DNA encoding a T-cell receptor α and/or β chain variable region and an immunoglobulin Fc region, and if necessary, a linker peptide is ligated in-frame, DNA encoding a fusion protein is introduced into an expression vector to produce a recombinant vector, and further, the recombinant vector is introduced and expressed into a host such as animal cells insect cells, plant cells, yeast and bacteria.

As the vector, any vector that is replicable in a host cell such as a plasmid, phage, and virus is usable. The vector includes a promotor, a replication origin, a selective marker; and if necessary, it may include an enhancer, a terminator sequence (terminator), a ribosome binding site, polyadenylation signal or the like.

A produced T-cell receptor chimeric protein can be, if necessary, isolated and purified by isolation and purification means well known to those skilled in the art. Examples of isolation and purification method include affinity chromatography, ion exchange chromatography, mixed-mode chromatography, dialysis, fractional precipitation, electrophoresis and others. An appropriate combination of these methods enables the T-cell receptor chimeric protein of the present invention to be isolated and purified.

Further, the T-cell receptor chimeric protein of the present invention can be expressed in a cell-free translation system (cell-free system).

The T-cell receptor chimeric protein of the present invention may have a chemical modification known to those skilled in the art. Examples of chemical modification include polyethylene glycosylation (PEG), glycosylation, acetylation, amidation, and others.

2. Use of T-Cell Receptor Chimeric Protein (1) Incorporation of T-Cell Receptor Chimeric Protein into Cell and Down-Modulation of MHC Complex on Cell Surface A T-cell receptor chimeric protein can down-modulate an MHC complex on the cell surface. In addition, a T-cell receptor chimeric protein bound to an MHC complex can be introduced into a cell.

The present invention includes a down-modulating agent of an MHC complex in a cell, which comprises a T-cell receptor chimeric protein as an active ingredient. The T-cell receptor chimeric protein used as an active ingredient of the MHC complex down-modulating agent is preferably a multimer such as a dimer or a tetramer. A multimer exhibits a better clustering efficiency and a higher MHC complex down-modulating effect.

A T-cell receptor exhibits its function by binding to an MHC complex and transmitting a signal to a T-cell. The T-cell receptor chimeric protein of the present invention binds to an MHC complex on the cell surface, and thereafter, incorporated into the cell, thereby down-modulating the MHC complex on the cell surface. The T-cell receptor chimeric protein bound to the MHC complex on the cell surface is incorporated into the cell 1 to 10 hours later, preferably 4 to 8 hours later and further preferably 6 hours later.

The MHC complex bound to the T-cell receptor chimeric protein of the present invention is not limited to a class I molecule, and it may be a class II molecule. There exist H-2K, D, L, I-A and I-E for a mouse, and HLA-A, B, C, DR, DQ, DM and E for human. Further, the target cell is not limited to cells with cancer or infectious disease, and it any cells including normal cells can be a subject.

Further, the phenomena wherein the T-cell receptor chimeric protein binds to an MHC complex and is incorporated into a cell several hours later can be used as follows. That is, a T-cell receptor chimeric protein capable of recognizing an MHC complex of a cell as a target is produced. Next, a magnetic substance or drug is imparted directly to the T-cell receptor chimeric protein; or a binding protein such as a secondary antibody having a magnetic substance or drug imparted thereto, which recognizes the T-cell receptor chimeric protein, is added thereto. As a result, use of the T-cell receptor chimeric protein enables the magnetic substance or drug to be introduced into the cytoplasm of a target cell. The magnetic substance used herein includes magnetic nanoparticles and the like. Examples of the magnetic nanoparticles include metal nanoparticles such as iron oxide nanoparticles and magnetite nanoparticles having a diameter of 1 to 100 nm. A magnetic nanoparticle may be enveloped for use. Magnetic nanoparticles incorporated into target cells such as cancer cells may be used as a heating element, in which an alternating magnetic field is applied extracorporeally to locally heat the cells to kill the target cells by thermotherapy using hyperthermia. In addition, the target cells can be killed by an anticancer drug or a drug for killing cells. The anticancer drug is not limited, and examples thereof include alkylating agents, antimetabolites, plant alkaloid, anticancer antibiotics, molecular target drugs, platinum-based drugs, hormone preparations, and the like. In this manner, a magnetic substance or drug incorporated into the cytoplasm by use of the T-cell receptor chimeric protein is utilized to selectively and efficiently destroy a target cell such as a cancer cell.

In this manner, a T-cell receptor chimeric protein can be used as a carrier of a magnetic substance or drug.

(2) Method for Enhancing Function of NK Cell by T-Cell Receptor Chimeric Protein Further, the present invention is a method for enhancing the function of an NK cell by use of a T-cell receptor chimeric protein. The present invention further includes a T-cell receptor chimeric protein used therefor.

The present invention provides the following two methods (a) and (b) for enhancing the function of an NK cell.

(a) An NK cell recognizes a cell expressing no MHC molecule as a target cell. The T-cell receptor chimeric protein binds to an MHC complex expressing a specific antigen, and is incorporated into a cell several hours later, e.g., 6 hours later, so an MHC complex molecule on the target cell is down-modulated. Thus, the NK cell can recognize the target cell thereby to attack it.

(b) An NK cell is allowed to recognize an MHC class I molecule, and thereby the NK cell can recognize a cancer cell or infected cell expressing an MHC class I molecule as a target cell. Thus, the cell can recognize the target cell thereby to attack it.

In the present invention, both of the methods (a) and (b) are referred to as a method for enhancing the function of an NK cell.

Figure 2:
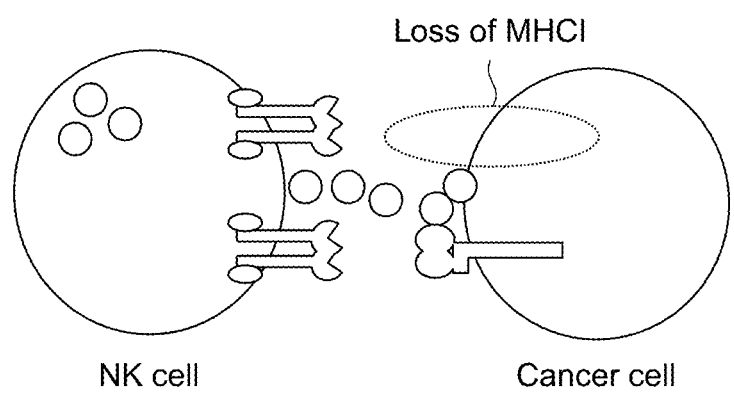
FIG. 2 shows a mechanism of NK cell for recognizing a cancer cell.
Figure 3:
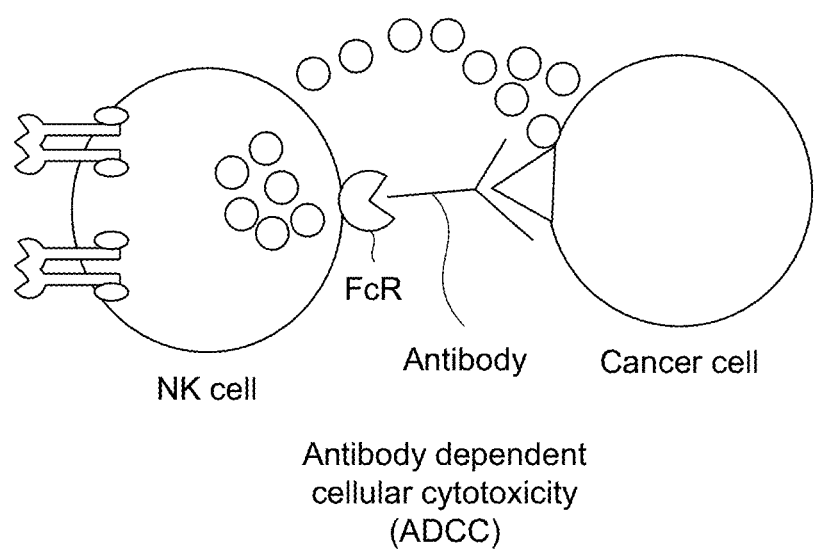
FIG. 3 shows a mechanism of antibody-dependent cell-mediated cytotoxicity (ADCC) by an NK cell.

A T-cell recognizes an MHC class I molecule and an antigen, thus recognizing a cell having an MHC class I molecule expressed thereon (FIG. 1). In practice, a T-cell recognizes a complex wherein a cancer-specific antigen or an antigen of a pathogen such as a bacterium or a virus causative of an infectious disease is bound to an MHC class I molecule, thereby recognizing the antigen bound to the MHC class I molecule. Meanwhile, an NK cell recognizes the non-existence of MHCs thereby to work, so the NK cell cannot recognize a target cell having an MHC class I molecule expressed thereon (FIG. 2). A normal cell usually has an MHC class I molecule expressed thereon, so it cannot be a target of an NK cell. Further, the expression of an MHC class I molecule often disappear in a malignantly progressed cancer cell, but many cancer cells or infected cells have an MHC class I molecule. The infected cells used herein refer to infected cells infected with a pathogen such as a bacterium or a virus causative of an infectious disease. A killer T-cell recognizes an MHC class I molecule of a cancer cell or infected cell thereby to attack them, so it is widely used for cancer immunotherapy or immunotherapy for infectious disease. Further, in certain types of cancer cells such as malignantly progressed cancer cells or intractable cancer cells, MHC class I molecules disappear. These cancer cells escape the attack of T-cells, so it has been necessary for NK cells to attack them. An NK cell has an immunoglobulin Fc region receptor (Fc receptor: FcR), thereby enabling antibody-dependent cellular cytotoxicity (ADCC) targeting a cell sensitized by humoral immunity (FIG. 3).

The above method (a) down-modulates MHC molecules on the surface of target cells. Thus, NK cells originally present in the body of a patient recognize target cells such as cancer cells or infected cells and attack them, resulting in the killing of these target cells.

In addition, the above method (b) enables NK cells to recognize MHC class I molecules, and thereby, the NK cells would attack, as target cells, cancer cells or infected cells having MHC class I molecules expressed thereon.

In the method (b), an NK cell in its natural condition does not recognize a cancer cell or an infected cell infected with a pathogen such as a bacterium or a virus causative of an infectious disease having an MHC class I molecule expressed thereon (FIG. 2). However, under the presence of the T-cell receptor chimeric protein of the present invention, the Fc portion of the T-cell receptor chimeric protein binds to the Fc receptor (FcR) of the NK cell, and the T-cell receptor variable region of the T-cell receptor chimeric protein binds to a cancer specific antigen or a pathogen-specific antigen bound to an MHC class I molecule of a cancer cell as a target. As a result, the NK cell recognizes, as a target cell, a cancer cell or infected cell having an MHC class I molecule expressed thereon through the T-cell receptor chimeric protein, and attacks the cancer cell or infected cell.

Figure 6:
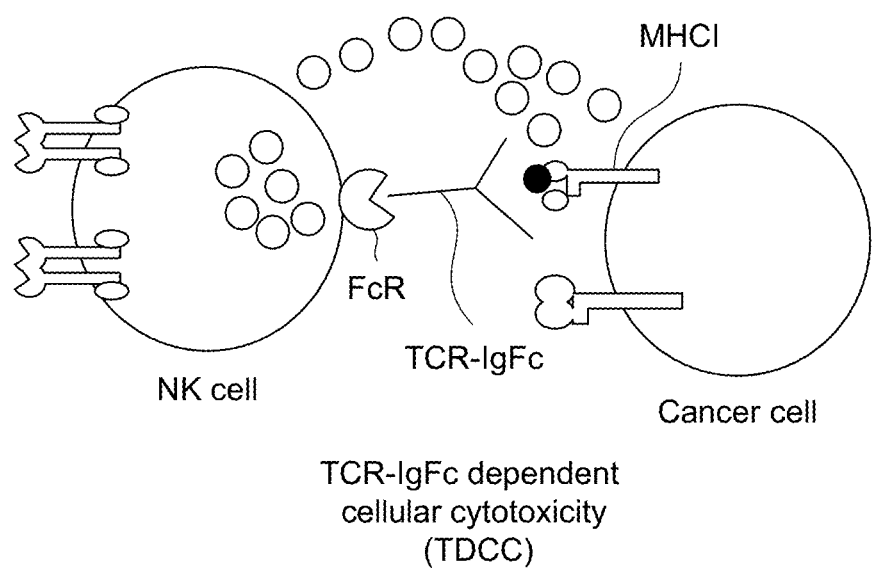
FIG. 6 shows a mechanism of an NK cell for T-cell receptor chimeric protein-dependent cellular cytotoxicity (TDCC: TCR-IgFc dependent cellular cytotoxicity).

Accordingly, the T-cell receptor chimeric protein of the present invention imparts the function of recognizing an MHC class I molecule to an NK cell originally possessed by a living body, thereby enabling the NK cell to exhibit damaging activity on an MHC class I molecule positive cancer cell or MHC class I molecule positive infected cell having an MHC class I molecule expressed thereon. That is, the T-cell receptor chimeric protein of the present invention has an effect of enhancing the function of NK cells, that is imparting to the NK cells the damaging activity on MHC class I molecule positive cancer cells or MHC class I molecule positive infected cells. In this regard, the T-cell receptor chimeric protein of the present invention can be used as an NK cell function enhancer. In the present invention, the damage and cytotoxicity of NK cells capable of recognizing an MHC class I molecule is called as TDCC (TCR-IgFc dependent cellular cytotoxicity) (FIG. 6).

Figure 7:
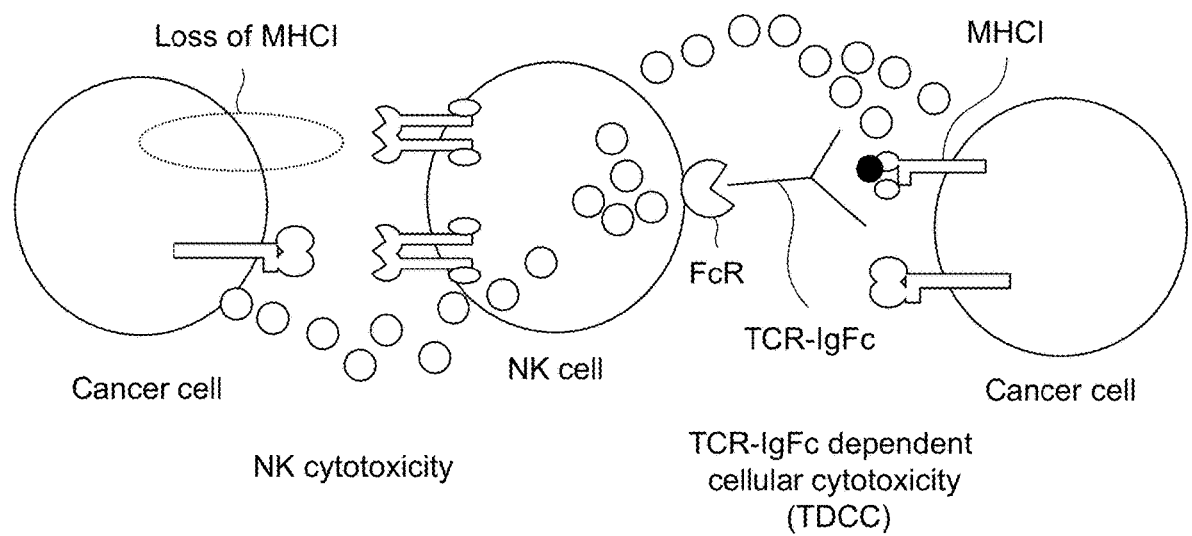
FIG. 7 shows that the ability of NK cell cytotoxicity is enhanced due to the occurrence of T-cell receptor chimeric protein-dependent cellular cytotoxicity and ordinary NK cell cytotoxicity.

Note that NK cells originally present in the body of a patient recognize cancer cells such as intractable cancer or end-stage cancer, which do not express an MHC class I molecule. Thus, NK cells kill or damage cancer cells expressing an MHC class I protein by TDCC (TCR-IgFc dependent cellular cytotoxicity) activity through the T-cell receptor chimeric protein, and also they can independently kill and damage cancer cells not expressing an MHC class I protein (FIG. 7).

The present invention is a method for enhancing cancer cell damaging activity function or infected cell damaging activity function of NK cells by use of a T-cell receptor chimeric protein; and a pharmaceutical composition, which comprises, as an active ingredient, a T-cell receptor chimeric protein, which is usable as an enhancer of cancer cell damaging activity function or infected cell damaging activity function of NK cells. The pharmaceutical composition can be used for cancer treatment or infectious disease treatment.

Further, the T-cell receptor chimeric protein also suppresses cancer metastases and it can therefore be used as a cancer metastasis inhibitor.

A dosage form of pharmaceutical composition of the present invention is not limited, and various dosage forms may be used depending on the usage. Examples of oral preparations include tablets, powder, granules, fine granules, capsules and the like. In addition, examples of parenteral preparations include injections, inhalation powder, inhalation liquids, eye drops, solutions, lotions, sprays, nasal drops, infusions, suppositories, plasters and the like. The pharmaceutical composition of the present invention may be prepared by pharmaceutically and publicly-known methods in accordance with the dosage form. Examples of a pharmaceutical additive include excipients, disintegrants, binders, lubricants, diluents, buffers, tonicity agents, preservatives, stabilizers, solubilizing agents and the like. The pharmaceutical additive also includes physiological saline, injection solvents and the like.

For the pharmaceutical composition of the present invention, various administration methods are used depending on the usage. Examples thereof include oral administration, intravenous administration, subcutaneous administration, intramuscular administration, intraperitoneal administration, topical administration and the like.

When the pharmaceutical composition of the present invention is used for cancer treatment or infectious disease treatment, the dose of protein of the present invention as an active ingredient thereof is appropriately determined in accordance with the age, sex and weight of a patient, the severity of a disease, the dosage form and administration route, and the like. For example, when the pharmaceutical composition is orally administered to an adult, the dose may be determined within the range of 0.1 µg/kg to 1000 mg/kg/day. Daily dose may be administered at one time or divided into two or three fractions for administration. Further, when it is administered parenterally to an adult, the dose may be determined within the range of 0.01 µg/kg to 1000 mg/kg/day. Daily dose for parenteral administration may be determined, depending on the dosage form, in the range of preferably 0.1 µg/kg to 10 µg/kg/day, 1 µg/kg to 100 µg/kg/day, or 10 µg/kg to 1000 µg/kg/day.

In the above method (a), the T-cell receptor chimeric protein of the present invention is administered to a living body thereby to down-modulate an MHC class I protein on the surface of a particular target cell, and thus, an NK cell originally present in the body of a patient can attack and kill a target cell.

In the above method (b), the T-cell receptor chimeric protein of the present invention is administered to a living body to enhance the function of NK cells originally possessed by the living body. However, it is possible: to collect NK cells from a cancer patient or a patient with an infectious disease; to culture and grow NK cells for several weeks, and if necessary, to freeze them; and thereafter, to administer to the cancer patient or the patient with the infectious disease together with the T-cell receptor chimeric protein of the present invention. The administration may be simultaneously; the NK cells may be administered first, and then, the T-cell receptor chimeric protein may be administered; and the T-cell receptor chimeric protein may be administered first, and then, the NK cells may be administered. In this case of the present invention, an NK cell and a T-cell receptor chimeric protein are administered in combination, and therefore, the present invention includes a pharmaceutical composition or a kit of a combination of an NK cell and a T-cell receptor chimeric protein.

Further, it is possible to bring NK cells collected and grown from a cancer patient or a patient with an infectious disease into in vivo contact with a T-cell receptor protein, to produce in vivo a complex of the NK cell and the T-cell receptor chimeric protein, and to use the complex for cancer treatment or infectious disease treatment. The present invention includes a complex of a T-cell receptor chimeric protein and an NK cell receptor, and further includes a method for producing a complex of a T-cell receptor chimeric protein and an NK cell by bringing the T-cell receptor chimeric protein and the NK cell with in vivo contact with each other. The complex may be administered as a cell reagent. Further, it is possible to collect NK cells from a cancer cell or a patient with an infectious disease; and to introduce and express DNA encoding a T-cell receptor chimeric protein into the NK cell. Thereafter, the NK cell may be cultured and grown for several weeks, and if necessary, frozen; and administered to the cancer patient or the patient with the infectious disease. Administration of the NK cell having TDCC (TCR-IgFc dependent cellular cytotoxicity) to the cancer patient or the patient with the infectious disease may be conducted by, for example, intravenous infusion. The administered NK cell expresses a T-cell receptor chimeric protein, and kills or damages a cancer cell or an infected cell having an MHC class I protein expressed thereon by TDCC through the T-cell receptor chimeric protein.

(3) Detection of Cancer Cell or Infected Cell

Further, the T-cell receptor chimeric protein of the present invention binds to a complex of an MHC class I molecule of a cancer cell and a cancer-specific antigen, or an MHC class I molecule of an infected cell and a pathogen-specific antigen, and thus, it can be used for detection of the cancer cell or the infected cell; and therefore, the detection of a cancer cell enables detection of cancer. In addition, the detection of an infected cell infected with a pathogen such as a bacterium or a virus causative of an infectious disease enables detection of the infectious disease.

In the case that the T-cell receptor chimeric protein is used to detect a cancer cell or infected cell, the T-cell receptor chimeric protein may be used by labeling it with an enzyme such as a fluorescent dye, quenching dye, a fluorescent protein, alkaline phosphatase (ALP), and horseradish peroxidase (HRP). Labeling with a labeling substance can be carried out by a publicly-known protein labeling method, and the labeling may be carried out by use of biotin-avidin (streptavidin) system.

Detection may be conducted by use of FACS or a flow cytometer, and also may be conducted by an immunocytochemical method. As the flow cytometer, FACSCant II (manufacture by Becton, Dickinson and Company), for example, may be used. Measurement by an immunocytochemical method may be conducted by fixing a collected cancer cell or infected cell on a glass slide. In the immunocytochemistry, staining may be determined by a microscope or the naked eyes, or by use of an appropriate optical measurement device.

If cells are collected from a biological sample such as blood or a tissue of a subject and brought into contact with a T-cell receptor chimeric protein and it is found that cells binding to the T-cell receptor chimeric protein are present, the cells are determined as cancer cells or infected cells and it is determined that cancer cells or infected cells are present in the subject. When cancer cells are detected from the subject, it can be determined that the subject has come down with cancer. Further, when an infected cell is detected from the subject, it is determined that the subject has come down with an infectious disease. Detection by use of the T-cell receptor chimeric protein can provide auxiliary data for cancer diagnosis or infectious disease diagnosis.

The present invention includes a reagent for cancer detection or a reagent for infectious disease detection, which includes a T-cell receptor chimeric protein, wherein the T-cell receptor chimeric protein is preferably labeled.

The patient determined as coming down with cancer can be treated by immunotherapy using the NK cell function enhancer of the present invention. In addition, the patient may be treated by surgical treatment, radiation treatment or chemotherapy. The patient determined as coming down with an infectious disease may be treated by immunotherapy using the NK cell function enhancer of the present invention.

In addition, the patent may be treated by administration of an antibacterial agent or an antiviral agent.

EXAMPLES

Although the present invention will be specifically described by the following examples, the present invention is not limited by these examples.

To identify a T-cell receptor that recognized a cancer cell, the tumor cell E.G7 that expressed MHC class I and into which an OVA (ovalbumin) gene was introduced was used as a mouse tumor cell. E.G7-OVA is derived from EL4 (ATCC TIB-39), which is a C57BL/6 (H-$2^b$) mouse lymphoma cell strain. The EL4 cell was transfected with the plasmid pAc-neo-OVA carrying a complete copy of chicken ovalbumin mRNA and a neomycin (G418) resistant gene by electroporation (Moore MW. et al., Cell 54: 777-785, 1988).

1. Expression Analysis of PD-1 on $CD8^+$ T-Cell by Flow Cytometry

1) Expression Analysis of PD-L1 on E.G7 Cell

Figure 8:
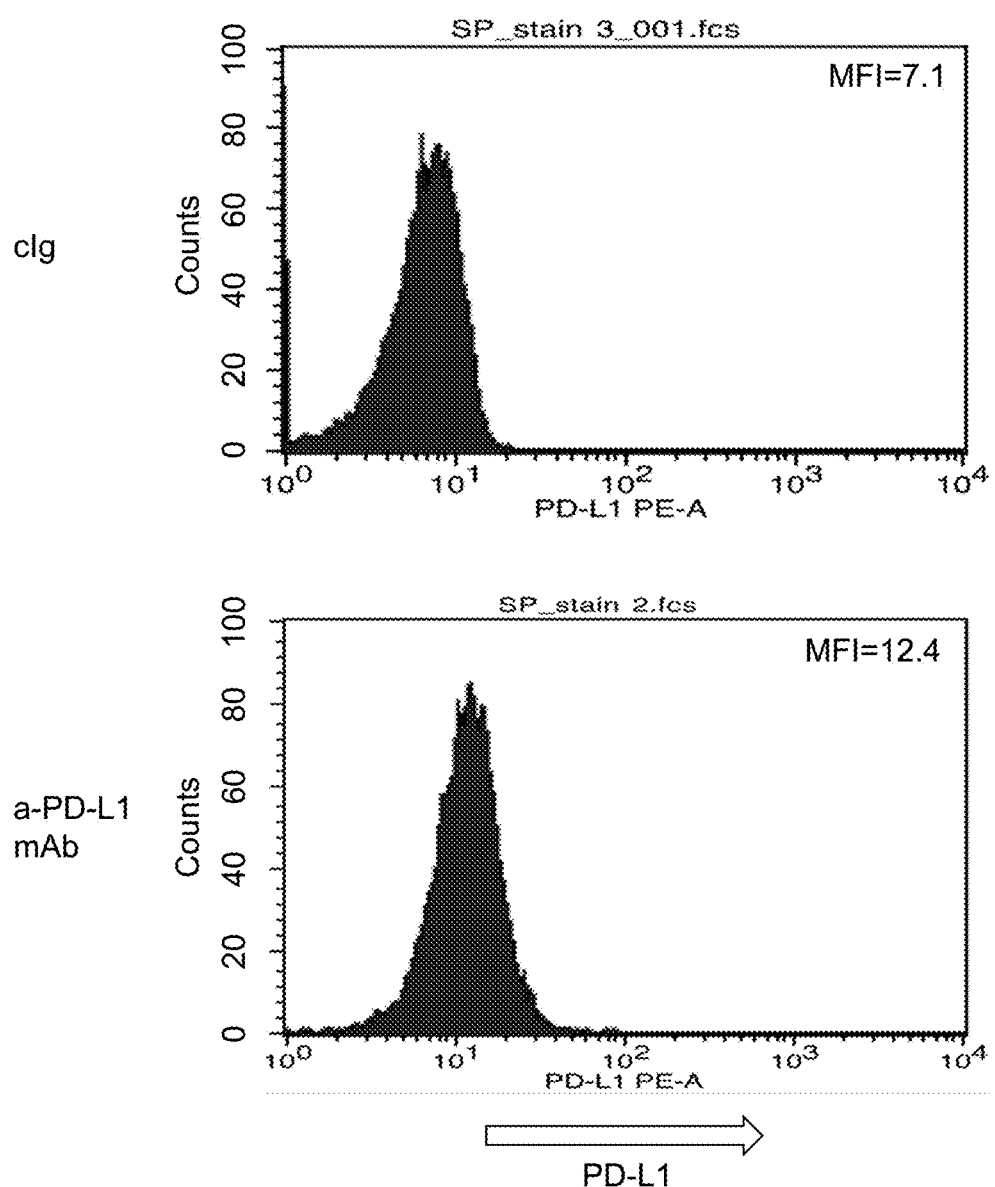
FIG. 8 shows results of expression analysis of PD-L1 on E.G7 cells.

The expression of PD-L1 on the E.G7 cell, which is a mouse lymphoma cell, was confirmed. First, 0.25 µg of an anti-PD-L1 fluorescent-labelled antibody (clone name 10F.9G2) was added to E.G7 cells, the cells were dyed at 4° C. for 30 minutes and then washed with PBS twice. This sample was analyzed by flow cytometry. The flow cytometry analysis was performed with an FACSCanto II (manufactured by Becton, Dickinson and Company). The result is shown in FIG. 8. The numerical value of the figure shows the Mean Fluorescence Intensity value (MFI). It was confirmed that PD-L1 was expressed on the E.G7 cell.

2) Expression Analysis of PD-1 on $CD8^+$ T-Cell

First, $5\times10^6$ E.G7 cells were transplanted to the planta of a C57BL/6 mouse. Lymphocytes in the spleen after 0, 10 and 15 days were collected (p18). The expression of PD-1 was examined using a fluorescence-labelled antibody. Then, 0.25 µg of a commercial fluorescence-labelled antibody was added to $1\times10^6$ lymphocytes, the lymphocytes were dyed at 4° C. for 30 minutes and then washed with PBS twice. To label dead cells, the lymphocytes were dyed using PI (Propidium Iodide) and prepared as an analysis sample. This sample was analyzed by flow cytometry. The flow cytometry analysis was performed with an FACSCanto II (manufactured by Becton, Dickinson and Company).

The used fluorescence-labelled antibodies are the following.
Anti-PD-1 antibody (clone name RMP1-14)
Anti-CD8 antibody (clone name 53-6.7)

Figure 9:
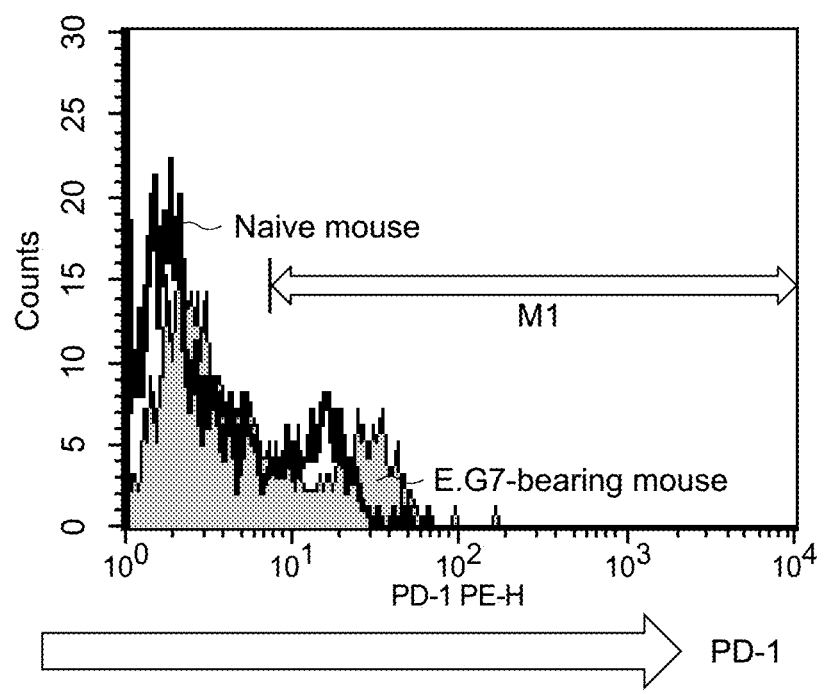
FIG. 9 shows results of expression analysis of PD-1 on $CD8^+$ T-cells.
Figure 10:
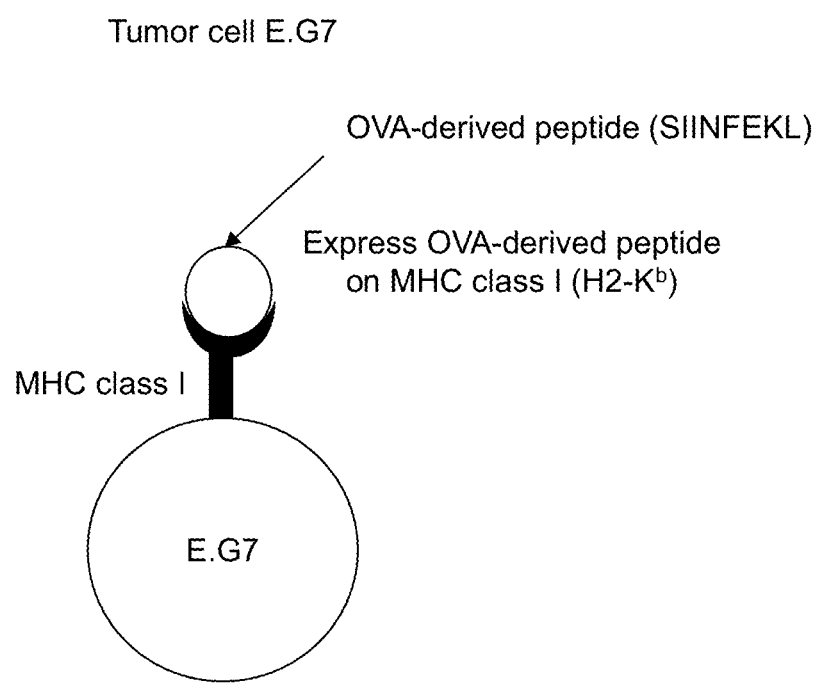
FIG. 10 shows an E.G7 cell that has expressed an MHC class I molecule and an OVA-derived peptide.

The result is shown in FIG. 9. The results of a naive mouse and the E.G7-bearing mouse are shown in FIG. 9. The expression of PD-1 increased in the $CD8^+$ T-cells. The schematic diagram of an E.G7 cell expressing a molecule of MHC class 1 and an OVA-derived peptide is shown in FIG. 10.

2. TCR Repertoire Analysis

Lymphocytes in the spleen were collected from a C57BL/6 mouse. This was used as a naive mouse sample. Then, $5\times10^6$ E.G7 cells were transplanted to the planta of a C57BL/6 mouse. Lymphocytes in the spleen after 10 days and 15 days were collected. Two mice were used for each case.

Total RNA was extracted, and a cDNA library was produced from the above-mentioned sample in a general method. An adapter was imparted, followed by PCR using "gene specific unbiased amplification" to amplify the gene of a TCR chain. This was used as an analysis sample.

Gene specific unbiased amplification is a method in which an adapter is imparted to the cDNA library, and the antisense strand (or sense strand) of the double-stranded adapter is then digested with an enzyme. The adapter ligation PCR method is performed using a primer based on the nucleotide sequence of the remaining adapter moiety and a TCR specific primer. This enables the suppression of nonspecific primer bonds and gene-specific amplification.

Specifically, gene specific unbiased amplification is performed by the following method:
(i) a step of ligating any double-stranded adapter DNA of the following [1] to [3] to the both ends of a double-stranded cDNA;
(ii) a step of treating the gene to which the double-stranded adapter DNA is ligated with a uracil DNA glycosylase (UNG) and further heat-treating the DNA to decompose the antisense strand of the adapter DNA; and
(iii) a step of performing PCR amplification using a forward primer comprising a part or all of the sequence of the antisense strand of the double-stranded adapter DNA and a reverse primer that anneals to the target gene specifically.

In this method, extension reaction by only the forward primer does not occur, but extension reaction by a reverse primer occurs to form the complementary strand of the sense strand of the adapter. The forward primer then anneals to the complementary strand, resulting in extension reaction, and extension by the reverse primer and extension by the forward primer occur in this order in one direction. The target gene can be amplified by the PCR method without being biased in one direction thereby.

[1] A double-stranded adapter DNA used for unbiased gene amplification, wherein
(a) a sense strand and an antisense strand anneal, and the base lengths of the sense strand and the antisense strand are the same, or the sense strand is longer;
(b) the base length of the sense strand is 15 to 40 bp;
(c) the antisense strand contains a plurality of uracil bases, the adapter is treated with a uracil DNA glycosylase (UNG), resulting in the removal of the uracil bases, and then heat-treated, resulting in the decomposition of the antisense strand;
(d) at least one end of the adapter DNA has the shape of a blunt end;
(e) the adapter DNA binds to a target gene to be amplified at one end; and
(f) a part or all of the sense strand is the sequence of the forward primer used for gene amplification.
[2] The double-stranded adapter DNA according to [1], wherein the number of uracil bases contained in the antisense strand is 10 to 25% out of the number of the bases of the antisense strand, a uracil base is present in every 5 to 10 bases.
[3] The double-stranded adapter DNA according to [1] or [2], wherein a phosphate group binds to the 5' end of the antisense strand, and an amino group binds to the 3' end.

Figure 11:
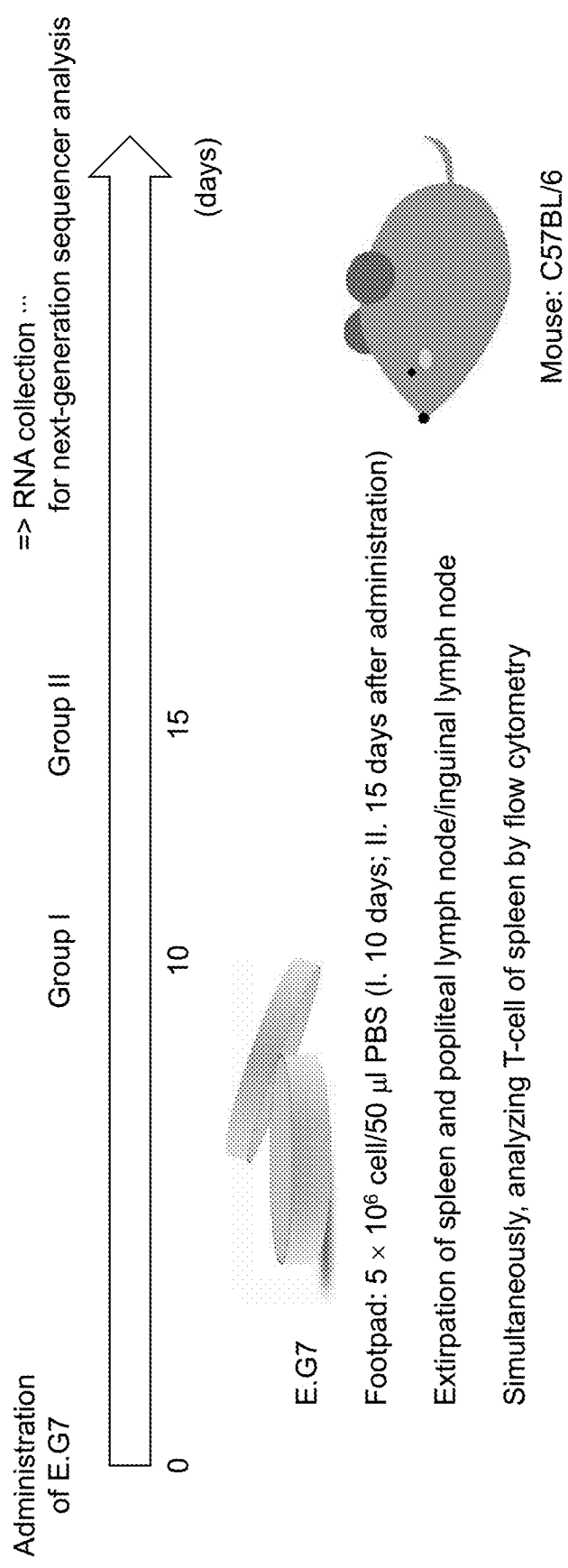
FIG. 11 shows an experimental method of TCR repertoire analysis.

The sample was analyzed using a Roche454GS Junior as a next generation sequencer according to the protocol of the maker. The experimental method is shown in FIG. 11.

Figure 12:
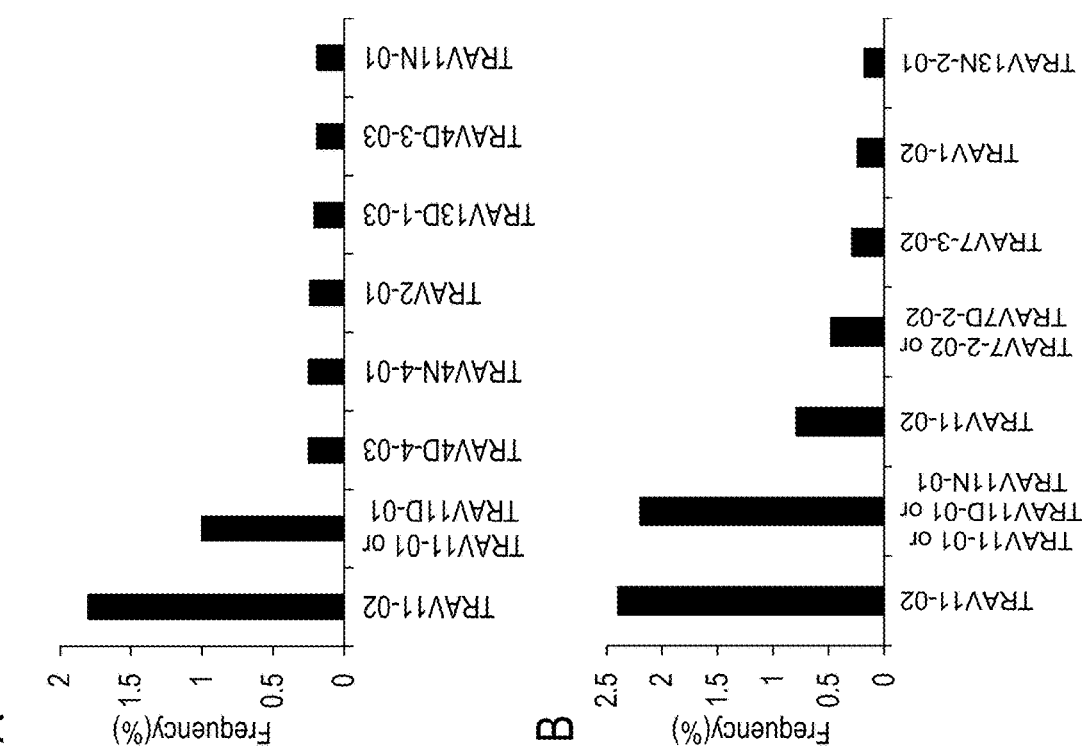
FIG. 12 shows analytical results of TCR α chain of lymphocytes collected from a naive mouse in TCR repertoire analysis.
Figure 17:
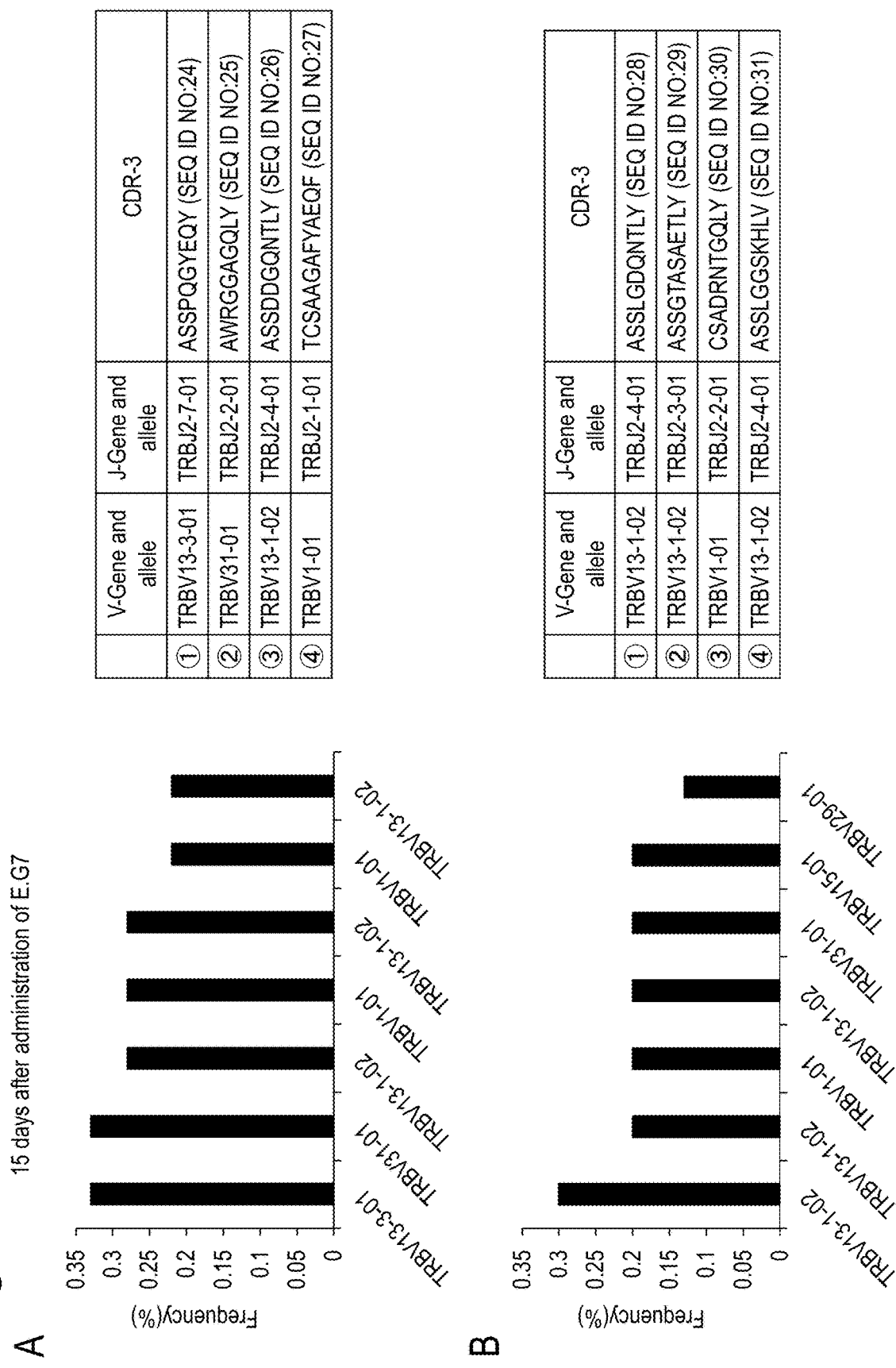
FIG. 17 shows analytical results of TCR β chain of lymphocytes collected from mice 15 days after inoculation with E.G7 in TCR repertoire analysis.

The results of α-chain naive mice, 10 days after E.G7 inoculation, and 15 days after E.G7 inoculation were obtained. The β-chain was also analyzed in the same way. The results of the analysis of the α-chain are shown in FIGS. 12 to 14. FIG. 12 shows the results of the α-chain naive mice, FIG. 13 shows the results 10 days after E.G7 inoculation, and FIG. 14 shows the results 15 days after E.G7 inoculation. In the Figures, A and B show the results of the two respective used mice. The results of the analysis of the β-chain are shown in FIGS. 15 to 17. FIG. 15 shows the results of β-chain naive mice, FIG. 16 shows the results 10 days after E.G7 inoculation, and FIG. 17 shows the results 15 days after E.G7 inoculation. In the Figures, A and B show the results of the two respective used mice. The amino acid sequences (SEQ ID NOS: 2 to 31) of the CDR3s of respective TCRs are shown in FIGS. 12 to 17.

Consequently, the α-chain of a TCR that reacts to E.G7 was identified as V region: TRAV8-1-01, J region: TRAJ42-01, CDR3 (amino acid sequence): ATLYSGGSNAKLT (SEQ ID NO: 1).

3. Preparation of T-Cell Receptor Chimeric Protein (mTRAV8-CDR3-IgFc)

1) Gene Cloning of T-Cell Receptor and Construction of Expression Plasmid

A region including the L region to a part of the C region of the TCR α-chain of the T-cell receptor having: V region: TRAV8-1-01, J region: TRAJ42-01, CDR3 (amino acid sequence): ATLYSGGSNAKLT (named del C) was cloned from the spleen sample cDNA library 15 days after E.G7 transplant using the following PCR primers.

Primer Sequence:
T01002 (V region sense strand, an EcoRI site is imparted): CGG AAT TCA TGC ACA GCC TCC TGG GGT TG (SEQ ID NO: 32)
T01005 (antisense strand including a part of the C region, Bgl II site is imparted): GAA GAT CTA GGT TCT GGG TTC TGG ATG TTT G (SEQ ID NO: 33)

The del C cDNA was inserted between the EcoRI and Bgl II sites of a commercial pFUSE-mIgG2A-Fc plasmid (InvivoGen Company) to construct a T-cell receptor chimeric protein plasmid (named TP58).

The summary of the method for prepare a T-cell receptor chimeric protein is shown in FIG. 5.

2) Production and Purification of T-cell Receptor Chimeric Protein (TCR-IgFc Fusion Protein)

The TP58 plasmid was introduced into a HEK293 cell, which was cultured in a culture medium in the presence of an ultralow IgG-FCS (for avoiding the contamination of bovine IgG in the subsequent purifying step) for 4 days. The culture supernatant was collected and purified using a Hi Trap protein G column (General Electric Company) according to a protocol of the maker.

This new T-cell receptor chimeric protein (mTRAV8-CDR3-IgFc) is a chimeric protein obtained by binding the TCR V region, CDR3, the J region, and a part of the C region to the IgFc moiety.

3) Preparation of Conventional T-Cell Receptor Chimeric Protein

Although a T-cell receptor chimeric protein has been prepared by prior research, the conventional T-cell receptor chimeric protein is a chimeric protein obtained by binding the TCR V region to the IgFc moiety. Accordingly, the above V region: TRAV8-1-01 was bound to the pFUSE-mIgG2A-Fc plasmid to construct a conventional T-cell receptor chimeric protein (mTRAV8-IgFc).

4. Bond of T-Cell Receptor Chimeric Protein to Cancer Cell

Since a new T-cell receptor chimeric protein (mTRAV8-CDR3-IgFc fusion protein) based on a T-cell receptor that reacted to E.G7 was prepared, the protein was biotinylated using a commercial biotinylation kit (Dojindo biotin labeling kit; Wako Pure Chemical Industries, Ltd.).

Figure 18:
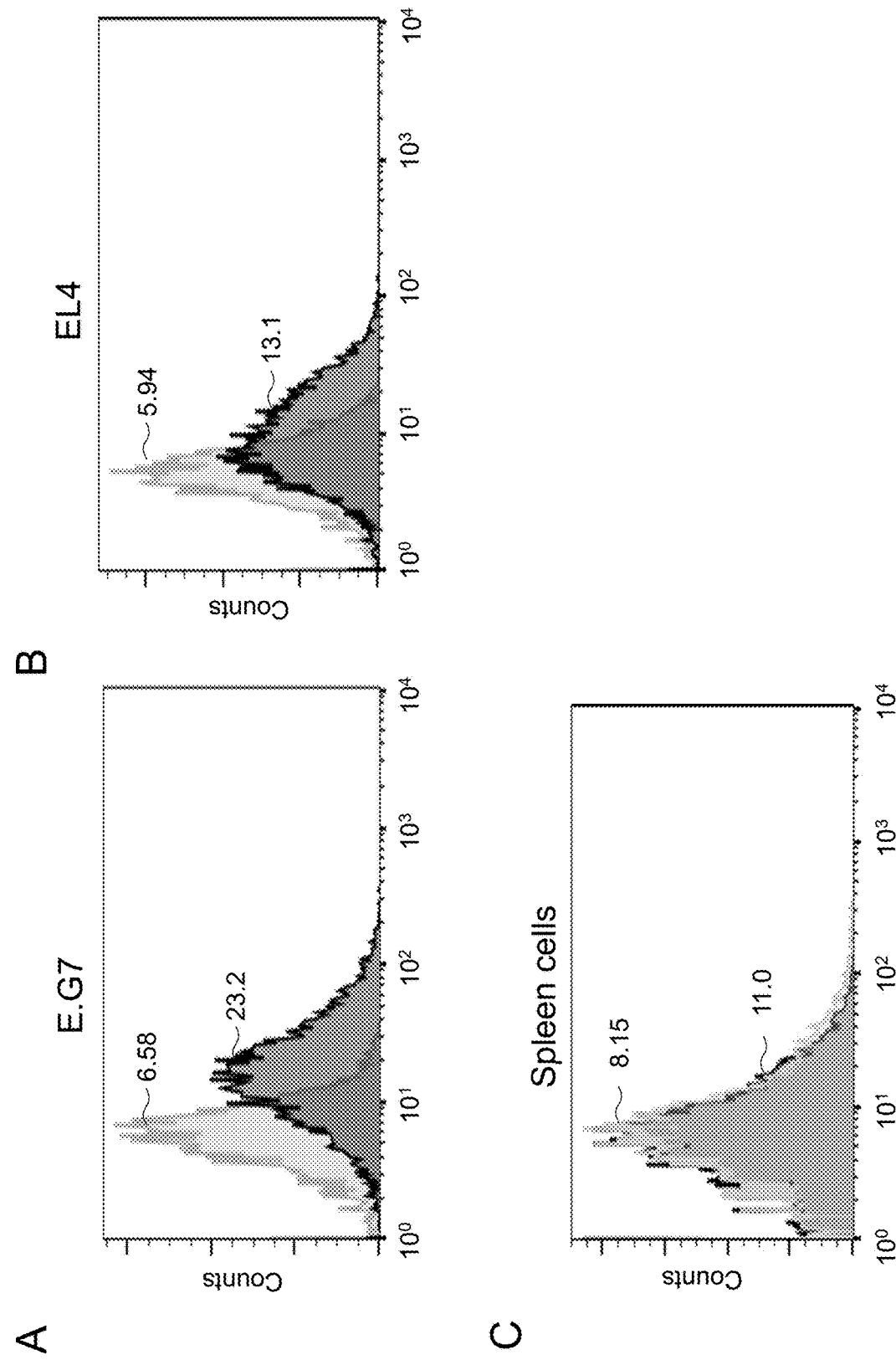
FIG. 18 shows that a T-cell receptor chimeric protein binds to cancer cells.
Figure 19:
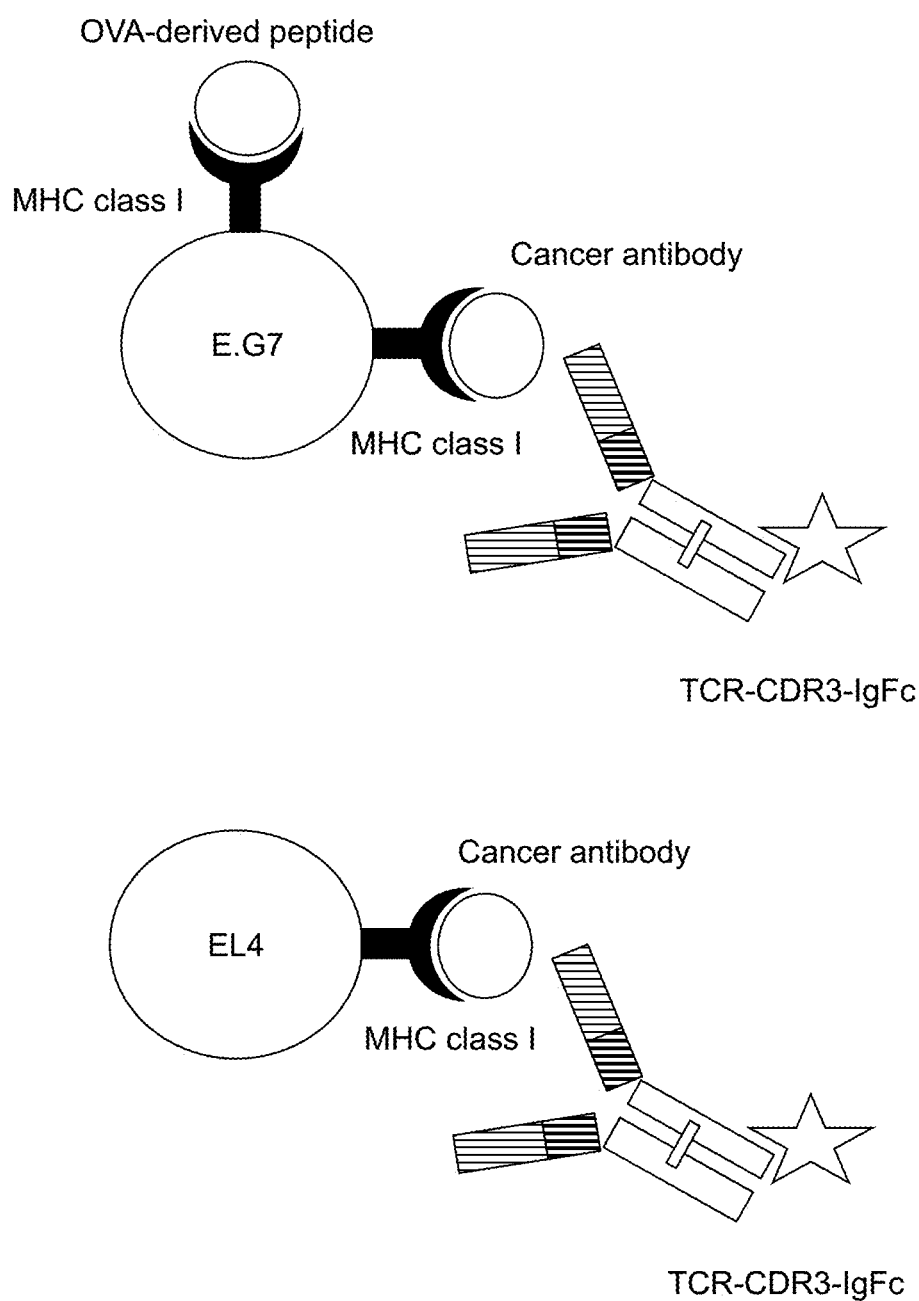
FIG. 19 shows a way wherein a T-cell receptor chimeric protein binds to a cancer cell.

Then, 0.5 µg of the biotinylated T-cell receptor chimeric protein was added to E.G7 cells, the biotinylated T-cell receptor chimeric protein and the E.G7 cells were bound at 4° C. for 60 minutes, and the cells were washed with PBS twice. Then, Streptavidin-PE (Thermo Fisher Scientific Inc.)

was added, and the cells were dyed at 4° C. for 30 minutes and washed with PBS twice. To label dead cells, the cells were dyed using PI (Propidium Iodide) and prepared as an analysis sample. This sample was analyzed by flow cytometry. The flow cytometry analysis was performed with an FACSCanto II (manufactured by Becton, Dickinson and Company). As a comparative control group, a sample obtained by adding Streptavidin-PE (Thermo Fisher Scientific Inc.) to E.G7 cells, dyeing the cells at 4° C. for 30 minutes and washing the cells with PBS twice was provided. Additionally, the bond of T-cell receptor chimeric protein was dyed in the same way using an EL4 cell, which is a parent strain of the E.G7 cell, and flow cytometry analysis was performed. The result is shown in FIG. 18. The numerical value of the figure indicates MFI. It was confirmed that the T-cell receptor chimeric protein bound to both E.G7 (FIG. 18A) and EL4 (FIG. 18B). Although C57BL/6 mouse spleen cells was dyed in the same way as a comparative control group, followed by flow cytometry analysis, the bond of the T-cell receptor chimeric protein to the spleen cells was not seen (FIG. 18C). Therefore, it turned out that the T-cell receptor chimeric protein specifically bound to cancer cells. The schematic diagram in which the T-cell receptor chimeric protein binds to cancer cells is shown in FIG. 19. This result shows that the new T-cell receptor chimeric protein (mTRAV8-CDR3-IgFc fusion protein) is specific to cancer, and recognizes a common MHC complex.

5. Comparison of Bondability of Conventional T-Cell Receptor Chimeric Protein (mTRAV8-IgFc) and New T-Cell Receptor Chimeric Protein (mTRAV8-CDR3-IgFc)

Figure 20:
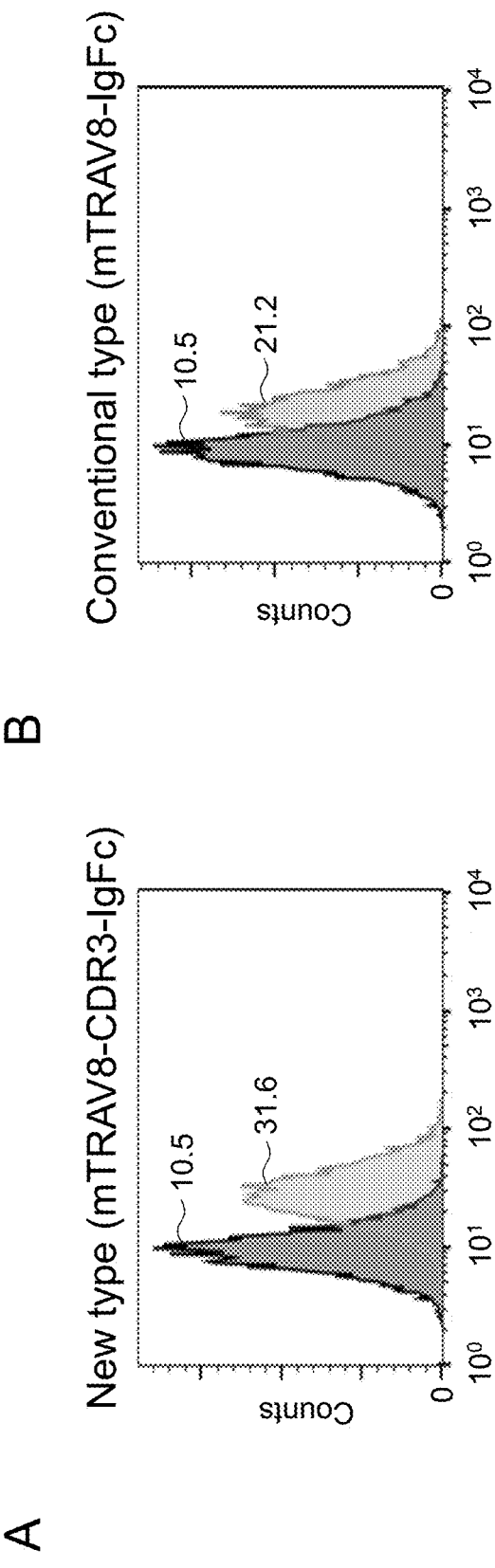
FIG. 20 shows a comparison on binding property between a conventional T-cell receptor chimeric protein (mTRAV8-IgFc) and new type T-cell receptor chimeric protein (mTRAV8-CDR3-IgFc).

First, 0.5 μg of a biotinylated T-cell receptor chimeric protein (conventional or new) was added to E.G7 cells, the protein and the cells were bound at 4° C. for 60 minutes, and the cell was washed with PBS twice. Then, Streptavidin-PE (Thermo Fisher Scientific Inc.) was added, and the cells were dyed at 4° C. for 30 minutes and washed with PBS twice. To label dead cells, the cells were dyed using PI (Propidium Iodide) and prepared as an analysis sample. This sample was analyzed by flow cytometry. The flow cytometry analysis was performed with an FACSCanto II (manufactured by Becton, Dickinson and Company). As a comparative control group, a sample obtained by adding Streptavidin-PE (Thermo Fisher Scientific Inc.) to E.G7 cells, dyeing the cells at 4° C. for 30 minutes and washing the cells with PBS twice was provided. The result is shown in FIG. 20. The numerical value of the figure indicates MFI. FIG. 20A shows the result of the new T-cell receptor chimeric protein (mTRAV8-CDR3-IgFc), and FIG. 20B shows the result of the conventional T-cell receptor chimeric protein (mTRAV8-IgFc). The new T-cell receptor chimeric protein recognized the antigen peptide specifically, and binds to cancer cells 1.5 times as efficiently as the conventional one by having the CDR3 region.

6. Detection of MHC Complex by T-Cell Receptor Chimeric Protein (mTRAV8-CDR3-IgFc)

A group in which 0.25 μg of an anti-MHC class 1 antibody (H-2$K^bD^b$; BioLegend, Inc.) was added to E.G7 cells and a group in which the anti-MHC class 1 antibody was not added to the E.G7 cells were provided. The antibody and the cells were bound at 4° C. for 30 minutes, and the cells were then washed with PBS twice. Then, 0.5 μg of the new biotinylated T-cell receptor chimeric protein was added to each sample, resulting in binding at 4° C. for 60 minutes, and the cells were washed with PBS twice. Then, Streptavidin-PE (Thermo Fisher Scientific Inc.) was added, and the cells were dyed at 4° C. for 30 minutes and washed with PBS twice. To label dead cells, the cells were dyed using PI (Propidium Iodide) and prepared as an analysis sample. This sample was analyzed by flow cytometry. The flow cytometry analysis was performed with an FACSCanto II (manufactured by Becton, Dickinson and Company). The result is shown in FIG. 21. The numerical value of the figure indicates MFI. FIG. 21A shows the result of the group to which the anti-MHC class 1 antibody was not added, and FIG. 21B shows the result of the group to which the anti-MHC class 1 antibody was added. The T-cell receptor chimeric protein was inhibited from binding by the anti-MHC class 1 antibody. This reveals that the T-cell receptor chimeric protein binds to the MHC complex. Bonding manners are shown above the graphs.

7. Cellular Internalization of T-Cell Receptor Chimeric Protein (mTRAV8-CDR3-IgFc)

Figure 22:
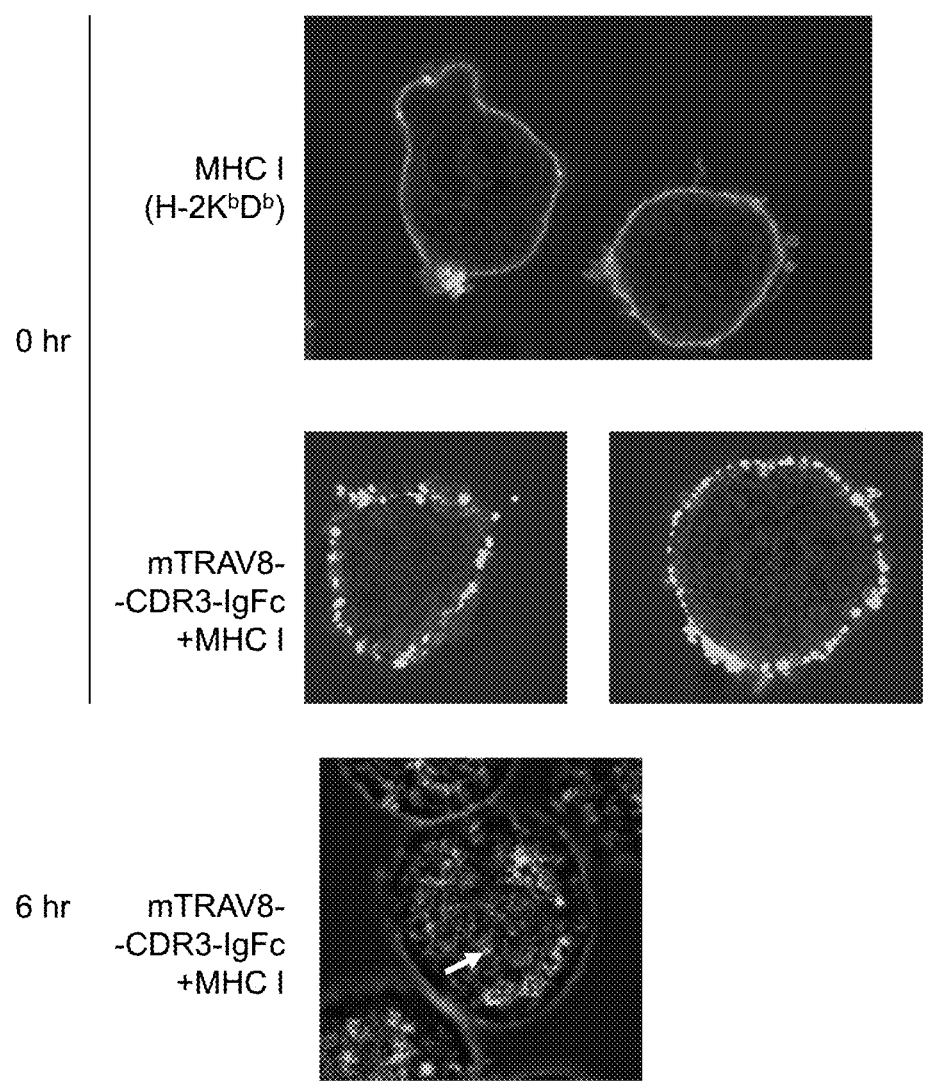
FIG. 22 shows cell internalization of a T-cell receptor chimeric protein bound to an MHC molecule.

Biotinylated mTRAV8-CDR3-IgFc (0.5 μg) was added to $2 \times 10^5$ E.G7 cells, and the cells were cultured at 4° C. for 1 hour. The cells were washed with PBS twice, resulting in the removal of mTRAV8-CDR3-IgFc not binding to MHC complexes. Next, streptavidin-FITC was added, resulting in dyeing at 4° C. for 30 minutes. The cells were washed with PBS twice, and the localization of mTRAV8-CDR3-IgFc was then observed through a fluorescence microscope over time (FIG. 22). Although it was found that only the cell membranes were dyed immediately after washing (0 hr), it was found that the inside of a cell was dyed (arrow in the figure) 6 hours after. It became clear that the T-cell receptor chimeric protein (mTRAV8-CDR3-IgFc) binding to the MHC complex was taken up by cells 6 hours after.

8. Decrease in Expression of MHC Complex by T-Cell Receptor Chimeric Protein (mTRAV8-CDR3-IgFc)

Figure 23:
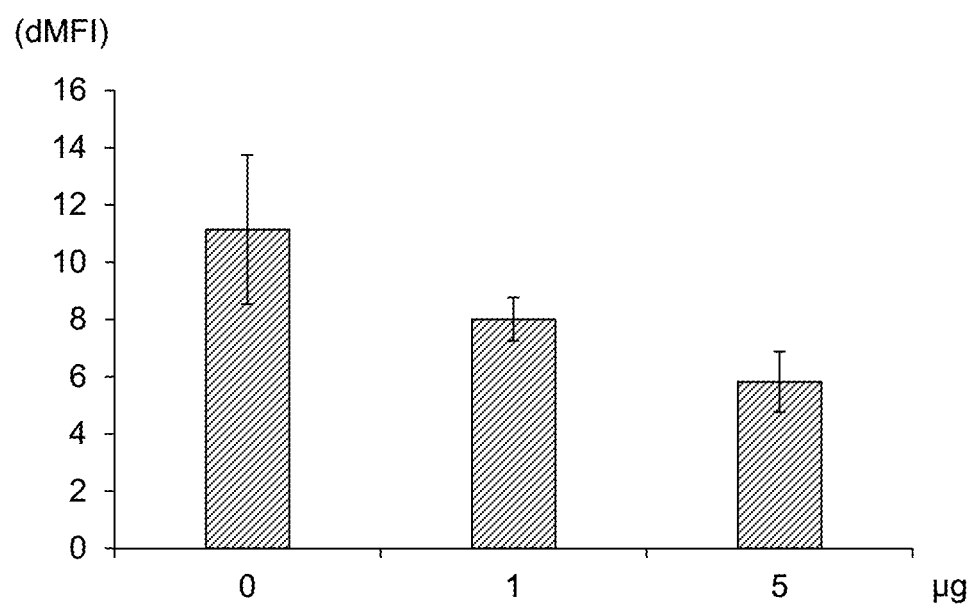
FIG. 23 shows down-modulation of an MHC complex by a T-cell receptor chimeric protein.

First, $1 \times 10^5$ E.G7 cells were cultured in the presence of mTRAV8-CDR3-IgFc (0, 1, 5 μg) for 6 hours. Then, the cells were dyed with the anti-H-2$K^bD^b$ antibody (BioLegend, Inc.) and measured by flow cytometry. The graph shows the difference of the mean fluorescence intensity value (MFI) on the basis of that of 0 μg of mTRAV8-CDR3-IgFc dMFI (FIG. 23). It turned out that a decrease in the expression of the MHC complex was seen 6 hours after the bond to the T-cell receptor chimeric protein.

9. Cellular Internalization of Human T-Cell Receptor Chimeric Protein (hTRAV21-CDR3-IgFc) and Decrease in Expression of MHC Complex by Human T-Cell Receptor Chimeric Protein Biotinylated hTRAV21-CDR3-IgFc (0.5 μg) was added to $2 \times 10^5$ Hela cells, which are a human cultured cell strain of cervical cancer, and the cells were cultured at 4° C. for 1 hour. The cells were washed with PBS twice, resulting in the removal of hTRAV21-CDR3-IgFc not binding to the MHC complex. Next, streptavidin-FITC was added, resulting in dyeing at 4° C. for 30 minutes. The cells were washed with PBS twice, and the localization of hTRAV21-CDR3-IgFc was then observed through the fluorescence microscope over time (FIG. 24A). Although it was found that the cell membrane portion was dyed immediately after washing (0 hr) (arrow), it was found that the inside of a cell was dyed 6 hours after (arrow). It was revealed that the T-cell receptor chimeric protein (hTRAV21-CDR3-IgFc) binding to the MHC complex was taken up by cells 6 hours after. As hTRAV21-CDR3 used here, hTRAV21-CDR3, which is TCR common to cervical cancer identified by examples 17 and 18, was used.

To Hela cells ($2 \times 10^5$) was added 0.5 μg of hTRAV21-CDR3-IgFc, and the cells were left to stand for 1 hour and then washed. Then, the culture medium was replaced with 5% FCS/DMEM, followed by culture on a 96-well plate for 6 hours. The cells were subjected to trypsin treatment, separated, dyed with the anti-HLA-A antibody (BioLegend, Inc.), and analyzed by flow cytometry (FIG. 24B). It turned out that a decrease in the expression of the MHC complex was seen also in human cells 6 hours after the cells were bound to the T-cell receptor chimeric protein.

Figure 25:
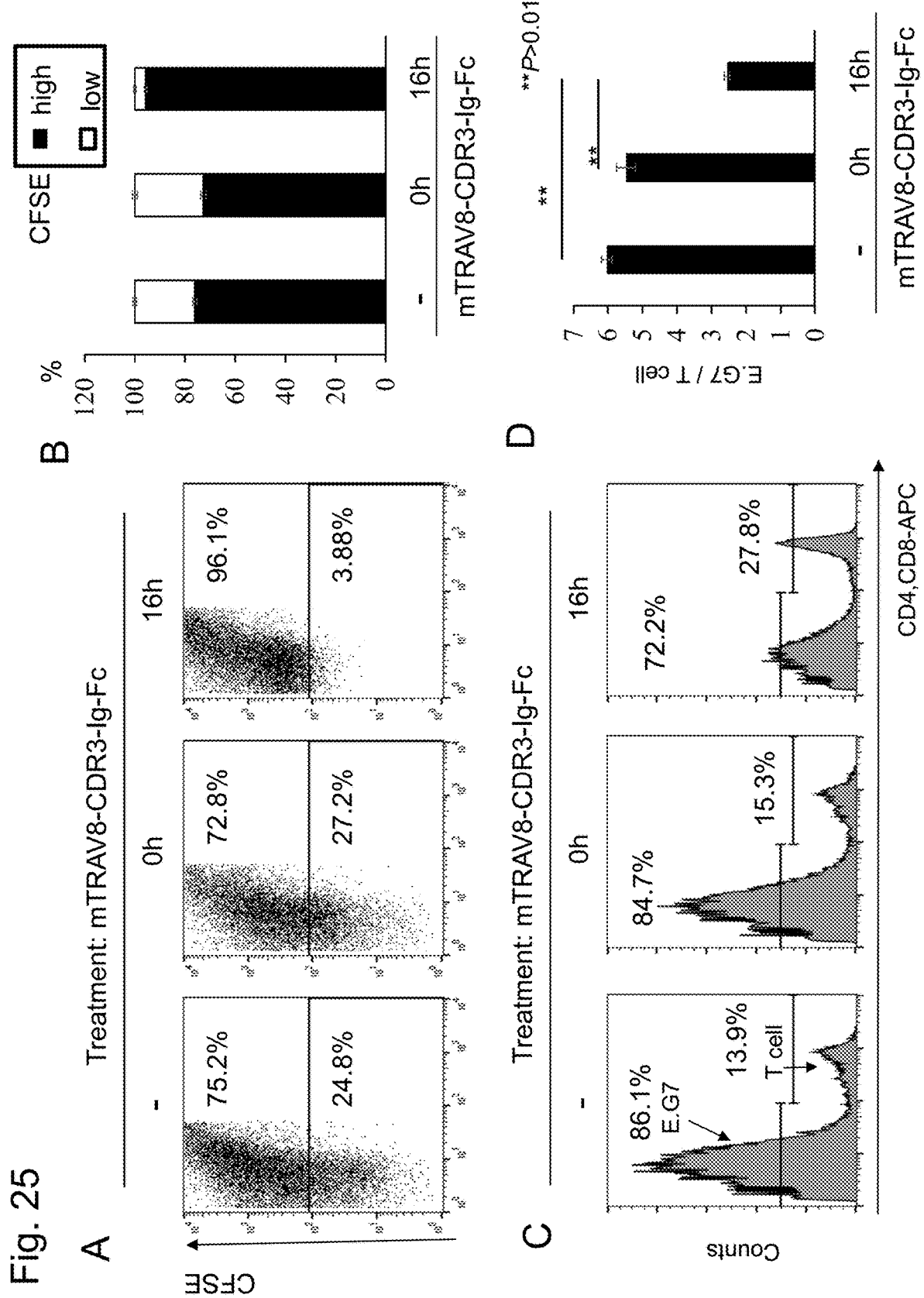
FIG. 25 shows growth inhibition of target cells using cell internalization by a T-cell receptor chimeric protein.

10. Proliferation Inhibition of Target Cells Using Cellular Internalization by T-Cell Receptor Chimeric Protein First, $1\times10^5$ E.G7 cells are fluorescence-labelled with CFSE and mixed with $1\times10^5$ mouse T-cells. mTRAV8-CDR3-IgFc (0.5 μg) was added to these cells, the cells were cultured at 4° C. for 1 hour and then washed with PBS twice. An anti-mouse IgG magnetic substance antibody (BioMag (registered trademark) anti-mouse IgG; Qiagen Corporation) was added, and the cells were cultured at 4° C. for 30 minutes and washed with PBS twice. After culture at 37° C. for 0 hours or 16 hours, a magnetic field was applied with an MRI (Bruker Corporation 7T-MRI) (3 tesla, 30 minutes). A group to which mTRAV8-CDR3-IgFc was not added was provided as a comparative control, and these samples were analyzed by flow cytometry 24 hours after (FIG. 25). In the group to which mTRAV8-CDR3-IgFc was not added and the group to which mTRAV8-CDR3-IgFc was added and that was cultured at 37° C. for 0 hours, fractions that decrease in the fluorescence of CFSE (CSFE low) were observed, and the division proliferation of E.G7 was found. Meanwhile, in the group to which mTRAV8-CDR3-IgFc was added and that was cultured at 37° C. for 16 hours, the proliferation of E.G7 was not found (FIG. 25A, B). Since the mouse T-cells were detected in all the groups, the adverse effect of a magnetic field on normal cells was not found (FIG. 25C). When the existence ratio of E.G7 to mouse T-cells was examined, the ratio of E.G7 in the group to which mTRAV8-CDR3-IgFc was added and that was cultured at 37° C. for 16 hours decreases as compared with those of the other groups (FIG. 25D). It was considered that the cells were injured specifically to cancer. These results were considered to be the hyperthermia effect of a magnetic field. This revealed that it was effective that the magnetic substance was taken up by the cells, and the T-cell receptor chimeric protein was effective as a drug that could perform injury specifically to target cells without affecting normal cells.

11. Function Enhancement of NK Cells by T-Cell Receptor Chimeric Protein

Figure 26:
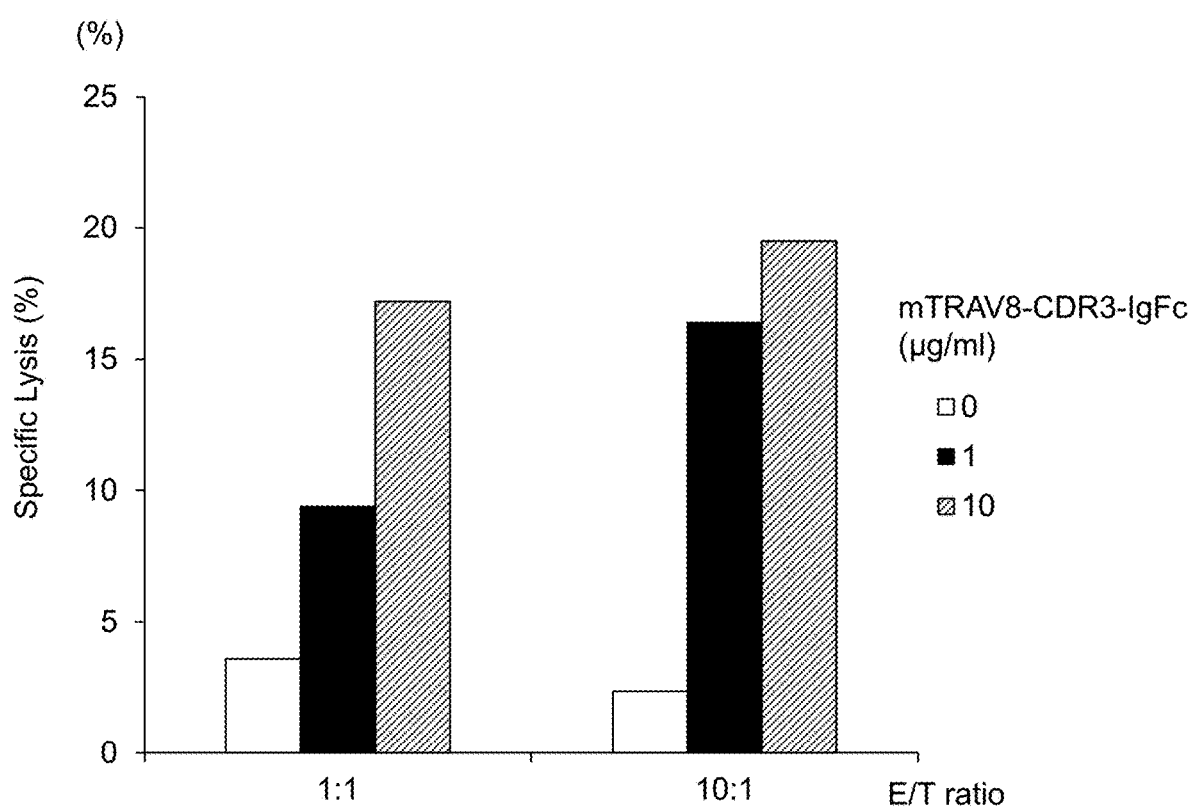
FIG. 26 shows a function enhancing effect of an NK cell by a T-cell receptor chimeric protein.

To $1\times10^4$ E.G7 cells were added 1, 10 μg/ml of mTRAV8-J42-IgFc, and the cells were cultured at 37° C. for 16 hours (quenching effect by taking up the MHC class I molecules in cells). These cells were used as a target cell, and NK cells that were isolation from the C57BL/6 mouse spleen beforehand and cultured in the presence of IL-2 (500 U/ml) were added. The cells were cocultured (the ratio of NK cells to EG7=1:1, 10:1). Dead cells were dyed with Propidium Iodide 4 hours after, and E.G7 the cell death of which was induced was calculated by flow cytometry analysis (FIG. 26). Decrease in the expression of MHC of the target cells by the T-cell receptor chimeric protein and cellular cytotoxicity activity by the following TCR-Ig fusion protein dependent cellular cytotoxicity, TDCC, effect were found.

12. T-Cell Receptor Chimeric Protein Dependent Cellular Cytotoxicity (TCR-Ig Fusion Protein Dependent Cellular Cytotoxicity; TDCC) Mechanism NK cells were isolated from mouse spleen lymphocytes. The NK cells were cultured in the presence of IL-2 (500 U/ml) for 7 days and proliferated, and these cells were used as effector cells.

Figure 27:
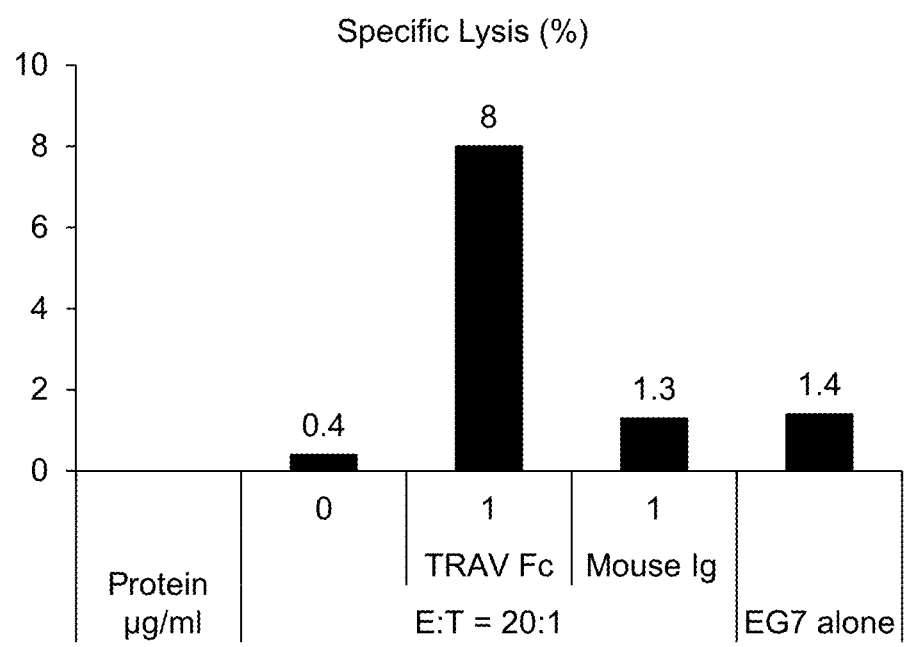
FIG. 27 shows that a cancer cell is damaged by T-cell receptor chimeric protein-dependent cellular cytotoxicity (TDCC: TCR-Ig fusion protein dependent cellular cytotoxicity) mechanism.

To $5\times10^4$ E.G7 cells was added 1 μg/ml of mTRAV8-CDR3-IgFc, and the cells were cultured at 37° C. for 30-minute and then washed with PBS twice. A control group obtained by adding 1 μg/ml of mouse IgG to $5\times10^4$ E.G7 cells, followed by culture at 37° C. for 30 minutes and washing the cells with PBS twice was provided. The effector cells were added to these target cells at a ratio of 20:1 (Effector:Target), followed by coculture at 37° C. for 4 hours. The cells were dyed with PI (Propidium Iodide) after coculture, and PI-positive cells in E.G7 cell fractions were analyzed by flow cytometry. The PI-positive cells were considered as dead cells, and the percentage thereof was evaluated. The result is shown in FIG. 27. As shown in FIG. 27, although NK cells could not kill cancer cells expressing MHC class 1 molecules without any treatment, the NK cells could kill 8% of cancer cells by coculturing with the T-cell receptor chimeric protein for 4 hours.

Figure 28:
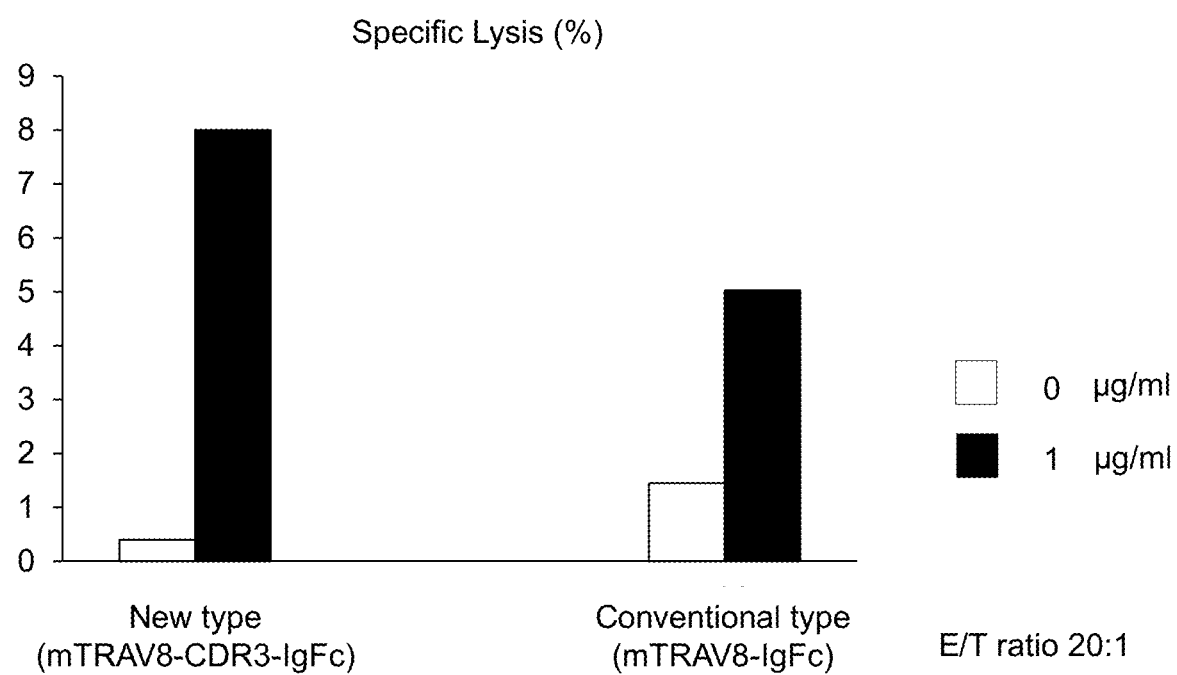
FIG. 28 shows a comparison between conventional type (mTRV8-IgFc) and new type (mTRAV8-CDR3-IgFc) T-cell receptor chimeric proteins in the T-cell receptor chimeric protein-dependent cellular cytotoxicity.

13. Comparison of Conventional (mTRAV8-IgFc) and New T-Cell Receptor Chimeric Protein (mTRAV8-CDR3-IgFc) in T-Cell Receptor Chimeric Protein Dependent Cellular Cytotoxicity NK cells were isolated from mouse spleen lymphocytes. The NK cells were cultured in the presence of IL-2 (500 U/ml) for 7 days and proliferated, and these cells were used as effector cells. To $5\times10^4$ E.G7 cells was added 1 μg/ml of mTRAV8-CDR3-IgFc or mTRAV8-IgFc, and the cells were cultured at 37° C. for 30 minute and then washed with PBS twice. A control group obtained by adding 1 μg/ml of mouse IgG to $5\times10^4$ E.G7 cells, followed by culture at 37° C. for 30 minutes and then washing the cells with PBS twice was provided. The effector cells were added to these target cells at a ratio of 20:1 (Effector:Target), followed by coculture at 37° C. for 4 hours. The cells were dyed with PI (Propidium Iodide) after coculture, and PI-positive cells in E.G7 cell fractions were analyzed by flow cytometry. The PI-positive cells were considered as dead cells, and the percentage thereof was evaluated (FIG. 28). It turned out that a CDR3 region moiety was effective, and the new T-cell receptor chimeric protein was efficient also in the comparison of TDCC effects using the conventional T-cell receptor chimeric protein.

14. Function Enhancement of NK Cell by Human T-Cell Receptor Chimeric Protein

Figure 29:
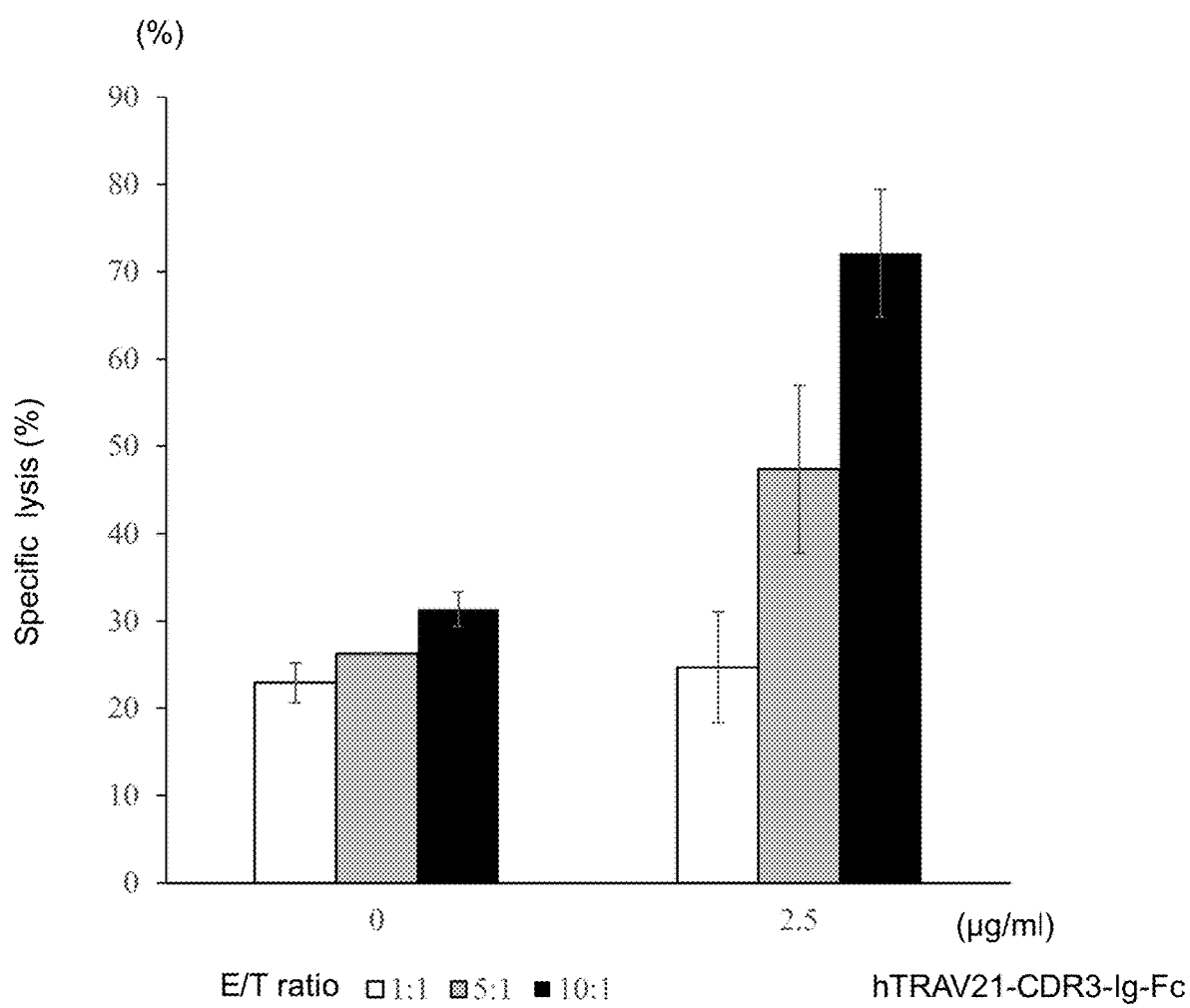
FIG. 29 shows a function enhancing effect of a human NK cell by a T-cell receptor chimeric protein.

To $1\times10^4$ Hela cells was added 0, 2.5 μg/ml of hTRAV21-CDR3-IgFc, followed by culture at 37° C. for 2 hours (quenching effect by taking up MHC class I molecules in the cell), and these cells were used as the target cell. The human NK cell culture strain NK92 was added, followed by coculture for 3 hours (the ratio of NK cells to cancer cells=1:1, 5:1, 10:1). The cellular cytotoxicity activity was evaluated using Cytotoxicity assay kit (Promega Corporation) (FIG. 29). Decrease in the expression of MHC of the target cells by the T-cell receptor chimeric protein and cellular cytotoxicity activity by TCR-Ig fusion protein dependent cellular cytotoxicity, TDCC, effect were found also in the human experimental system.

15. Suppression of Cancer Metastasis by T-Cell Receptor Chimeric Protein

The cancer cell E.G7 was fluorescence-labelled with CFSE, and a group to which 10 μg/ml of mTRAV8-CDR3-IgFc was added and simultaneously administered and an untreated group were provided. These $1\times10^6$ cancer cells were inoculated from the C57BL/6 mouse tail vein, and the number of E.G7 cells that metastasized to the spleen 24 hours after was measured. The numbers of E.G7 cells out of $3\times10^5$ spleen cells are shown (FIG. 30). As shown in FIG. 30, a cancer metastasis suppression effect by the T-cell receptor chimeric protein was found.

16. Method for Identifying Common TCR as to a Disease

Figure 31:
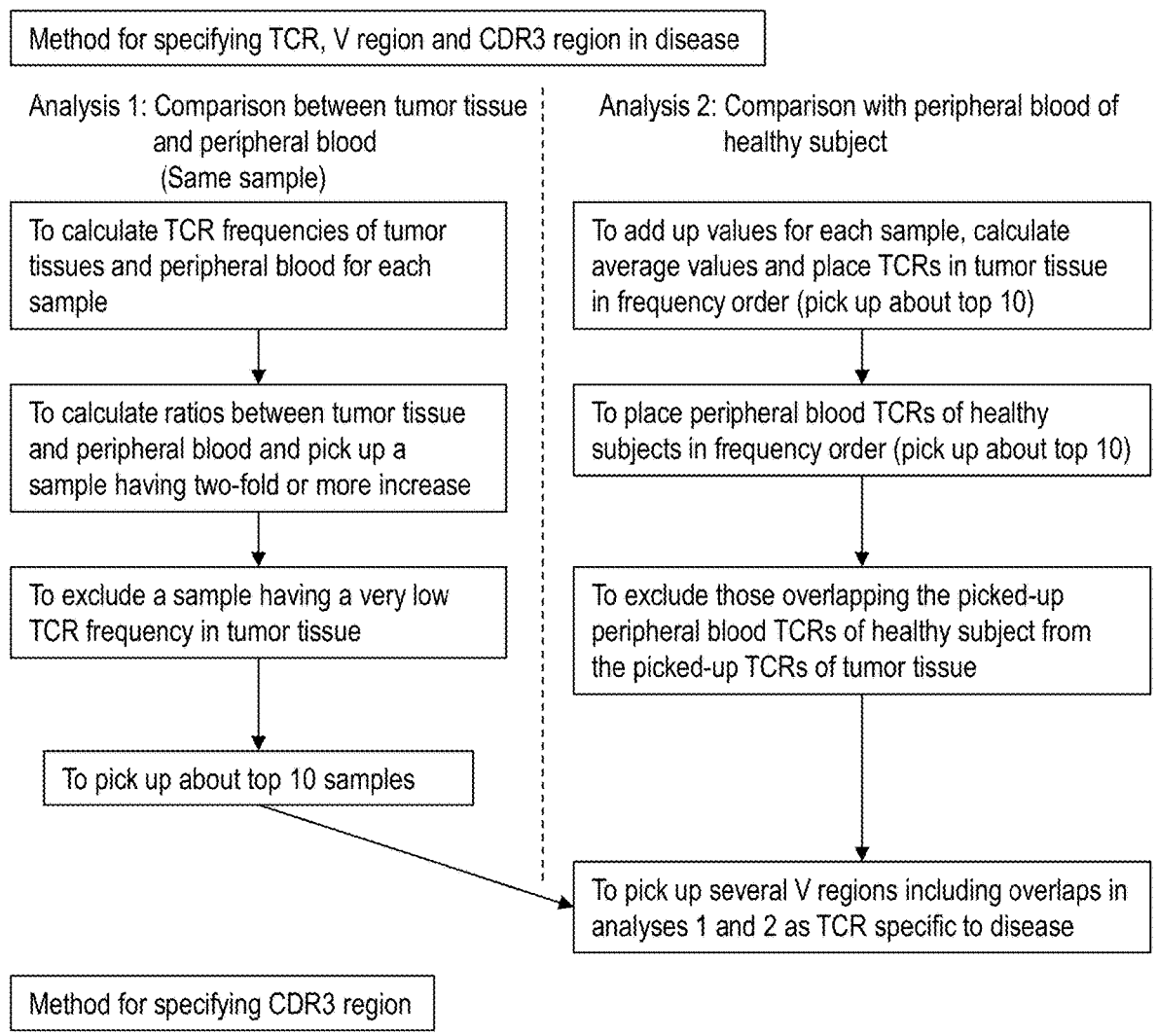
FIG. 31 shows a protocol of a method for specifying TCR common to diseases.

Methods for identifying common TCR in a disease were developed. The methods have a method by analysis 1 (comparison of tumor tissue and peripheral blood (the same sample)) and a method by analysis 2 (comparison with the peripheral blood of a healthy person). The protocols of the analysis 1 and the analysis 2 are shown in FIG. 31.

As the analysis 1, the TCR frequency of diseased surrounding tissue, for example, cancer surrounding tissue, and peripheral blood are compared. First, the TCR frequencies of the diseased tissue and the peripheral blood are calculated per sample. The TCR frequency of the diseased tissue and the TCR frequency of the peripheral blood are compared (TCR frequency of diseased tissue/TCR frequency of peripheral blood), and the V regions of TCRs the ratios of which are 2 or more are aligned (individual pair analysis). Diseased surrounding tissues having extremely low TCR frequencies, for example, less than 1%, are excluded. In individual pair analysis, TCRs ranking around fifth to tenth are sampled from TCRs having high ratios.

As the analysis 2, the frequencies of samples are added together as to the TCR frequencies in diseases tissues, and the average is found. The samples are put in order of frequency, and the top around 10 are sampled (total single analysis). The TCR frequencies of peripheral blood of healthy persons are put in order of frequency, and the top around 10 are sampled. TCRs sampled in the diseased tissues duplicating TCRs sampled from peripheral blood of healthy persons are excluded with the V region noticed, and these are considered as identified TCRs by the analysis 2.

The V regions of the TCRs selected in the analysis 1 and the analysis 2 are added together, and these are considered as common TCRs. Among the common TCRs, common TCRs that duplicate in the analysis 1 and the analysis 2 are considered as particularly important TCRs.

17. Identification of TCRs Common to Cervical Cancers

First, 5-mm cube tissues surrounding diseased sites were collected as samples from 15 patients with cervical cancer. Then, 10 ml of peripheral blood of each of the same patients was collected, monocytes were isolated by specific gravity centrifugation and used as a sample.

The total RNA was extracted from the above-mentioned samples, and cDNA libraries were produced in the usual method. The adapter was imparted, followed by PCR, and the genes of TCRs were amplified using "gene specific unbiased amplification". These were used as analysis samples. The samples were analyzed according to a protocol of the maker using the Roche454GS Junior or an illumina Miseq as a next generation sequencer.

Figure 32:
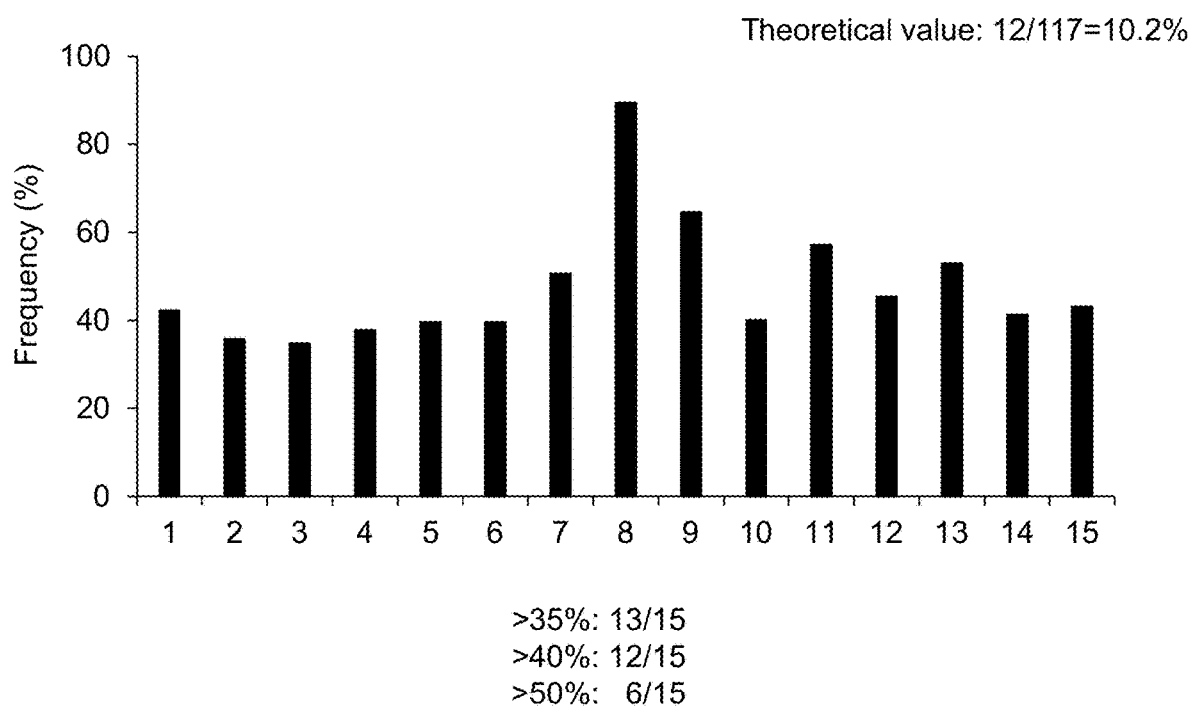
FIG. 32 shows results in specifying TCR common to cervical cancer.

Common TCRs were identified using the method for identifying common TCRs as to a disease. The result is shown in FIG. 32. The top 7 TCRs in the analysis 1 were TRAV1-1-01, TRAV1-1-02, TRAV21-02, TRAV22-01, TRAV1-2-01, TRAV12-2-03, and TRAV39-01. The top 7 TCRs in the analysis 2 were TRAV2-01, TRAV21-02, TRAV21-01, TRAV22-01, TRAV12-1-01, TRAV1-2-01, and TRAV38-2/DV8-01. Among these, TRAV21-02 and TRAV22-01 were common to the analysis 1 and the analysis 2. After all, the two analysis methods, the analysis 1 and the analysis 2, determined target TCRs having 12 T-cell receptor α chain variable regions, which were TRAV1-1-01, TRAV1-1-02, TRAV21-02, TRAV22-01, TRAV1-2-01, TRAV12-2-03, TRAV39-01, TRAV2-01, TRAV21-01, TRAV12-1-01, TRAV1-2-01, and TRAV38-2/DV8-01.

It is known that the repertoire of TCRs is not uniform, but is unbalanced when cancer-specific TCRs are present. The theoretical values of the frequencies of the 12 identified TCRs are added together, and the total is 10.2% (12/117). Nevertheless, the frequency of the above-mentioned 12 TCRs in the cervical cancer patient samples was higher than the theoretical value. Therefore, this results in the unbalanced repertoire of TCRs. Actually, the total frequency of the 12 TCRs was 35% or more in 13 samples, 40% or more in 12 samples, and 50% or more in 6 samples of the 15 samples, and was still higher than 10.2%, which was the theoretical value. This result shows that the above-mentioned 12 TCRs are TCRs specific to cervical cancer. Additionally, samples in which the total frequency of the 12 TCRs is 35% or more and is unbalanced as compared with the theoretical value are 13 samples of 15 samples (13/15=0.86). This means that the above-mentioned 12 TCRs are cancer-specific TCRs that are common to 80% or more out of cervical cancer patients.

18. Identification of CDR3s Common to Cervical Cancers

Figures 1, 33:
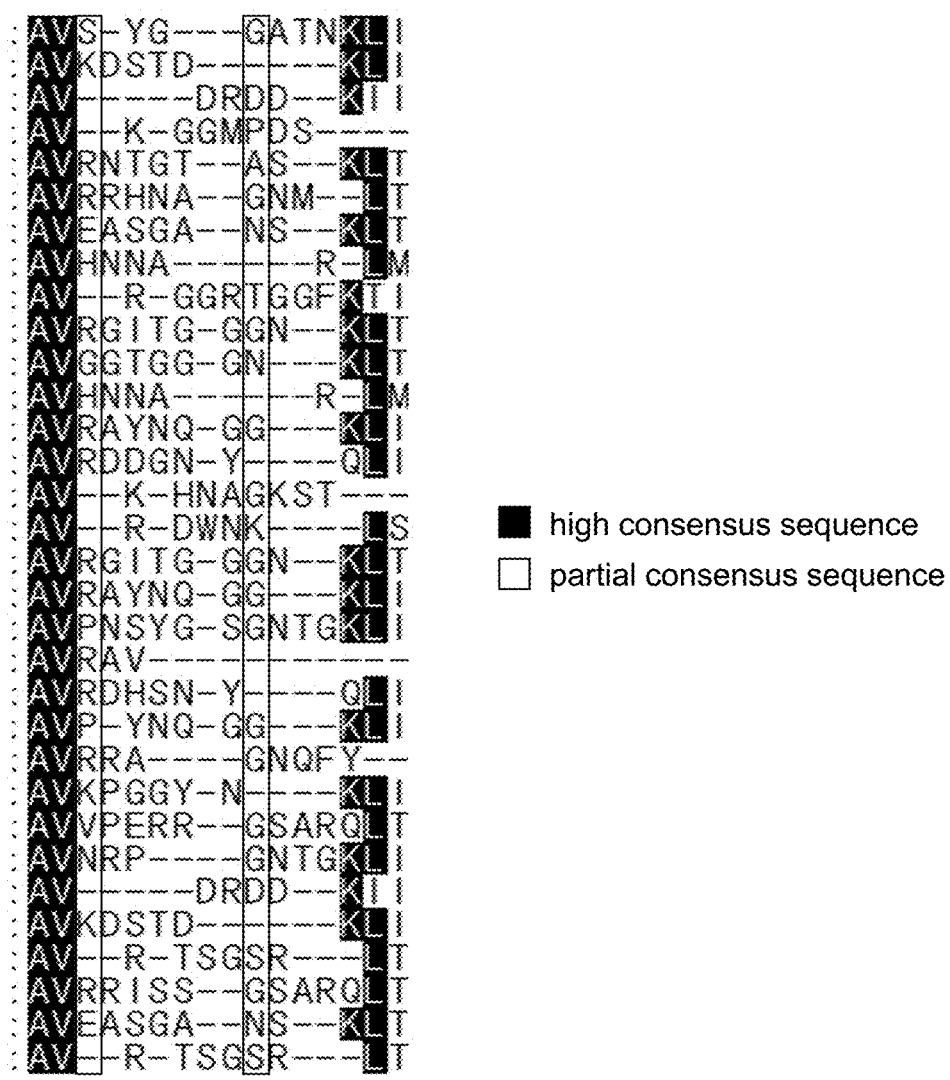
Figures 2, 33:
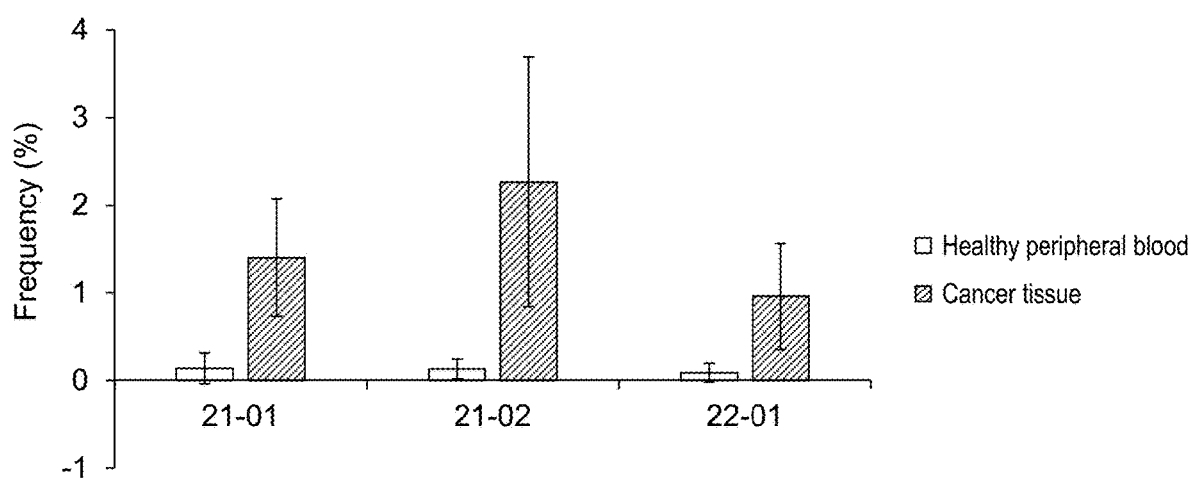

The top 5 CDR3 appearance frequencies of the patient tissues were sampled as to the V regions sampled in the method for identifying common TCRs as to the disease. The CDR3s of the V fields of all the cancer patient tissues were put in order of appearance frequency. As shown in FIG. 33-1, the CDR3s were summarized into 32 patterns. As shown in the figure, high consensus sequences and partial consensus sequences were present. The top 10 CDR3 patterns were sampled from these. The sampled CDR3s had many sequences including the amino acid sequence AVR significantly. Therefore, 32 patterns of sequences including AVR were aligned, resulting in the derivation of a further common sequence. A consensus frame set forth in (AVR—(x=1 to 6)—G—(x=1 to 3)—KL(I)/(T)) was identified as cervical cancer-specific CDR3. Then, 12 samples of the investigated 15 samples exhibit this specific CDR3 in V regions having particularly high appearance frequencies in the cancer patients specified in 17. (FIG. 33-2).

19. Detection of Infected Cells Using T-Cell Receptor Chimeric Protein

Figure 35:
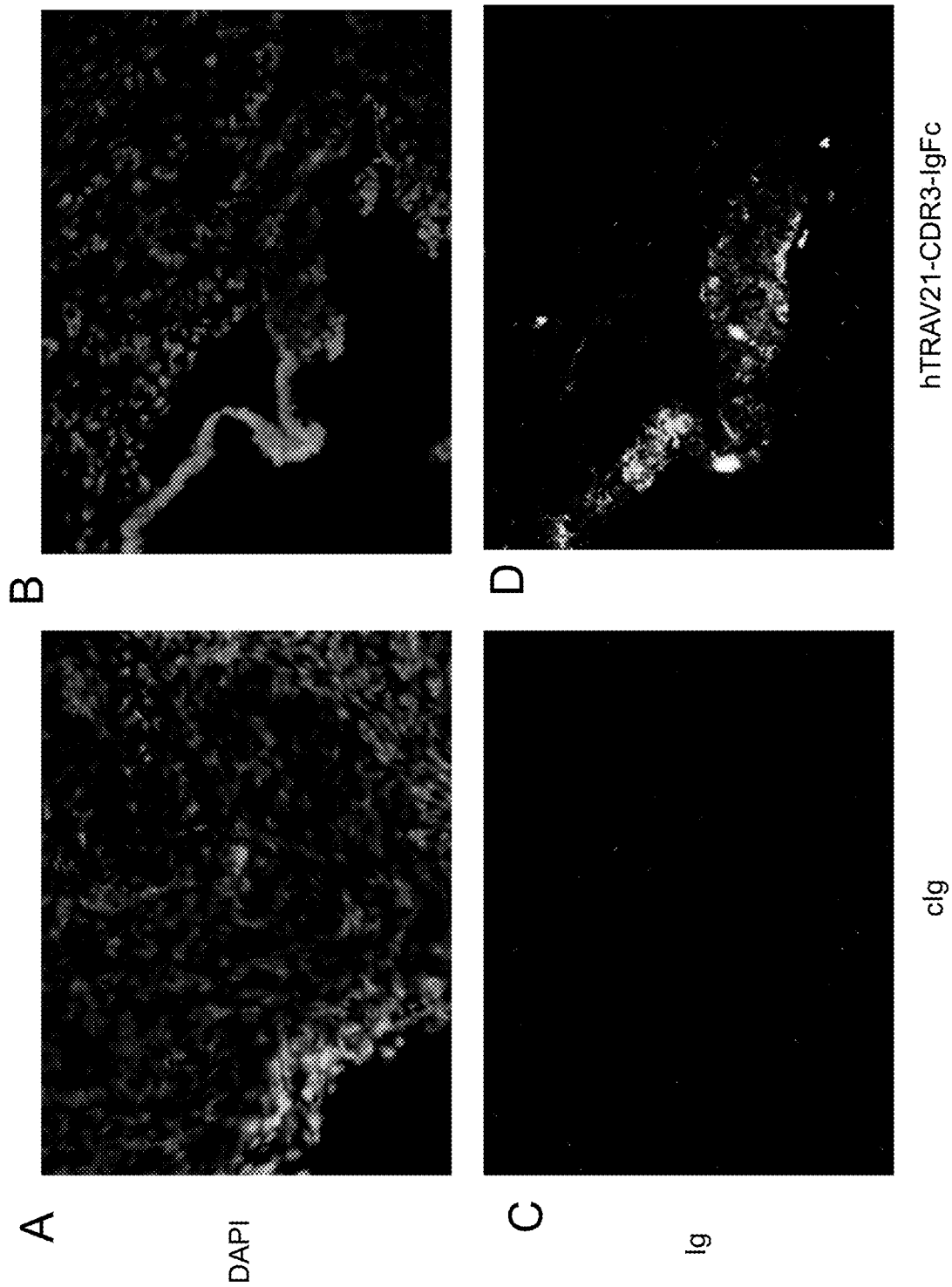
FIG. 35 shows results in detecting HPV infected cells by a T-cell receptor chimeric protein.

It was checked whether cervical cancer samples A and B, and an unknown sample C were infected with HPV or not. DNA was extracted from the samples, and HPV was detected with an HPV typing kit (Takara Bio Inc.). As shown in FIG. 34, HPV genes were detected in the samples A, B and C, and it was revealed that the samples A, B and C were infected with HPV 16, which is a malignant type. Additionally, it was found that the samples A and B were infected with HPV, and TRAV21 had a high TCR frequency. Therefore, it was attempted to detect infected cells of an HPV-infected patient sample (sample C) using a T-cell receptor chimeric protein (TRAV21-CDR3-IgFc) comprising TRAV21-02 and the common CDR3 that were determined in 17. and 18. A frozen embedded HPV-infected cervical tissue was cut thin to a thickness of 10 μm with a cryostat and fixed with acetone by the usual method. After blocking was performed with normal goat serum, hTRAV21-CDR3-IgFc (1 μg) was added, followed by culture at 4° C. for 16 hours. After washing, streptavidin-APC was added subsequently to a biotinylated anti-mouse IgG antibody, DAPI was added for nuclear dyeing, and the sample was observed through the fluorescence microscope. The result is shown in FIG. 35. FIG. 35A and B show an image dyed with DAPI, FIG. 35C shows an image that is dyed with Ig (control Ig: cIg) and is a control, and FIG. 35D shows an image fluorescently dyed with hTRAV21-CDR3-IgFc. HPV infected cells could be detected by the T-cell receptor chimeric protein (TRAV21-

CDR3-IgFc) (FIG. 35D). It was shown that the T-cell receptor chimeric protein could be used also to detect infected cells.

It also became clear at a subsequent date that the sample C was cervical cancer. Since TRAV21-CDR3 determined by 17. and 18. bound to cancer as a T-cell acceptor protein, it was also proved that TRAV21-CDR3 was cervical cancer-specific TCR.

20. Identification of TCR Common to Lung Cancers

First, 5-mm cube tissues surrounding diseased sites were collected from 13 patients having lung cancer as samples. Then, 10 ml of peripheral blood of each of the same patients was collected, and monocytes were isolated by the specific gravity centrifugation and used as a sample.

The total RNA was extracted from the above-mentioned samples, and cDNA libraries were produced in the usual method. The adapter was imparted, followed by PCR, and the genes of TCR chains were amplified using "gene specific unbiased amplification". These were used as analysis samples. The samples were analyzed according to a protocol of the maker using the illumina Miseq as a next generation sequencer.

Figure 36:
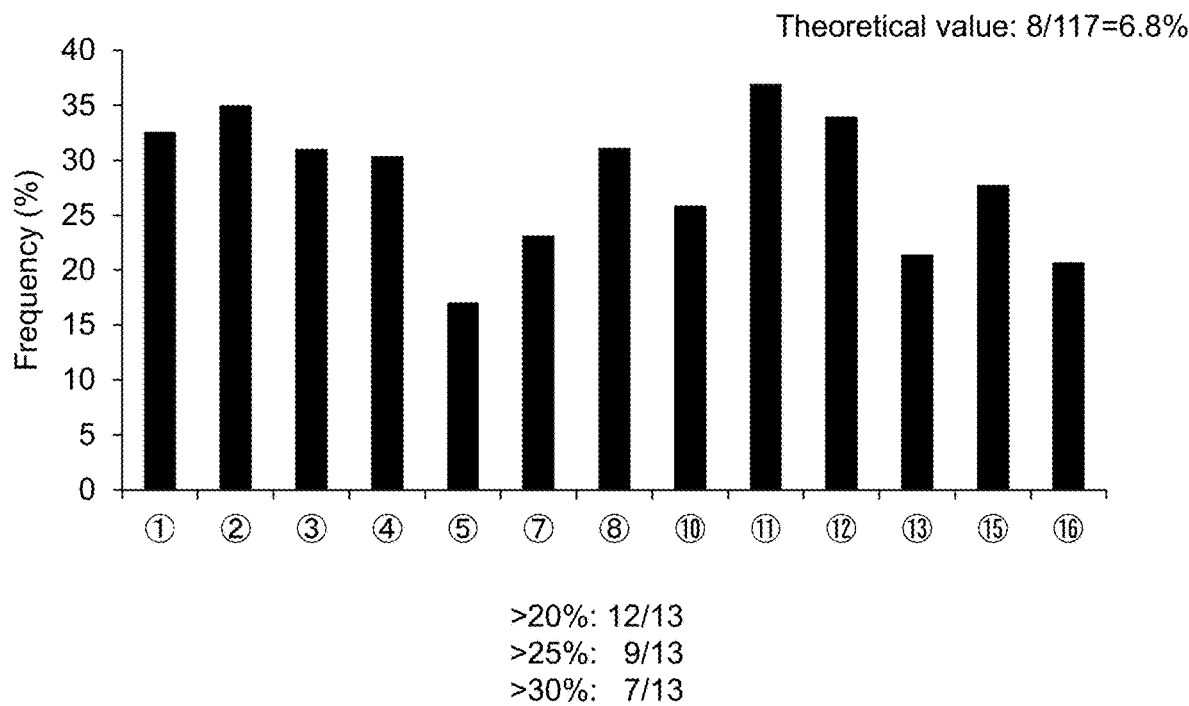
FIG. 36 shows results in specifying TCR common to lung cancer.

Common TCRs were identified using the method for identifying common TCRs as to a disease. The result is shown in FIG. 36. The top 5 TCRs in the analysis 1 were TRAV12-1-01, 16-01, 19-01, 22-01, and 35-02. The top 4 TCRs in the analysis 2 were TRAV19-01, 17-01, 9-2-02, and 13-1-01. Among these, TRAV19-01 was common to the analysis 1 and the analysis 2. After all, the two analysis methods, the analysis 1 and the analysis 2, determined target TCRs having a total of 8 T-cell receptor α chain variable regions, which were TRAV12-1-01, 16-01, 19-01, 22-01, 35-02, 17-01, 9-2-02, and 13-1-01.

It is known that the repertoire of TCRs is not uniform, but is unbalanced when cancer-specific TCRs are present. The theoretical value of the frequencies of the 8 identified TCRs is 6.8% (8/117). Contrarily, the total frequency of the 8 TCRs was actually 20% or more in 12 samples, 25% or more in 9 samples, and 30% or more in 7 samples of the 13 samples, and was still higher than the theoretical value, and the TCRs were unbalanced. This result shows that the above-mentioned 8 TCRs are lung cancer-specific TCRs. Additionally, samples in which the total frequencies of the 8 TCRs are 20% or more and are unbalanced as compared with the theoretical value are 12 samples of the 13 samples (12/13=0.92). This means that the above-mentioned 8 TCRs are cancer-specific TCRs that are common to 90% or more out of lung cancer patients.

21. Detection of Cancer Cells Using T-Cell Receptor Chimeric Protein

T-cell receptor chimeric proteins were prepared using TRAV19-CDR3 and TRAV35-CDR3 among the TCRs identified in 20. (TRAV19-CDR3-IgFc and TRAV35-CDR3-IgFc). It was attempted to detect cancer cells of a lung cancer patient sample in a lung cancer sample A using the T-cell receptor chimeric protein.

A frozen embedded lung diseased tissue was cut thin to a thickness of 10 μm with the cryostat and fixed with acetone by the usual method. After blocking was performed with normal goat serum, TRAV19-CDR3-IgFc or TRAV35-CDR3-IgFc (1 μg) was added, followed by culture at 4° C. for 16 hours. After washing, streptavidin-APC was added subsequently to a biotinylated anti-mouse IgG antibody, DAPI was added for dyeing nuclei, and the sample was observed through the fluorescence microscope (FIG. 37). FIGS. 37A, B and C show images dyed with DAPI, FIG. 37D shows an image that is dyed with Ig and is a control (control Ig: cIg), FIG. 37E shows an image dyed with fluorescence-labelled hTRAV35-CDR3-IgFc, and FIG. 37F shows an image dyed with fluorescence-labelled hTRAV19-CDR3-IgFc. Lung cancer cells could be detected with the T-cell receptor chimeric protein (TRAV19-CDR3-IgFc or hTRAV35-CDR3-IgFc) (FIG. 35D). It was shown that the T-cell receptor chimeric protein can be used also to detect cancer cells. This result also proves that since the TCRs identified in 20. bind to cancer as T-cell receptor proteins, the TCRs were lung cancer-specific TCRs.

All the publications, the patents and the patent applications cited herein are incorporated herein as reference as they are.

INDUSTRIAL APPLICABILITY

A T-cell receptor chimeric protein of the present invention can be used for the treatment and detection of cancer or infectious diseases.

SEQUENCE LISTING FREE TEXT

SEQ ID NOS: 1 to 31 synthesis
SEQ ID NOS: 32 and 33 primers

The invention claimed is:

1. An NK cell function enhancer comprising, as an active ingredient, a T-cell receptor chimeric protein being a fusion protein of a T-cell receptor variable region capable of recognizing a cancer-specific antigen, a CDR3, a J region, and an immunoglobulin Fc region, wherein the T-cell receptor chimeric protein is a construct of TRAV21-CDR3-IgFc which comprises TRAV21-02 as T-cell receptor a chain variable region and the CDR3 has the consensus sequence (AVR)X1GX2KL(I)/(T) in which X1=1 to 6 and X2=1 to 3, wherein the T-cell receptor chimeric protein binds to an MHC molecular complex of a cancer cell to reduce the expression of an MHC class I molecular complex and the cancer cell is killed or damaged by recognition of an NK cell or wherein the enhancer is for imparting a recognition function of a cancer cell expressing an MHC class I molecule to an NK cell to kill or damage the cancer cell by TDCC (T-cell receptor chimeric protein-dependent cellular cytotoxicity) activity.

2. The NK cell function enhancer according to claim 1, wherein the T-cell receptor variable region is an α chain and/or β chain of the T-cell receptor.

3. The NK cell function enhancer according to claim 1, wherein the immunoglobulin Fc region is an Fc region of IgG.

4. The NK cell function enhancer according to claim 1, wherein the T-cell receptor binds to an MHC class I molecule.

5. An NK cell function enhancer comprising, as an active ingredient, a T-cell receptor chimeric protein being a fusion protein comprising a T-cell receptor variable region capable of recognizing an antigen specific to a pathogen causative of an infection, a CDR3, a J region, and an immunoglobulin Fc region,
wherein the T-cell receptor chimeric protein is a construct of TRAV21-CDR3-IgFc which comprises TRAV21-02 as T-cell receptor α chain variable region and the CDR3 has the consensus sequence (AVR)X1GX2KL(I)/(T) in which X1=1 to 6 and X2=1 to 3,
wherein the T-cell receptor chimeric protein binds to an MHC class I molecular complex of an infected cell infected with the pathogen causative of the infection to reduce the expression of an MHC molecular complex and the infected cell is killed or damaged by recognition of an NK cell, or
wherein the enhancer is for imparting a recognition function of an infected cell infected with the pathogen causative of the infection, which expresses an MHC class I molecule, to an NK cell, and killing or damaging the infected cell by TDCC (T-cell receptor chimeric protein-dependent cellular cytotoxicity) activity.

6. The NK cell function enhancer according to claim 5, wherein the immunoglobulin Fc region is an Fc region of IgG.

7. The NK cell function enhancer according to claim 5, wherein the T-cell receptor binds to an MHC class I molecule.

8. The NK cell function enhancer according to claim 5, wherein the immunoglobulin Fc region includes constant domains CH2 and CH3 of a human natural immunoglobulin.

* * * * *